(12) United States Patent
Boger

(10) Patent No.: US 9,879,049 B2
(45) Date of Patent: Jan. 30, 2018

(54) GLYCOPEPTIDE ANTIBIOTIC ANALOGS EFFECTIVE AGAINST VANCOMYCIN-RESISTANT BACTERIAL STRAINS

(75) Inventor: Dale L. Boger, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 898 days.

(21) Appl. No.: 14/236,876

(22) PCT Filed: Aug. 3, 2012

(86) PCT No.: PCT/US2012/049548
§ 371 (c)(1),
(2), (4) Date: Jun. 3, 2014

(87) PCT Pub. No.: WO2013/022763
PCT Pub. Date: Feb. 14, 2013

(65) Prior Publication Data
US 2016/0272682 A1    Sep. 22, 2016

Related U.S. Application Data

(60) Provisional application No. 61/515,640, filed on Aug. 5, 2011, provisional application No. 61/554,679, filed on Nov. 2, 2011, provisional application No. 61/597,384, filed on Feb. 10, 2012.

(51) Int. Cl.
C07K 9/00     (2006.01)
A61K 38/14    (2006.01)
C07K 7/06     (2006.01)
A61K 38/00    (2006.01)

(52) U.S. Cl.
CPC .............. *C07K 9/008* (2013.01); *A61K 38/14* (2013.01); *C07K 7/06* (2013.01); *A61K 38/00* (2013.01)

(58) Field of Classification Search
CPC .................................................... C07K 9/008
See application file for complete search history.

(56) References Cited

U.S. PATENT DOCUMENTS

2007/0173438 A1    7/2007    Boger

FOREIGN PATENT DOCUMENTS

WO    WO-2007/084507 A2    7/2007
WO    WO-2013022763 A1    2/2013

OTHER PUBLICATIONS

"International Application Serial No. PCT/US2012/049548, International Preliminary Report on Patentability dated Feb. 20, 2014", 5 pgs.

James, Robert C., et al., "Redesign of Glycopeptide Antibiotics: Back to the Future", ACS Chemical Biology, 7(5), (2012), 797-804.
Xie, J., et al., "A Redesigned Vancomycin Engineered for Dual D-Ala-D-Ala and D-Ala-D-Lac Binding Exhibits Potent Antimicrobial Activity Against Vancomycin-Resistant Bacteria", J. Am. Chem. Soc., 133(35), (2011), 13946-13949.
Xie et al., J Am Chem Soc 134:1284-1297 (2012).
Okano et al., J Am Chem Soc 134:8790-8793 (2012).
Nicolaou et al., Angew Chem Int Ed 38:2096-2152 (1999).
U.S. PTO data base search for claims that recite "glycopeptide antibiotic".
"International Application Serial No. PCT/US2012/049548, International Search Report dated Jan. 18, 2013", 4 pgs.
"International Application Serial No. PCT/US2012/049548, Written Opinion dated Jan. 18, 2013", 6 pgs.
"International Application Serial No. PCT?US2012/049548, Invitation to Pay Additional Fees dated Nov. 14, 2012", 2 pgs.
Crowley, et al., "Total synthesis and evaluation of [?[CH2NH]Tpg4]vancomycin aglycon: reengineering vancomycin for dual D-Aia-D-Aia and D-Aia-D-Lac binding", J Am Chem Soc., vol. 128, No. 9, (Mar. 8, 2006), 2885-2892.
Kahne, D., et al., "Glycopeptide and lipoglycopeptide antibiotics", Chem Rev., 105(2), (Feb. 2005), 425-48.
Leung, et al., "Vancomycin analogs: Seeking improved binding of D-Aia-D-Aia and D-Aia-D-Lac peptides by side-chain and backbone modifications", Bioorg Med Chem., vol. 17, No. 16 (Aug. 15, 2009), 5874-5886.
Malabarba, A., et al., "Glycopeptide derivatives", Curr Med Chem., 8(14), (Dec. 2001), 1759-73.
Malabarba, A., et al., "Structural modifications of glycopeptide antibiotics", Med Res Rev., 17(1), (Jan. 1997), 69-137.
Van Bambeke, F., et al., "Glycopeptide antibiotics: from conventional molecules to new derivatives", Drugs, 64(9), (2004), 913-36.
Xie, Jian, et al., "Total Synthesis of [?[C(=S)NH]Tpg4]Vancomycin Aglycon, [?[C(=NH)NH]Tpg4]Vancomycin Aglycon, and Related Key Compounds:Reengineering Vancomycin for Dual D-Aia-D-Aia and D-Aia-D-Lac Binding", J Am Chem Soc., vol. 134, No. 2, (Jan. 18, 2012), 1284-1297.
Dale Boger—*Curriculum Vitae*.

(Continued)

*Primary Examiner* — Amber D Steele
(74) *Attorney, Agent, or Firm* — Husch Blackwell LLP

(57) ABSTRACT

The invention is directed to glycopeptide antibiotics and their aglycones that are engineered to overcome bacterial resistance by replacement of a single, specific peptide carboxamide group in the core peptide of the glycopeptide antibiotic with an amidine group. The amidine pseudopeptide analog of the glycopeptide is effective in killing vancomycin-resistant bacteria at therapeutically achievable concentrations in a patient. For example, a [Ψ[C(=NH)NH]Tpg$^4$]-vancomycin aglycon designed to exhibit the dual binding to D-Ala-D-Ala and D-Ala-D-Lac needed to reinstate activity against vancomycin-resistant bacteria has been shown to overcome a common mode of bacterial resistance to the "last resort" antibiotics of the glycopeptide class. The pseudopeptide amidine analogs can be prepared from corresponding pseudopeptide thioamide analogs, which can be prepared synthetically, semi-synthetically, or biosynthetically.

20 Claims, 4 Drawing Sheets

(56) References Cited

OTHER PUBLICATIONS

*CRC Handbook of Biochemistry Selected Data for Molecular Biology*, $2^{nd}$ ed., Sober ed., The Chemical Rubber Co., Cleveland, 1970 p. J-221.
Xie et al., *J Am Chem Soc* 133:13946-13949 (2011).
Extended European Search Report dated Feb. 3, 2016.

H-Bond
Increases $K_a$ 10-fold (1.5 kcal/mol)

|   | $K_a$ (M$^{-1}$) | $\Delta G°$ (25°C) |
|---|---|---|
| 2, X = NH | 4.4 x 10$^5$ | 7.7 kcal/mol |
| 3, X = CH$_2$ | 3.3 x 10$^4$ | 6.2 kcal/mol |
| 4, X = O | 4.3 x 10$^2$ | 3.6 kcal/mol |

Destabilizing lone pair interaction
Decreases $K_a$ 100-fold (2.6 kcal/mol)

| compound | ligand, $K_a$ (M$^{-1}$) | | $K_a$(6/7) | VanA[a] MIC (μg/mL) |
|---|---|---|---|---|
| | 6, X = NH | 7, X = O | | |
| 11, Y = NMe | 1.8 x 10$^3$ | 1.3 x 10$^3$ | 1.4 | 20 |
| 12, Y = NOH | 2.7 x 10$^2$ | 1.8 x 10$^2$ | 1.5 | >160[b] |
| 13, Y = NNH$_2$ | nd | nd | nd | > 40[b] |
| 14, Y = NCN | 5.7 x 10$^3$ | 4.9 x 10$^1$ | ≥120 | > 40[b,c] |
| 10, Y = NH | 5.7 x 10$^4$ | 6.3 x 10$^4$ | 0.9 | 0.31 |
| 8, Y = O | 1.4 x 10$^5$ | 1.3 x 10$^2$ | 1100 | >320[b] |
| 9, Y = S | 6.2 x 10$^2$ | 3.1 x 10$^1$ | – | >320[b] |

[a]MIC = minimum inhibitory concentration required for complete growth inhibition. *E. faecalis* (BM4166, VanA VRE). [b]Highest conc. tested. [c]MIC = 10 μg/mL against sensitive *S. aureus*.

| compound | ligand, $K_a$ (M$^{-1}$) 2, X = NH | 4, X = O | $K_a$(2/4) | VanA[a] MIC, μg/mL |
|---|---|---|---|---|
| 5, Y = O | 1.7 x 10$^5$ | 1.2 x 10$^2$ | 1400 | 640 |
| 47, Y = O | 1.4 x 10$^5$ | 1.3 x 10$^2$ | 1100 | > 320[b] |
| 46, Y = O | 1.8 x 10$^5$ | 1.1 x 10$^2$ | 1600 | 80 |
| 6, Y = H$_2$ | 4.8 x 10$^3$ | 5.2 x 10$^3$ | 0.9 | 31 |
| 7, Y = NH | 7.3 x 10$^4$ | 6.9 x 10$^4$ | 1.05 | 0.31 |
| 45, Y = NH | 5.7 x 10$^4$ | 6.3 x 10$^4$ | 0.9 | 0.31 |
| 43, Y = NH | 3.9 x 10$^4$ | 4.1 x 10$^4$ | 0.95 | 0.62 |
| 8, Y = S | 1.7 x 10$^2$ | [c]1.1 x 10$^1$ | – | > 640[b] |
| 44, Y = S | 6.2 x 10$^2$ | [c]3.1 x 10$^1$ | – | > 320[b] |
| 42, Y = S | 5.7 x 10$^2$ | [c]8.6 x 10$^1$ | – | > 800[b] |

[a]Minimum inhibitory conc., *E. faecalis* (BM4166, VanA VRE).
[b]Highest conc. tested.
[c]Estimate from ill-defined binding curve.

SEQUENCE LISTING

<160> NUMBER OF SEQ ID NOS: 14

<210> SEQ ID NO 1
<211> LENGTH: 7
<212> TYPE: PRT
<213> ORGANISM: Artificial Sequence

```
-continued

<220> FEATURE:
<223> OTHER INFORMATION: Any suitable bacterial strain
<220> FEATURE:
<221> NAME/KEY: VARIANT
<222> LOCATION: 2, 6
<223> OTHER INFORMATION: Phe = the hydroxylated, chlorinated derivative
      of the native form
<220> FEATURE:
<221> NAME/KEY: VARIANT
<222> LOCATION: 4, 5, 7
<223> OTHER INFORMATION: Xaa = hydroxylated, chlorinated derivative of
      the phenylglycine
<220> FEATURE:
<223> OTHER INFORMATION: A synthetic polypeptide

<400> SEQUENCE: 1

Leu Phe Asn Xaa Xaa Phe Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 1, 3, 4, 5, 7
<223> OTHER INFORMATION: Xaa = the hydroxylated, chlorinated derivative
      of phenylglycine
<220> FEATURE:
<221> NAME/KEY: VARIANT
<222> LOCATION: 2, 6
<223> OTHER INFORMATION: Phe = the hydroxylated, chlorinated derivative
      of the native form
<220> FEATURE:
<223> OTHER INFORMATION: A synthetic polypeptide

<400> SEQUENCE: 2

Xaa Phe Xaa Xaa Xaa Phe Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 2, 6
<223> OTHER INFORMATION: Phe = the hydroxylated, chlorinated derivative
      of the native form
<220> FEATURE:
<221> NAME/KEY: VARIANT
<222> LOCATION: 4, 5, 7
<223> OTHER INFORMATION: Xaa = the hydroxylated, chlorinated derivative
      of the phenylglycine
<220> FEATURE:
<223> OTHER INFORMATION: A synthetic polypeptide

<400> SEQUENCE: 3

Leu Phe Asn Xaa Xaa Phe Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
```

-continued

```
<222> LOCATION: 1, 4, 5, 7
<223> OTHER INFORMATION: Xaa = the hydroxylated, chlorinated derivative
      of phenylglycine
<220> FEATURE:
<221> NAME/KEY: VARIANT
<222> LOCATION: 2, 3, 6
<223> OTHER INFORMATION: Phe = the hydroxylated, chlorinated derivative
      of the native form
<220> FEATURE:
<223> OTHER INFORMATION: A synthetic polypeptide

<400> SEQUENCE: 4

Xaa Phe Phe Xaa Xaa Phe Xaa
1               5

<210> SEQ ID NO 5
<211> LENGTH: 7
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 1, 3, 4, 5, 7
<223> OTHER INFORMATION: Xaa = the hydroxylated, chlorinated derivative
      of phenylglycine
<220> FEATURE:
<221> NAME/KEY: VARIANT
<222> LOCATION: 2, 6
<223> OTHER INFORMATION: Phe = the hydroxylated, chlorinated derivative
      of the native form
<220> FEATURE:
<223> OTHER INFORMATION: A synthetic polypeptide

<400> SEQUENCE: 5

Xaa Phe Xaa Xaa Xaa Phe Xaa
1               5

<210> SEQ ID NO 6
<211> LENGTH: 4
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 1, 4
<223> OTHER INFORMATION: Phe = the hydroxylated, chlorinated derivative
      of the native form
<220> FEATURE:
<221> NAME/KEY: VARIANT
<222> LOCATION: 2, 3
<223> OTHER INFORMATION: Xaa = the hydroxylated, chlorinated derivative
      of phenylglycine
<220> FEATURE:
<223> OTHER INFORMATION: A synthetic polypeptide

<400> SEQUENCE: 6

Phe Xaa Xaa Phe
1

<210> SEQ ID NO 7
<211> LENGTH: 5
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 1, 5
<223> OTHER INFORMATION: Phe = the hydroxylated, chlorinated derivative
      of the native form
<220> FEATURE:
```

<221> NAME/KEY: VARIANT
<222> LOCATION: 2, 3, 4
<223> OTHER INFORMATION: Xaa = the hydroxylated, chlorinated derivative
      of phenylglycine
<220> FEATURE:
<223> OTHER INFORMATION: A synthetic polypeptide

<400> SEQUENCE: 7

Phe Xaa Xaa Xaa Phe
1               5

<210> SEQ ID NO 8
<211> LENGTH: 7
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 2, 6
<223> OTHER INFORMATION: Phe = the hydroxylated, chlorinated derivative
      of the native form
<220> FEATURE:
<221> NAME/KEY: VARIANT
<222> LOCATION: 4, 5, 7
<223> OTHER INFORMATION: Xaa = the hydroxylated, chlorinated derivative
      of phenylglycine
<220> FEATURE:
<223> OTHER INFORMATION: A synthetic polypeptide

<400> SEQUENCE: 8

Leu Phe Asn Xaa Xaa Phe Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 2, 6
<223> OTHER INFORMATION: Phe = the hydroxylated, chlorinated derivative
      of the native form
<220> FEATURE:
<221> NAME/KEY: VARIANT
<222> LOCATION: 4
<223> OTHER INFORMATION: Xaa = the hydroxylated, chlorinated derivative
      of phenylglycine and is further modified with an amidine group
<220> FEATURE:
<221> NAME/KEY: VARIANT
<222> LOCATION: 5, 7
<223> OTHER INFORMATION: Xaa = the hydroxylated, chlorinated derivative
      of phenylglycine
<220> FEATURE:
<223> OTHER INFORMATION: A synthetic polypeptide

<400> SEQUENCE: 9

Leu Phe Asn Xaa Xaa Phe Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 2
<223> OTHER INFORMATION: Ala = D-Ala
<220> FEATURE:
<223> OTHER INFORMATION: A synthetic polypeptide

<400> SEQUENCE: 10

Lys Ala Gly Gly Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 2
<223> OTHER INFORMATION: Ala = D-Ala
<220> FEATURE:
<223> OTHER INFORMATION: A synthetic polypeptide

<400> SEQUENCE: 11

Lys Ala Gly Gly Gly Gly Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Any suitable bacterial strain
<220> FEATURE:
<221> NAME/KEY: MUTAGEN
<222> LOCATION: 2
<223> OTHER INFORMATION: Ala = D-Ala
<220> FEATURE:
<223> OTHER INFORMATION: A synthetic polypeptide

<400> SEQUENCE: 12

Lys Ala Gly Gly Gly Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Any suitable bacterial strain
<220> FEATURE:
<221> NAME/KEY: VARIANT
<222> LOCATION: 4, 5
<223> OTHER INFORMATION: Ala = D-Ala
<220> FEATURE:
<223> OTHER INFORMATION: A synthetic polypeptide

<400> SEQUENCE: 13

Ala Glu Lys Ala Ala
1               5

<210> SEQ ID NO 14
<211> LENGTH: 5

```
<212> TYPE: PRT
<213> ORGANISM: Artificial Sequence
<220> FEATURE:
<223> OTHER INFORMATION: Any suitable bacterial strain
<220> FEATURE:
<223> OTHER INFORMATION: A synthetic polypeptide

<400> SEQUENCE: 14

Gly Gly Gly Gly Gly
1               5
```

GLYCOPEPTIDE ANTIBIOTIC ANALOGS EFFECTIVE AGAINST VANCOMYCIN-RESISTANT BACTERIAL STRAINS

CROSS-REFERENCE TO RELATED APPLICATIONS

This application is a national stage application under 35 U.S.C. § 371 of PCT/US2012/049548, filed Aug. 3, 2012, and published as WO 2013/022763 on Feb. 14, 2013, which claims the benefit of priority of U.S. Ser. Nos. 61/515,640 filed Aug. 5, 2011, 61/554,679 filed Nov. 2, 2011, and 61/597,384 filed Feb. 10, 2012, which applications and publication are incorporated by reference as if reproduced herein and made a part hereof in their entirety, and the benefit of priority of each of which is claimed herein.

STATEMENT OF GOVERNMENT SUPPORT

This invention was made with government support under grant numbers CA41101 and CA144333, awarded by the National Institutes of Health. The U.S. government has certain rights in the invention.

BACKGROUND

Antibiotic introduction in the early 20th century ushered in a new era in the treatment of microbial infections, providing the medical community with powerful drugs in its battle against disease. In addition to being among the first drugs introduced, antibiotics are also among the most successful, saving countless lives, extending life spans, and permitting previously deadly medical procedures. They represent 5% of the global drug market, and provide $42 billion in annual sales (2009).[1] One would be hard pressed to identify another drug class that enjoys such safe and widespread use, provides so successful health outcomes at such a modest cost, and has such a large economic impact. However, and from the very outset, this new revolution came with the concomitant induction of bacterial resistance to these treatments. The first reports of resistance followed only one year after the initial introduction of penicillin. Similarly, the introduction of methicillin in 1959, the next-generation drug for the treatment of penicillin-resistant strains, was followed only two years later by the emergence of methicillin-resistant *Staphylococcus aureus* (MRSA).[2] This cycle continues to be repeated again and again as new antibiotics are discovered and introduced into widespread use.

The glycopeptide antibiotics have long stood as an exception to this phenomenon. The lack of significant levels of clinical resistance to the two most commonly deployed members, vancomycin and teicoplanin, led to their adoption as drugs of last resort for the treatment of otherwise resistant and deadly infections. Recent years however have finally brought the onset of resistance to these important drugs. Herein, we review the origin of the past success with the glycopeptides antibiotics and the science behind the development of derivatives that address the emerging problem of acquired resistance in pathogenic bacteria, which we believe will provide an even more powerful future class of antibiotics than Nature could devise.

Vancomycin is the leading member of the class of clinically important glycopeptide antibiotics. Discovered at Eli Lilly, vancomycin was first disclosed in 1956[3] and introduced into the clinic in 1958, although its structure was not established until nearly 30 years later in 1983.[4] Following the emergence of MRSA, it became the drug of choice to treat resistant bacterial infections and it is also used for the treatment of patients on dialysis, undergoing cancer chemotherapy, or allergic to β-lactam antibiotics.[5] Today, more than 60% of the ICU *S. aureus* infections are MRSA, and its movement from a hospital-acquired to a community-acquired infection has intensified the impact of such resistant bacterial infections.[6] The onset of vancomycin resistance was long-delayed in comparison to all other antibiotics. Even after its first three decades of use, there was no notable resistance to vancomycin reported, and some even speculated that the development of resistance might be impossible.[7] Vancomycin resistant phenotypes were first reported in enterococci (VRE) in 1987, many years after the introduction of the drug into widespread clinical use, and today >30% of the ICU *Enterococcus faecalis* infections are VRE. Following the emergence of resistance in enterococci, which is now genetically transferred vertically, concern arose over the emergence of vancomycin-resistant *S. aureus* (VRSA) as a result of horizontal gene transfer from resistant enterococci. The first cases of fully vancomycin-resistant strains were reported in 2002,[8] and there have been an increasing number of cases of VRSA in the United States confirmed by the CDC.[9] A majority of VRSA has been found in patients co-infected with VRE, implicating horizontal gene transfer as the current method for acquiring vancomycin resistance.[10] As the prevalence of VRSA increases and as it establishes vertical gene transfer of resistance, new antibiotics with the longevity and dependability of vancomycin will be required to contain their impact. This need is arising at the same time that antibiotic discovery efforts are being discontinued at most major pharmaceutical companies. The reasons for this decline in antibiotic development are largely economic, resulting from a combination of patient short term use, the restricted use of new antibiotics with activity against resistant bacteria, and the increased regulatory criteria for approval.

Molecular Basis of Vancomycin Resistance

The mechanism of action of glycopeptide antibiotics involves the inhibition of bacterial cell wall synthesis by binding and sequestration of the integral precursor peptidoglycan peptide terminus D-alanine-D-alanine (D-Ala-D-Ala) in the developing cell wall, FIG. 1.[11] This precursor is tightly bound by the antibiotic, physically preventing transpeptidation and transglycosylation, arresting cell wall cross-linking and maturation, and leading to cell lysis. In the two most prominent manifestations of resistance (VanA and VanB), this cell wall precursor is remodeled to D-alanine-D-lactate (D-Ala-D-Lac), incorporating an ester linkage in place of the amide of the natural ligand.[12] Vancomycin-resistant bacteria sense the antibiotic challenge and subsequently remodel their precursor peptidoglycan terminus from D-Ala-D-Ala to D-Ala-D-Lac. Normal synthesis of lipid intermediate I and II, containing the D-Ala-D-Ala termini, continues but a late stage remodeling to D-Ala-D-Lac ensues to avoid the action of vancomycin. The binding affinity of the antibiotic for this altered ligand is reduced 1000-fold, resulting in a corresponding 1000-fold loss in antimicrobial activity.

SUMMARY

The invention is directed, in various embodiments, to analogs of glycopeptide antibiotics that have been devised to not only bind the D-Ala-D-Lac domain of the altered peptidoglycan terminus of vancomycin-resistant bacteria, but also maintain binding to the D-Ala-D-Ala domain of wild type bacteria; to methods of preparation of these glycopeptide analogs; and to methods of use of these glycopeptide analogs, for example, to treat infections caused by vancomycin-resistant bacteria such as VSRA. The inventors herein have surprisingly discovered that certain amidine and other analogs of glycopeptide aglycones, such as vancomycin aglycone, and related compounds, are effective in inhibiting bacterial growth in strains of bacteria that are resistant to vancomycin and vancomycin aglycone. The invention, in various embodiments, provides a method for designing and preparing a modified glycopeptide antibiotic to overcome bacterial resistance derived from the D-Ala-D-Ala to D-Ala-D-Lac alteration that is the basis for the antibiotic resistance found in resistant bacterial strains such as VanA and VanB.

In various embodiments, the invention provides methods of preparation of modified glycopeptide antibiotics, such as modified vancomycin compounds, that can be used in the treatment of infections in patients caused by vancomycin-resistant bacterial strains of the VanA and VanB types. The invention can provide synthetic and biosynthetic methods of preparation of a thioamide analog of a glycopeptide such as vancomycin, which is not antibiotic and can hence be produced in living bacterial production strains. The glycopeptide thioamide analogs can also be produced by total synthesis by means provided herein in conjunction with ordinary skill. Regardless of how the glycopeptide thioamide analogs are produced, they can be readily converted to the antibiotic amidine analogs, and other analogs such as alkylamidines, amidrazones, hydroxyamidines, and the like. For production of the parent amidine analogs, treatment of the glycopeptide thioamide analogs with ammonia and silver salts provides the antibiotic glycopeptide amidine analogs in good yield and purity.

In various embodiments, the invention provides methods of killing glycopeptide-resistant bacteria, and methods of treating patients infected with glycopeptide-resistant bacterial strains. As described above, the glycopeptides generally being medically considered as "last resort" treatments of infection, the present invention provides methods of keeping glycopeptide antibiotics as useful in this capacity, by overcoming resistance that has been developing in clinically significant bacterial lines.

DETAILED DESCRIPTION

Figure 1:
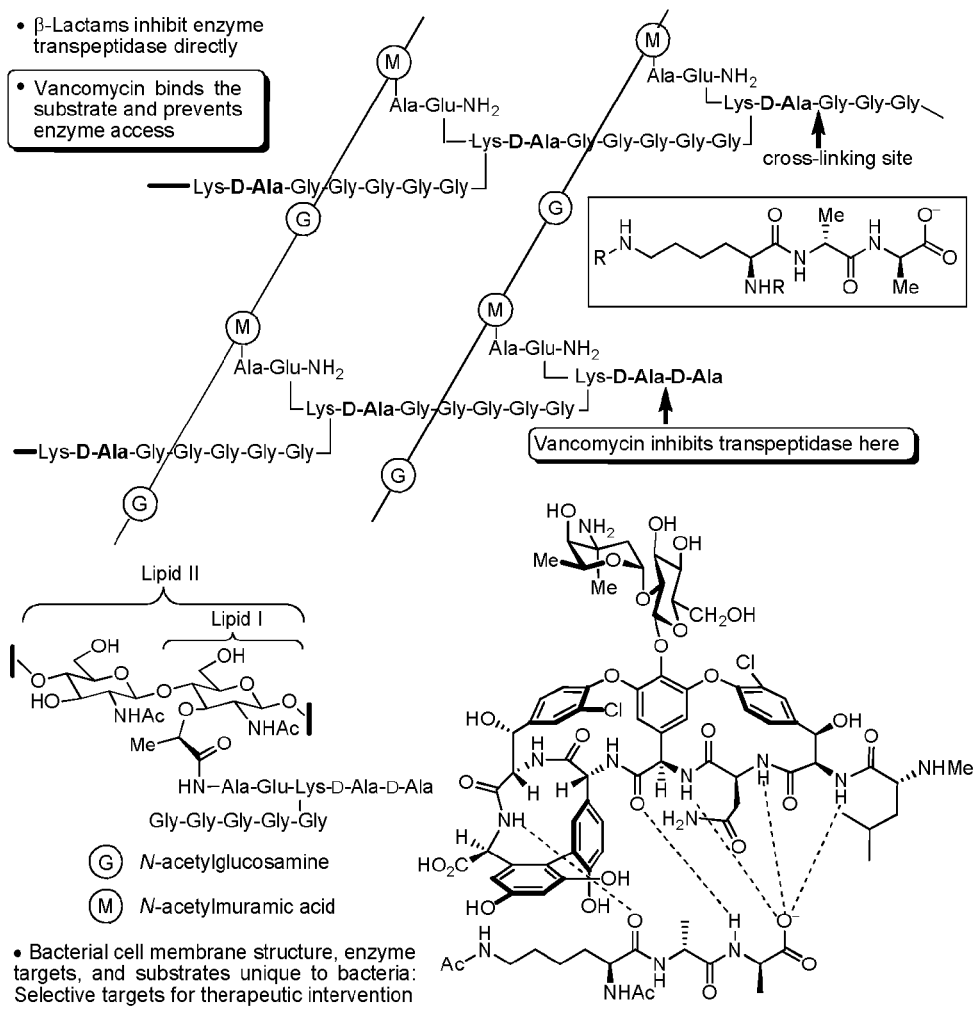
FIG. 1 shows a schematic of late stage bacterial cell wall synthesis and glycopeptide binding to D-Ala-D-Ala.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Standard abbreviations for chemical groups such as are well known in the art can be used herein, and are within ordinary knowledge; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The invention is directed, in various embodiments, to glycopeptide antibiotics that have been structurally modified in a particular way as disclosed and claimed herein to render the antibiotics effective versus bacterial strains that are resistant to vancomycin or other glycopeptide antibiotics; to methods of synthesizing the modified antibiotic compositions; and to methods of using the modified antibiotic compositions in killing of resistant bacterial strains and treatment of infections in patients caused by the antibiotic-resistant bacterial strains. As was discussed above, the major mode of resistance acquisition by bacterial strains to the antibiotic action of glycopeptides such as vancomycin the alteration of a D-alanine residue in the integral precursor peptidoglycan peptide C-terminus D-alanine-D-alanine to a D-lactic acid residue, changing an amide linkage to an ester linkage in the terminal dimeric unit of the peptidoglycan cell wall precursor. As the glycopeptide antibiotics are believe to inhibit the transpeptidase catalyzed cell wall forming reaction by sequestration of this precursor substance, when binding affinity of the glycopeptide antibiotic for the precursor is diminished, the effectiveness of the antibiotic in treatment of infections is diminished. By the above-described mutation, bacterial stains comprising the genes for this mutated form acquire thereby about a 1000-fold reduction in sensitivity to the glycopeptide antibiotics, prior to the present invention.

It has been surprisingly discovered by the inventor herein that by altering a single well-defined molecular grouping in a glycopeptide antibiotic, as exemplified by accomplishing and evaluating this change in the aglycone moiety of vancomycin, an antibiotic composition can be provided that is active versus both wild type and against vancomycin-resistant bacteria at therapeutically achievable antibiotic concentrations in vivo. In various embodiments, the present invention provides a so-termed [$\Psi$[C(=NH)NH]Tpg$^4$]amidine analog of vancomycin and vancomycin aglycone that exhibits antibiotic bioactivity versus vancomycin-resistant bacterial strains, having a high binding affinity for both the wild type (D-alanine-D-alanine) and the altered (D-alanine-D-lactate) C-terminal domain, respectively, of the integral precursor peptidoglycan peptide, resulting in the blockage of bacterial cell wall biosynthesis and mortality of the bacterial population. Due to the uniformity of the binding interaction of the glycopeptides as a class with their target precursor dipeptide D-Ala-D-Ala structure, the discovery herein provides a general method to design and prepare glycopeptide analogs, such as the amidine analogs described in detail below, useful for treatment of glycopeptide-resistant bacterial infections.

Vancomycin is an example of a glycopeptide antibiotic,

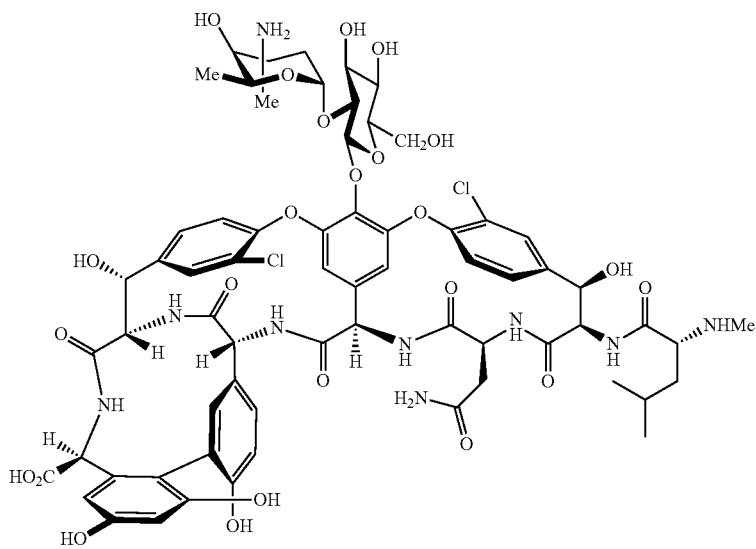

(vancomycin)

and is comprised by a family of glycopeptide antibiotics, further examples of which are provided below, having similar structural features and antibiotic profiles. Rings are labeled A, B, C, D, and E for ease of later reference, in analogy to the labeling used for other members of the glycopeptide antibiotic family, below.

For vancomycin, the aglycone, i.e., the deglycosylated derivative, is also active versus bacteria, and various of the Examples herein are experiments performed using vancomycin aglycone

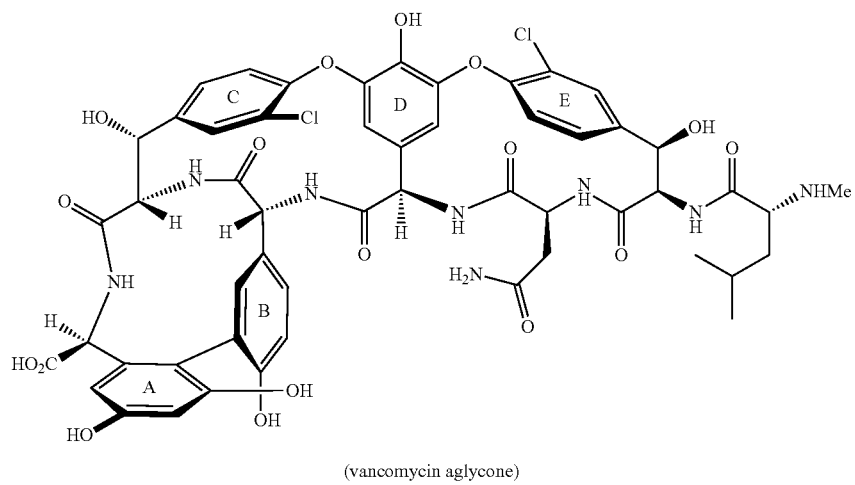

(vancomycin aglycone)

and modified forms thereof, such as thioamide and amidine analogs.

A "glycopeptide" or "glycopeptide antibiotic", as the term is used herein, refers to an antibiotic composition, including vancomycin, teicoplanin, balhimycin, actinoidin, ristocetin, and others, that comprises a core peptide (or pseudopeptide in the cases of the analogs herein) oligomer, that can be glycosylated in one or more position, wherein the core peptide sequence is about a hexapeptide unit comprising modified aminoacid residues, such as oxidized phenylalanine and phenylglycine residues, that are mutually coupled via aryl ether and biphenyl bonds, to form a multicyclic structure.

By a "core peptide" is meant the peptidyl structure than can theoretically be derived from the glycopeptide by the conceptual elimination of the aryl-aryl coupling bonds and by deglycosylation. For example, a "core peptide" of vancomycin, wherein all non-peptidic bonds have been conceptually broken, can be viewed as

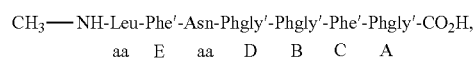

wherein the Phe' (phenylalanine) and Phgly' (phenylglycine) residues are substituted (hydroxylated, chlorinated) derivatives of the native forms of Phe and Phgly. For the sake of brevity, these aminoacid residues are abbreviated as Phe' and Phgly', and it is understood that these forms are modified forms of the aminoacid residues. In the actual molecular structure of the glycopeptides, further coupling reactions have taken place, providing various aryl ether and biphenyl moieties. The core peptide sequences are recited N-terminal to C-terminal, as is usual in the art, and "aa" signifies an aminoacid residue.

The A, B, C, D, and E rings as designated for the glycopeptides are indicated by the position of the corresponding letter directly beneath the residue. The modified Phe' and Phgly' residues as found in the glycopeptide

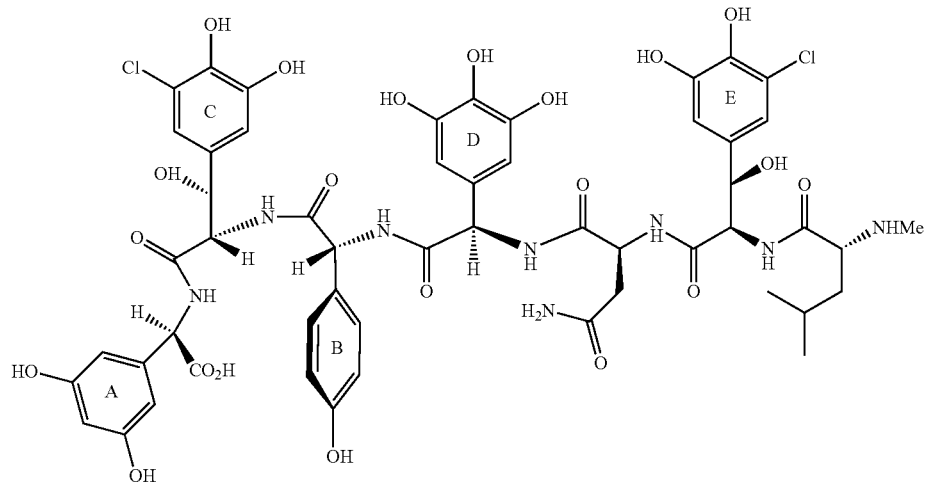

("peptide core" of vancomycin)

which can be summarized as the following vancomycin core peptide:

antibiotics can be oxidized (e.g., ring-hydroxylated, hydroxylated on a Phe benzylic carbon atom), ring-chlorinated, ring-ring coupled directly as a biphenyl, ring-ring coupled through an oxygen atom as a diaryl ether, and the like.

The core peptide structure, which can be slightly different among the various glycopeptide antibiotics, nevertheless is a highly conserved structure especially in the central domain of the peptide core, and it is believed that substantially all the glycopeptide antibiotics interact in a similar manner with the transpeptidase substrate as shown in FIG. 1 to inhibit bacterial cell wall formation.

Accordingly, a molecular change in this peptide core, as disclosed and claimed by the inventors herein, will consistently be useful to convert a glycopeptide antibiotic ineffectual against resistant strains of the VanA and VanB types into a glycopeptide effective as an antibiotic versus these resistant bacterial strains.

In all the examples provided herein, the C ring is coupled to the D and E rings via aryl ether or carbon-carbon bonds.

can be a free phenol, can be etherified, e.g., with other aryl groups in the molecule, or with methyls providing methoxyl groups, or can be glycosylated with carbohydrates including aminosugars and the like.

Oxidized phenylglycine and phenylalanine residues, as the terms are used herein, refer to residues that contain not only oxygenated aryl rings, but also hydroxylated or carbonyl-bearing benzylic carbons in the case of oxidized phenylalanine residues, as well as species where chlorine replaces hydroxyl on the ring, or where carbon-carbon bond formation between two rings has taken place. These structural features are common to the class of glycopeptide antibiotics.

An additional example of a glycopeptide antibiotic other than vancomycin is teicoplanin, having formula:

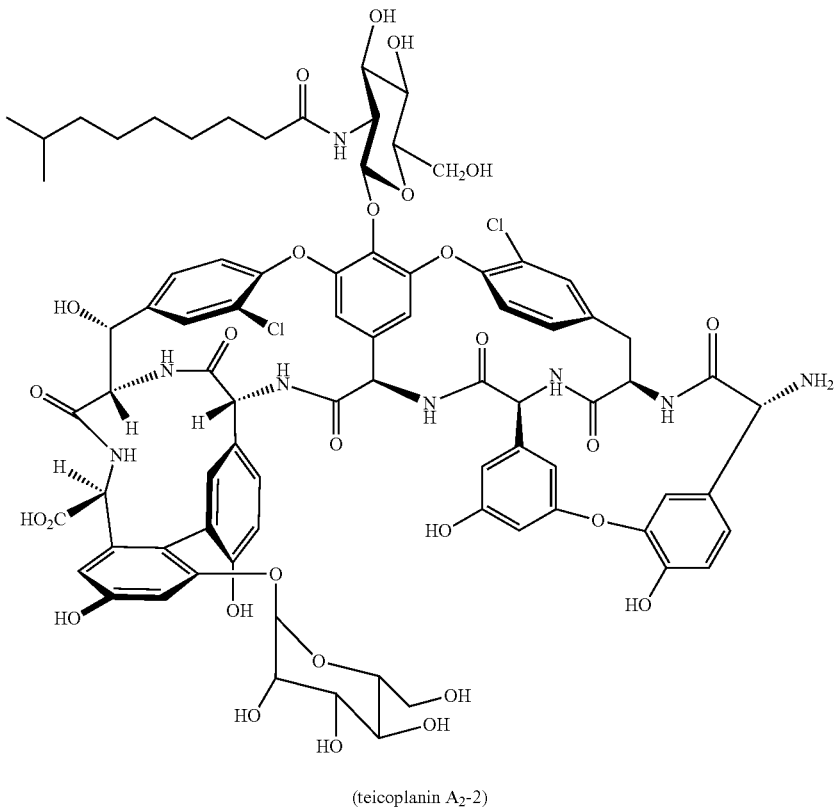

(teicoplanin A$_2$-2)

In the examples provided herein, for instance, the C and E rings are modified phenylalanine (Phe') residues and the D ring, coupled to both C and E rings, is a modified phenylglycine (Phgly') residue.

Examples of modified aryl aminoacid residues such as oxidized phenylglycine and phenylalanine residues include the oxygenated species seen above, which are further modified in the glypeptide antibiotics and their aglycones by formation of intramolecular aryl ether bonds and biphenyl bonds. For example, a substituted phenylglycine residue can include mono-, di-, and tri-substituted phenylglycines. When a ring is present in hydroxylated form, the resulting phenolic hydroxyl group in the intact glycopeptide antibiotic wherein the core peptide unit is:

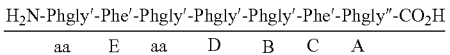

As can be seen from the above teicoplanin structure, the aryl ring labeled "D" is a phenyl ring of a modified phenylglycine aminoacid residue, bearing oxygen atoms in the 3-, 4-, and 5-positions of the phenyl ring. In teicoplanin, as in vancomycin, the 3- and 5-oxygen atoms substituents are in the form of aryl ethers with phenyl groups labeled "C" and "E", and the 4-oxygen is glycosylated with a carbohydrate derivative.

Additional examples include balhimycin,
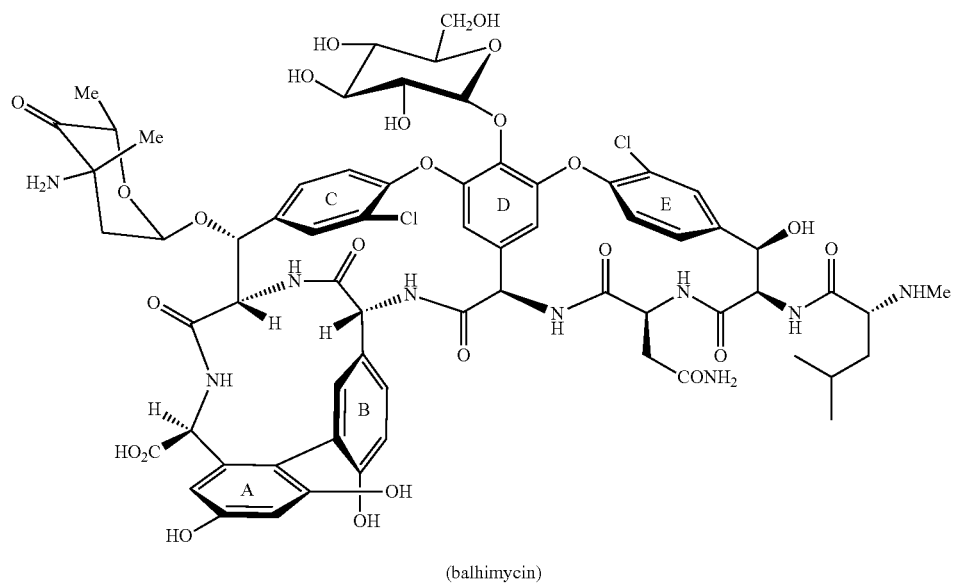
(balhimycin)
wherein the core peptide unit is:
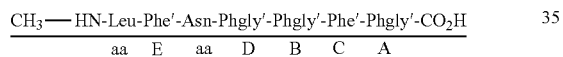
actinoidin A,
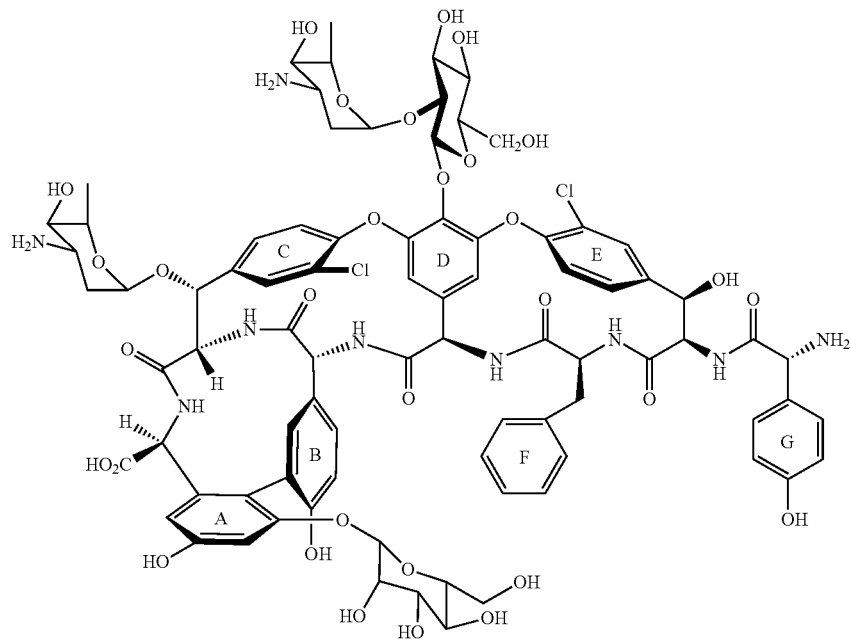

wherein the core peptide unit is:

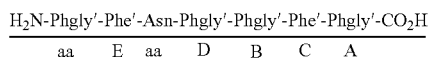

and ristocetin A,

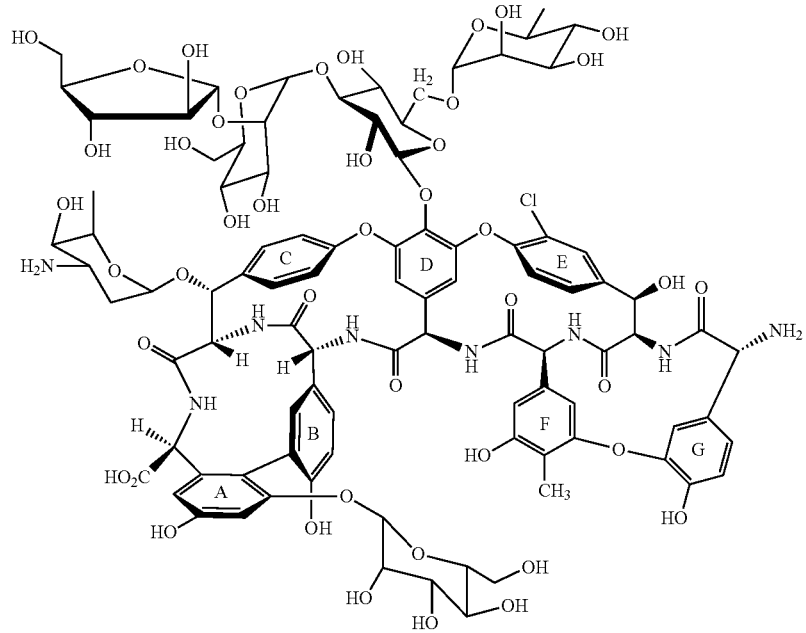

wherein the core peptide unit is:

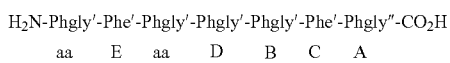

As can be seen, in all these glycopeptide antibiotics, the ring labeled D is a trihydroxyphenylglycine residue, bonded by its carboxyl group with the amino group of a modified phenylglycine residue, ring B. Ring D is also bonded by aryl ether bonds to rings C and E. The central domain of the contiguous aminoacid residues bearing rings D, B, C, (in the N-terminal to C-terminal direction) is consistently Phgly'-Phgly'-Phe'. The E ring-bearing aminoacid residue is consistently a modified phenylalanine residue, which can be separated from the D ring-bearing aminoacid residue by a variable residue; other residues may vary to some extent among the glycopeptides, although in all these five representative examples of glycopeptide antibiotics, the A ring-bearing aminoacid residue is a modified phenylglycine.

A core peptide conserved structure can comprise a peptide sequence including (from N terminal=>C terminal) aa-Phe'-aa-Phgly'-Phgly'-Phe'-Phgly', wherein additional amino acid residues can be present at either or both ends of this core peptide conserved structure, or can comprise a peptide sequence including (from N=>C terminal) aa-Phe'-Phgly'-Phgly'-Phgly'-Phe'-Phgly', wherein additional amino acid residues can be present at either or both ends of this core peptide conserved structure. These sequences correspond to aa-E-aa-D-B-aa-A, or aa-E-aa-D-B-C-A, respectively. In the amidine and the thioamide pseudopeptide analogs of the glycopeptides and their aglycones and analogs, disclosed below, it is the peptide bond carbonyl oxygen atom of the amino acid residue bearing the D ring that is modified to an NH or an S, respectively. Due to the conserved nature of the core peptide and the manner in which it complexes the peptidoglycan cell wall precursor in both wild type and vancomycin-resistant forms, these modifications have uniform results throughout the class of glycopeptide antibiotics and their aglycones and analogs.

Modified Glycopeptide Antibiotics Effective Versus Glycopeptide-Resistant Bacteria In various embodiments, the invention provides structural modifications of a glycopeptide antibiotic by which means the antibiotic can be engineered to enable full binding activity of the antibiotic to both the wild type D-alanine-D-alanine and the altered D-alanine-D-lactate terminal dipeptide domain of the precursor peptidoglycan used by bacteria in cell wall assembly. Accordingly, glycopeptides to which bacterial resistance has developed by this mechanism can be engineered using the insights and disclosures of the inventor herein, over a wide range of glycopeptide structures, provided that the binding interactions between the conserved core peptide structure of the antibiotic, and the wild type and mutant structures of the cell wall precursor peptidoglycan, are conserved and present.

As discussed above, a wide range of exemplary glycopeptide antibiotics share structural features that define the binding interactions between the various antibiotics of this class and the target terminal dipeptide domain of the infection-causing bacteria. The present inventor has determined that modification of one site of this conserved peptide core of the glycopeptide antibiotic structural class can serve to restore the hydrogen bonding interactions between the peptide core of the various antibiotics of the glycopeptide class, and the terminal dipeptide domain of the target cell wall precursor peptidoglycan when the common alteration involved in bacterial resistance has occurred. Due to the invariant nature of the wild type and altered target domains, and the highly conserved mode of binding of the peptide core among the glycopeptide antibiotics, this solution to the problem of overcoming bacterial resistance has wide applicability in the design of modified glycopeptide antibiotics.

aminoacid residue) with the corresponding amidine group, via a silver ion catalyzed reaction of the corresponding thioamide group (compound (IVA)) with ammonia.

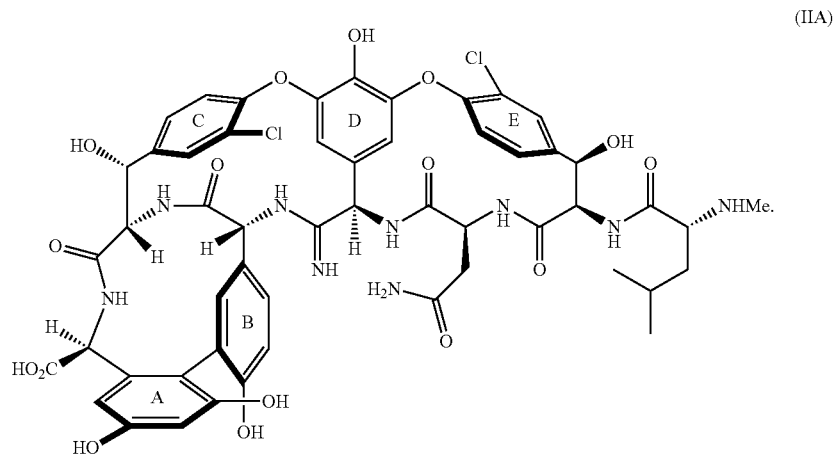

Figure 2:
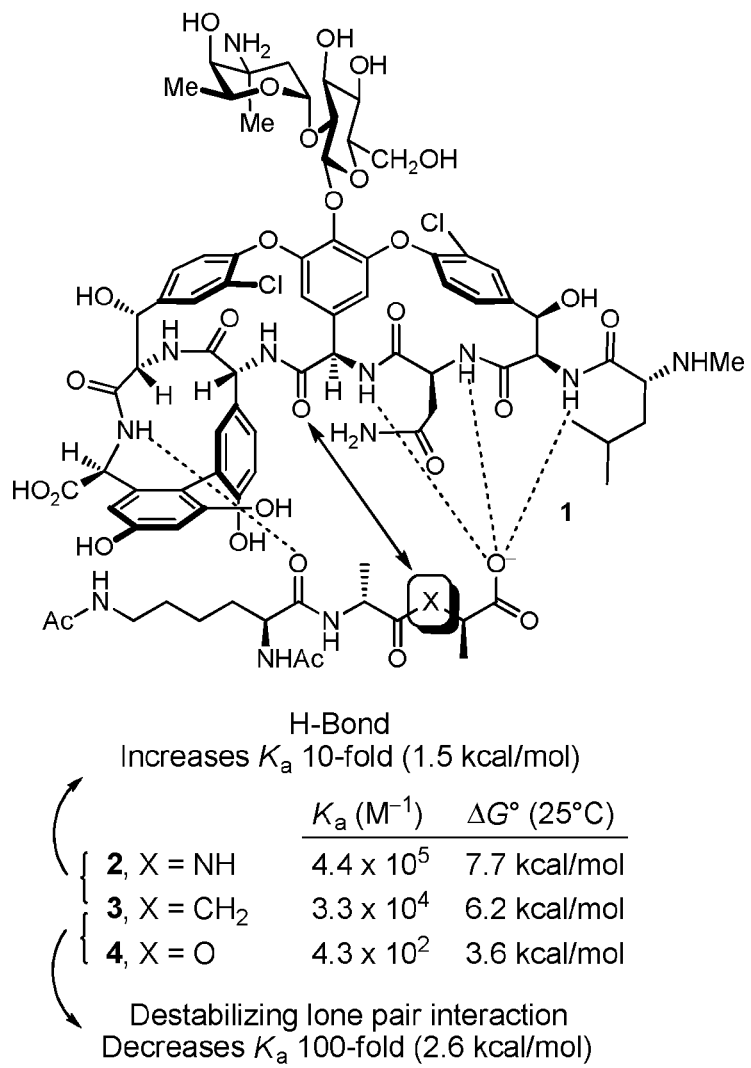
FIG. 2 illustrates the binding interactions between a glycopeptide antibiotic, e.g., vancomycin, and a peptidoglycan substrate target domain model compound, showing the hydrogen bonding interactions that control binding energetics.

FIG. 2 illustrates the binding interactions between a glycopeptide antibiotic, e.g., vancomycin, and a peptidoglycan substrate target domain model compound. When the alteration occurs, changing the nitrogen atom of the wild type D-Ala-D-Ala domain to the oxygen atom of the altered D-Ala-D-Lac domain, as can be seen, the indicated carbonyl group, which was an energetically favorable hydrogen bond recipient when a wild type NH group (shown as "X" in the schematic), i.e., substrate model 2, was present, now creates an enegetically unfavorable oxygen-oxygen lone pair repulsive interaction in substrate model 4 (X=O), resulting in a 3.1 kcal/mole loss in Gibbs free energy of binding ΔG° at 25° C. When a methylene group (X=CH$_2$) is present in the substrate model 3, about 1.5 kcal/mole free energy loss is seen. The experimental estimation of the magnitude of these two effects made by examining the substrate models 2-4, reveals that it is the repulsive lone pair interactions (100-fold), not the H-bond loss (10-fold), that is responsible for the largest share of the reduced binding affinity (1000-fold).[13] This shows that removal of the repulsive interaction along with restoration of a hydrogen bonding interaction at this position is necessary to restore glycopeptide binding for the mutant form wherein X is O to achieve the 1000-fold of increase in activity seen with the glycopeptide amidine analogs disclosed and claimed herein.

Applying these results with the model substrate to understanding of the complex of glycopeptides such as vancomycin with the altered D-Ala-D-Lac, it is apparent that the altered interaction lacks the central H-bond as is present in the D-Ala-D-Ala complex, and furthermore suffers a repulsive lone pair interaction between the vancomycin residue D-ring aminoacid residue carbonyl (i.e., residue-4, position Tpg$^4$) and the D-Ala-D-Lac ester oxygen atom.

In conjunction with studies on the total synthesis of the glycopeptide antibiotics[14-19] and concurrent with efforts probing systematic modifications to vancomycin itself,[20] a site-specific pseudopeptide amidine analog of vancomycin aglycon (IIA), termed [Ψ-[C(=NH)NH]Tpg$^4$]-vancomycin aglycone, was prepared, replacing the residue-4 amide (i.e., the C-terminal amide or peptide bond of the D ring-bearing The resulting favorable antibiotic properties of the compound formula (IIA) demonstrates that incorporation of the amidine pseudopeptide bond on the C-terminal for the aminoacid residue bearing the D ring (termed the residue-4 amidine for the vancomycin example herein) can accommodate D-Ala-D-Lac binding by removing the destabilizing electrostatic interaction and serving as a H-bond donor, while simultaneously maintaining affinity for D-Ala-D-Ala by virtue of serving as a H-bond acceptor (FIG. 2).

This position of replacement of the peptide carboxamido group in vancomycin aglycone, core peptide sequence of vancomycin aglycone being:

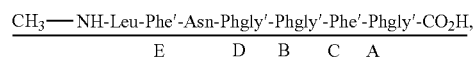

the [Ψ-[C(=NH)NH]Tpg$^4$] amidine analog can be depicted in the following manner:

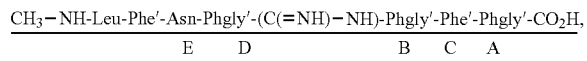

wherein the amidine —(C(=NH)—NH) group is understood to replace the carboxamide —(C(=O)—NH)— group in the same orientation, i.e., the C=NH group is formally part of the D ring-bearing Phgly' residue, and the NH is formally part of the B ring-bearing Phgly' group in the example above, according to standard peptide structural conventions. In all the examples of glycopeptide antibiotics herein, the carboxamide group that is replaced with an amidine group according to the invention herein is disposed between the D ring-bearing residue and the residue immediately C-terminal of this residue, which in all these specific examples is the B-ring-bearing Phgly' residue. In other glycopeptides, the B ring-bearing residue may not be immediately adjacent to the D ring-bearing residue; nevertheless, the altered carboxamide group according to the invention herein is the carboxamide the carbonyl of which is part of the D ring-bearing aminoacid residue.

Such binding characteristics of the antibiotic composition of formula (IIA) were not easily predictable, as it is not clear whether the ester oxygen of D-Ala-D-Lac could serve as a H-bond acceptor, or whether an amidine, which is likely protonated, might remain a good H-bond acceptor for D-Ala-D-Ala. Since the utility of an amidine as an amide isostere in peptides has been essentially unexplored,[21-23] the projected binding properties of the vancomycin aglycone amidine-analog of formula (IIA) were even more unpredictable.

The vancomycin aglycone amidine analog of formula (IIA) was prepared via the thioamide of formula (IVA), termed [Ψ-[C(=S)NH]Tpg4]vancomycin aglycone, which itself was prepared by total synthesis, but would also, using known methods within ordinary knowledge, be accessible by biosynthesis in bacterial production fermentation processes using appropriate precursors. The lack of antibiotic bioactivity of the glycopeptide thioamide analogs makes them suitable for fermentation production by bacterial lines, but the glycopeptide amidine analogs are far too toxic to bacteria for direct fermentation production. The thioamide of formula (IVA) was then used in a single-step, site-specific, and high yield amidine introduction by use of silver ion catalysis in ammonia, disclosed and claimed herein, as described in greater detail below, yielding the [Ψ-[C(=NH)NH]Tpg4] vancomycin aglycone amidine analog of formula (IIA).

pounds, that are effective as antibiotics at therapeutically achievable concentrations, i.e, comparable to the effective concentration of the parent glycopeptide versus a wild type bacterial strain.

Thus, using the disclosure herein in conjunction with the knowledge of the person of ordinary skill, it is possible to prepare and use a modified glycopeptide antibiotic containing this amidine-modified peptide bond, of the carbonyl group of the aminoacid residue bearing ring D, that exhibits high affinity binding for both the wild type (D-Ala-D-Ala) and the altered (D-Ala-D-Lac) cell wall precursor terminal dipeptide domains, and thus is active against both wild type and vancomycin-resistant bacterial strains expressing this change.

Accordingly, the inventor herein discloses and claims glycopeptide antibiotics comprising an amidine modification of the D ring aminoacid residue carbonyl group as described herein. The D ring aminoacid residue is the aromatic aminoacid residue common to glycopeptide structures wherein the carbonyl group of the residue in the native glycopeptide structure, forming a peptide bond with the next aminoacid residue C-terminal thereto, forms a hydrogen bond with the nitrogen atom of the peptide bond of the D-Ala-D-Ala terminal dipeptide domain of the peptidoglycan bacterial cell wall precursor as defined herein. The D

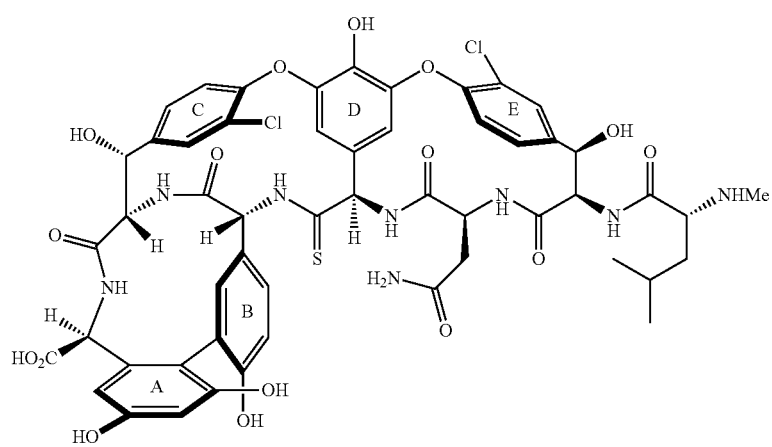

(IVA)

In antibiotic compositions of the invention with respect to amidine analogs of glycopeptides and their aglycones as disclosed and claimed herein which exhibit antibacterial activity versus vancomycin-resistant bacterial strains, the peptide sequence described above is present, but with a specific amide linkage modified to an amidine linkage, which confers upon the glycopeptide the desired additional antibacterial activity versus vancomycin-resistant bacterial strains. The amide bond so modified is the bond comprising the carboxyl group of the aminoacid residue bearing ring D in the glycopeptide antibiotics, as shown above, designated [Ψ-[C(=NH)NH]Tpg4] for vancomycin.

Accordingly, the invention provides, in various embodiments, D-ring amidine analogs of glycopeptide antibiotics, wherein the D-ring amidine analogs as defined in the present application are effective antibiotics versus resistant bacterial strains having the resistance-conferring alteration in common with that of the VanA and VanB strains. For example, the present invention provides, in various embodiments, D-ring amidine analogs of vancomycin, teicoplanin, balhimycin, actinoidin, ristocetin, and other glycopeptide comring itself can be bonded via aryl ether bonds to the C and E rings of other aminoacid residues in the core peptide of the glycopeptide antibiotic compounds, as discussed above. Consequently, the present invention provides in various embodiments a method for designing and preparing D ring aminoacid residue amidine analogs of glycopeptide antibiotics and their aglycone forms, and analogs, derivatives, and the like, comprising substituting an NH for an O in the carboxamido carbonyl group of the D ring aminoacid residue, providing the glycopeptide amide analog comprising the Ψ-peptide amidine core; furthermore the invention, in various embodiments, provides the glycopeptide pseudopeptide amidine analogs per se as novel and inventive structures.

The present invention, in various embodiments, discloses and claims herein the Ψ-amidine analogs of glycopeptide antibiotics vancomycin, teicoplanin, balhimycin, actinoidin, ristocetin, and their respective aglycones and analogs. These amidine pseudopeptide analogs of the glycopeptide antibiotics, aglycones, and analogs, exhibit antibiotic bioactivity versus bacterial strains that are resistant to vancomycin and related glycopeptides antibiotics.

The present invention, in various embodiments, discloses and claims herein the Ψ-thioamide analogs of glycopeptide antibiotics vancomycin, teicoplanin, balhimycin, actinoidin, ristocetin, and their respective aglycones and analogs. These thioamide pseudopeptide analogs of the glycopeptide antibiotics, aglycones, and analogs, can all be used with the silver ion catalyzed reaction with ammonia described in more detail below to produce the respective antibiotic amidine pseudopeptide analogs.

Specifically disclosed and claimed herein is an antibiotic glycopeptide-analogous compound for treatment of glycopeptide-resistant bacterial infections, comprising a pseudopeptide analog of a glycopeptide antibiotic or aglycone thereof, wherein the compound comprises a core pseudopeptide sequence having an amidine group that replaces a carboxamide linking group of a core peptide of the glycopeptide antibiotic or aglycone thereof, wherein a carboxamide O atom of a D ring-bearing aminoacid residue of the peptide core of the glycopeptide or aglycone has been replaced by an NH group, to provide a respective Ψ-amidine pseudopeptide analog of the glycopeptide antibiotic or aglycone.

More specifically, wherein the core peptide sequence of the glycopeptide or aglycone thereof can be aa-Phe'-aa-Phgly'-Phgly'-aa-Phe', wherein aa signifies an aminoacid residue, and Phe' and Phgly' signify modified phenylalanine and modified phenylglycine aminoacid residues respectively; wherein the carboxamide group that is replaced by the amidine group is disposed replacing the carboxamide group at the fourth peptide bond from the N-terminal aa group.

Or, the core peptide sequence is aa-Phe'-aa-Phgly'-Phgly'-Phgly'-Phe', wherein aa signifies an aminoacid residue, and Phe' and Phgly' respectively signify modified phenylalanine and modified phenylglycine aminoacid residues respectively; wherein the carboxamide group that is replaced by the amidine group is disposed replacing the carboxamide group at the fourth peptide bond from the N-terminal aa group.

Furthermore, for the above-recited compound, the aminoacid residue bearing the D ring can be a Phgly' aminoacid residue additionally coupled via aryl ether bonds to a C-ring of a Phe' aminoacid residue and to an E-ring of a Phe' aminoacid residue, wherein Phe' and Phgly' respectively signify modified phenylalanine and modified phenylglycine aminoacid residues respectively.

More specifically, the compound as disclosed and claimed herein can comprise a compound wherein the D ring aminoacid residue pseudopeptide amidine bond NH group, when complexed with a peptidoglycan bacterial cell wall precursor or model thereof comprising a D-Ala-D-Ala C-terminal dipeptide domain is hydrogen bonded in the complex to a peptide nitrogen atom of the D-Ala-D-Ala peptide bond.

For example, a vancomycin amidine analog (a pseudopeptide amidine analog) having antibiotic activity against vancomycin-resistant bacterial strains, is specifically disclosed and claimed herein, comprising a compound of formula (IA)

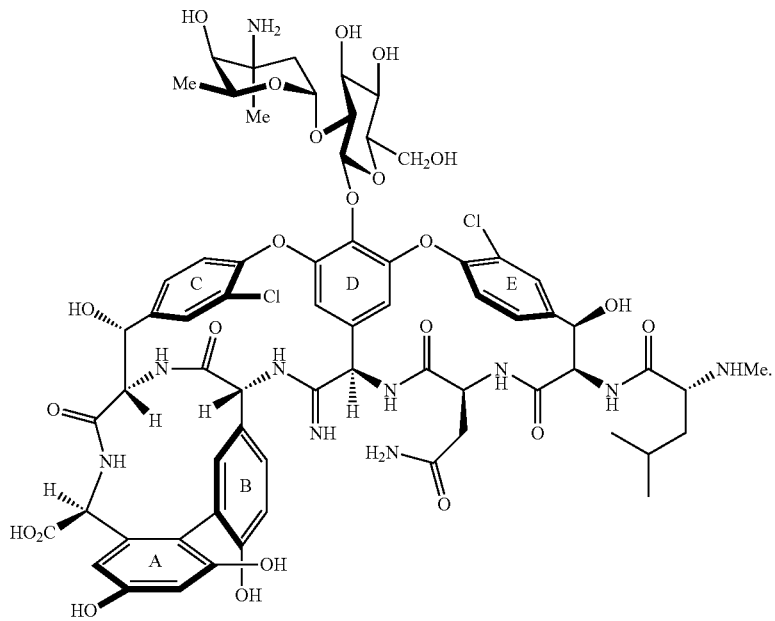

(IA)

To avoid ambiguity, the above structure is intended to depict the two phenolic bonds of the A and B rings, in the lower left hand corner as shown, in perspective not mutually bonded in any way; the biphenyl moiety of the A and B rings together is o, o', p'-trihydroxylated. The aromatic A, B, C, D, and E rings are identified in correspondence to the designations in the parent compounds, above.

Also specifically disclosed and claimed are C-terminal hydroxymethyl analogs also bearing the D-ring amidine modification, of formulas (IB) and (IC):

(IB)
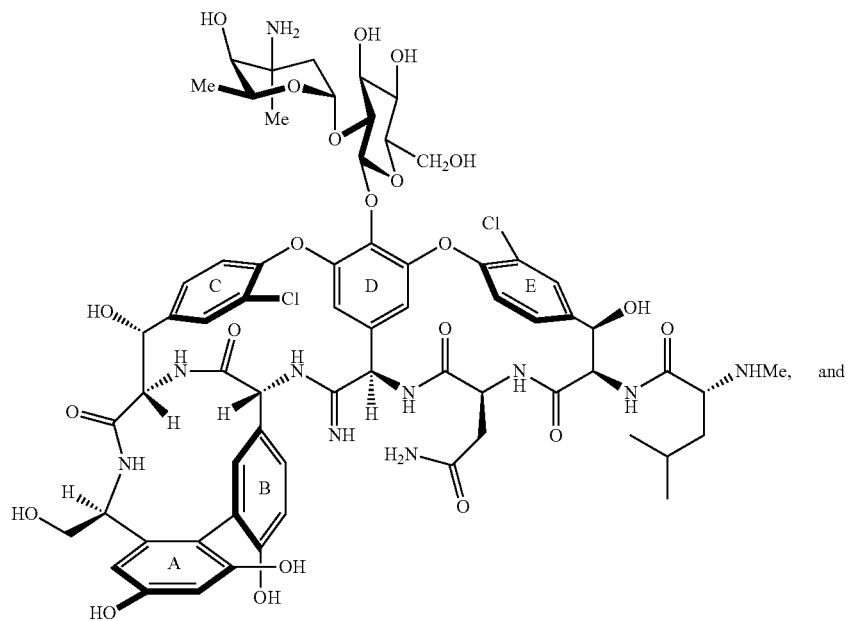
and
(IC)
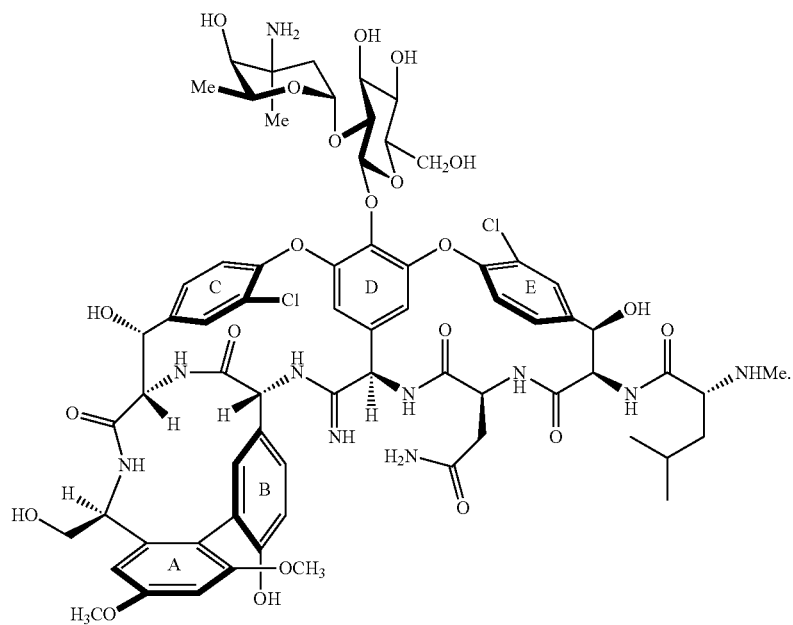

Also disclosed and claimed are an amidine analog of vancomycin aglycone of formula (IIA)
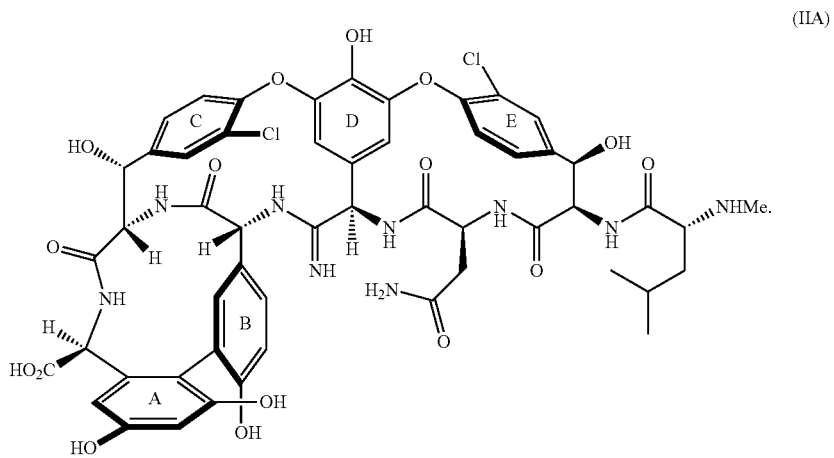
(IIA)
Also disclosed and claimed herein are aglycone analogs of formulas (IB) and (IC), above, namely C-terminal hydroxymethyl analogs of formula (IIB) and (IIC):
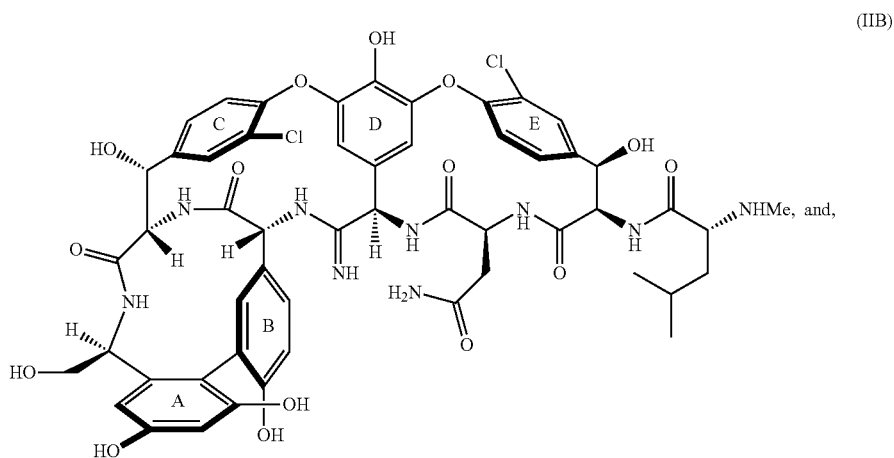
(IIB)
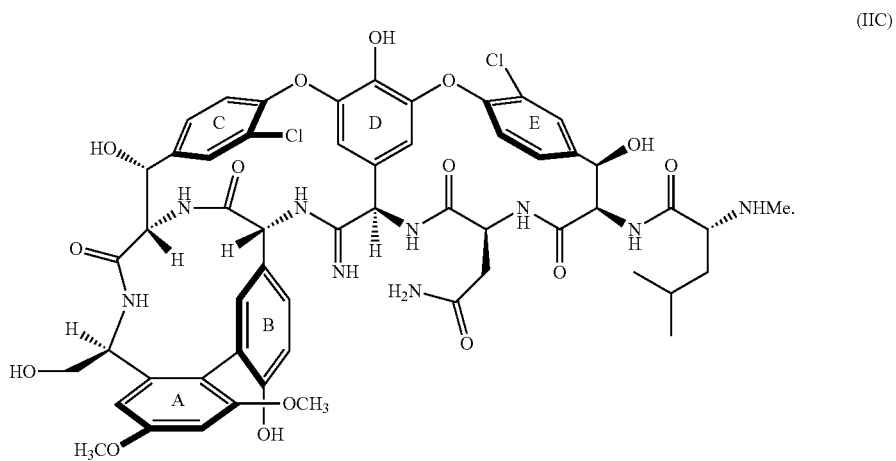
(IIC)

In other embodiments, the antibiotic pseudopeptide amidine glycopeptide analog can be a [Ψ[C(═NH)NH]Tpg⁴]-analog of vancomycin of formula (V)

(V)

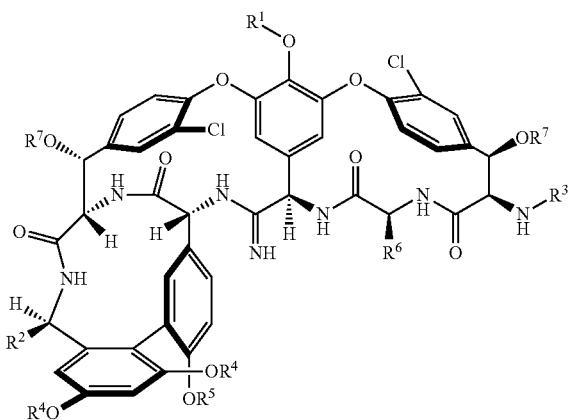

wherein

R¹ is H, or a glycosyl moiety;

R² is $CO_2R$, $CH_2OR$, or $CONR_2$, wherein R is H or ($C_1$-$C_6$)alkyl;

R³ is an aminoacyl group, optionally N-alkylated;

R⁴ at each occurrence is independently H, ($C_1$-$C_6$)alkyl, ($C_1$-$C_6$)alkanoyl, a glycosyl moiety;

R⁵ is H, ($C_1$-$C_6$)alkyl, or ($C_1$-$C_6$)alkanoyl;

R⁶ is group of formula, $(CR_2)$—$R^{6A}$, wherein $R^{6A}$ is aryl, $CO_2R$, $CONR_2$, ($C_1$-$C_6$)alkoxy, or ($C_1$-$C_6$)alkanoyl;

R⁷ at each occurrence is independently H, or a glycosyl moiety;

or a pharmaceutically acceptable salt thereof;

or a mixture thereof.

More specifically, the glycosyl moiety of R¹ can be of formula

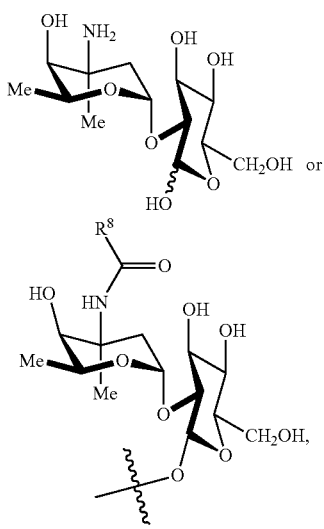

wherein R⁸ is alkyl, aryl, heterocyclyl, heteroaryl; a wavy line indicates a point of bonding;

or an epimer thereof or deoxy analog thereof. Alternatively, R⁸ can be directly bonded to the nitrogen atom without an intervening carbonyl group, providing an N-alkyl glycosyl unit.

Also disclosed and claimed herein is the structure (V) defined in the same way, but wherein the amidine NH group has been formally altered to an S atom, providing the thioamide analog (VT).

As is apparent, vancomycin Ψ-amidine pseudopeptide analogs contain an amidine pseudopeptide bond wherein a specific amide C═O group, as shown, is replaced by a C═NH group, forming an amidine linkage. Accordingly, the methyl-NH-Leu-Phe'-Asn-Phgly'-Phgly'-Phe'-Phgly'-CO₂H, core peptide unit of vancomycin has been modified to a core peptide unit wherein the amidine bond is present between two Phgly residues:

methyl-NH-Leu-Phe'-Asn-Phgly'-(C(═NH)—NH)-Phgly'-Phe'-Phgly'-CO₂H, wherein the modified amide group is on the carboxyl group of the D ring Phgly' that is tri-hydroxylated. For compounds of formulas (IB), (IC), (IIB), and (IIC), the peptide core is unchanged except for the modification of the C-terminal CO₂H group to a hydroxymethyl, CH₂OH group:

methyl-NH-Leu-Phe'-Asn-Phgly'-(C(═NH)—NH)-Phgly'-Phe'-Phgly'-CH₂OH.

For vancomycin and its aglycone, this modification is termed a [Ψ-[C(═NH)NH]Tpg⁴] modification; as previously described, the amidine group replaces the carboxamide group of the fourth peptide bond counting from the N-terminus of the peptide core. For the other glycopeptide antibiotics shown above, this modification of the corresponding peptide bond can also be termed [Ψ-[C(═NH)NH]Tpg⁴], as in all the exemplary cases, this is the fourth peptide bond from the N-terminus in all those compounds, but other glycopeptides can have different nomenclature. Nevertheless, the key structural feature that fixes the position of the carbonyl group modified to amidine, thioamide, etc., is the D-ring as defined above, the carboxamido carbonyl group of which is hydrogen bonded to the NH group of the penultimate amide bond in the D-Ala-D-Ala cell wall precursor peptideglycan. Replacing this oxygen atom with an NH group provides a glycopeptide antibiotic pseudopeptide analog that is effective versus bacterial strains wherein the D-Ala-D-Ala domain has mutated to a D-Ala-D-Lac domain, as well as versus wild type strains, by maintaining hydrogen bonding with either NH or O atom in the same position of the peptidoglycin C-terminal dipeptide domain.

The altered cell wall precursor structure containing the D-Ala-D-Lac glycopeptide antibiotic-resistant phenotype, which does not bind vancomycin with high enough affinity for vancomycin to have antibiotic activity at therapeutically achievable concentrations, are bound sufficiently by the amidine analogs of glycopeptide antibiotics, e.g., vancomycin and its aglycone, provided the amidine group is correctly located within the glycopeptide molecule. The same interactions that confer bioactivity versus vancomycin-resistant bacterial strains for the amidine-modified vancomycin aglycone as discussed in detail herein, are the same interactions that provide the insight that amidine-modified glycopeptide antibiotics of other structures will be effective against bacterial strains where an analogous D-Ala-D-Ala to D-Ala-D-Lac alteration provides resistance to the wild type antibiotic.

Following an initial success with [Ψ-[CH₂NH]Tpg⁴]vancomycin aglycon[24] to achieve this dual binding by the removal of the lone pair repulsion between the vancomycin residue 4 carbonyl and D-Ala-D-Lac ester oxygens,[13] we report [Ψ-[C(═NH)NH]-Tpg⁴]vancomycin aglycon (IIA)[25]

in a search for improved dual binding affinities and antimicrobial activities. Amidine (IIA) displayed effective, balanced binding affinity for both model ligands at a level that is within 2- to 3-fold that exhibited by vancomycin aglycon for D-Ala-D-Ala. Accurately reflecting these binding properties, (IIA) exhibited potent antimicrobial activity (MIC=0.31 μg/mL, VanA E. faecalis) against VRE, being equipotent to the activity that vancomycin displays against sensitive bacterial strains. Although this represents a single atom exchange in the antibiotic (O→NH) to counter a corresponding single atom exchange in the cell wall precursors of resistant bacteria (NH→O), the modified antibiotic also maintains vancomycin's ability to bind the unaltered peptidoglycan D-Ala-D-Ala by virtue of its apparent ability to serve as either a H-bond donor (for D-Ala-D-Lac) or H-bond acceptor (for D-Ala-D-Ala). Whereas the former entails binding of the expectedly protonated amidine ($pK_a$=12.5), the latter requires binding of the unprotonated amidine. See Scheme 1, below.

Scheme 1: Hydrogen Bonding Donor/Acceptor Configurations for Mutant and Wild Type

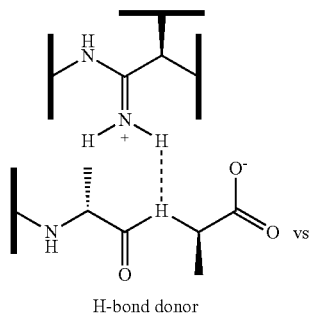

H-bond donor

H-bond acceptor

Preparation of Compounds of the Invention

Despite all the modifications that have historically been made to vancomycin, analogues bearing alterations to the core structure, including changes to the critical binding pocket region itself, have been essentially unexplored. With the structural complexity of glycopeptides, initial modification to the peptide backbone was most accessible through total synthesis. Our efforts on the total synthesis of glycopeptide antibiotics, which first provided the vancomycin aglycon,[16] and were subsequently extended to provide the teicoplanin[26-27] and ristocetin[28] aglycons and the complestatins[29,30,31] provided us a unique opportunity to explore such deep-seated modifications of the natural products.

We designed a divergent total synthesis that would proceed through a key intermediate that allows a late-stage diversification into a series of analogues.[34] The strategy in structural terms replaced the residue-4 carboxamide of vancomycin aglycone with the corresponding thioamide (IVA), which could then be selectively modified at a late stage in the presence of the other multiple amides (peptide bonds), e.g., to prepare the amidine analog (IIA). After a screen of potential stages at which to incorporate the thioamide, we found the most efficient reaction was that performed on an early stage precursor using Lawesson's reagent, which proceeded with complete selectively for the sterically more accessible of two possible amides. From this initial thionation stage, a multistep total synthesis was elaborated resulting in the preparation of [Ψ-[C(=(=S)NH]Tpg4]vancomycin aglycone,[25] see Scheme 2, below.

Scheme 2: Synthetic Approaches to [Ψ-[C(=S)NH]Tpg4] vancomycin aglycon

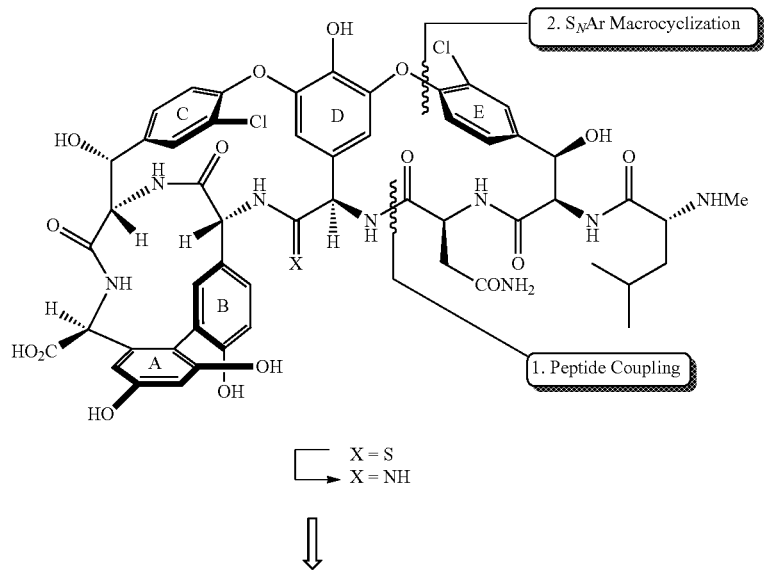

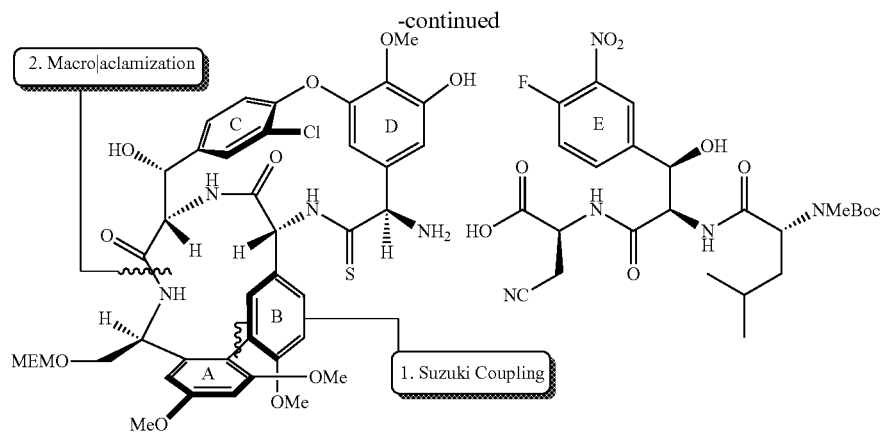

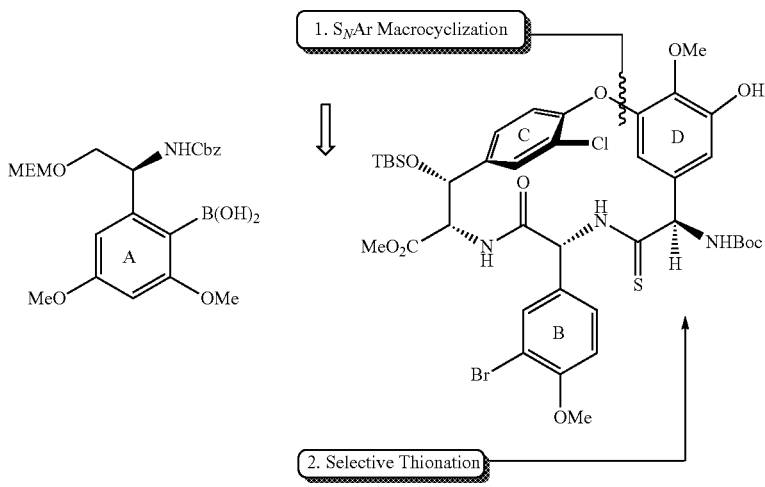

In addition to early stage residue-4 thioamide introduction, allowing differentiation of one of seven amide bonds central to the vancomycin core structure, the approach relied on two aromatic nucleophilic substitution reactions for formation of the 16-membered diaryl ethers in the CD/DE ring systems, an effective macrolactamization for closure of the 12-membered biaryl AB ring system, and the defined order of CD, AB, and DE ring closures. This order of ring closures follows their ease of thermal atropisomer equilibration, permitting the recycling of any newly generated unnatural atropisomer under progressively milder thermal conditions where the atropoisomer stereochemistry already set is not impacted. Notably, the same ABCD ring system thioamide shown above and used to prepare [Ψ[C(=S)NH]Tpg$^4$]-vancomycin aglycone can be used to also prepare [Ψ[C(=S)NH]Tpg$^4$]-teicoplanin aglycone, [Ψ[C(=S)NH]Tpg$^4$]-Fristocitin A aglycone and [Ψ[C(=S)NH]Tpg$^4$]-actinoidin A aglycone following a synthetic route and protocols we introduced for the teicoplanin and ristocetin aglycones themselves,[17,18] and easily extended to actinoidin A, This vancomycin residue-4 thioamide ([Ψ-[C(=S)NH]Tpg$^4$]-vancomycin aglycone) displayed revealing properties in its own right. The single atom substitution of sulfur for oxygen was sufficient to completely disrupt binding to both D-Ala-D-Ala and D-Ala-D-Lac and the compound lacked any antimicrobial activity, FIG. 3. Although the weaker H-bonding of a thioamide is likely contributing to this lowered affinity for D-Ala-D-Ala, the magnitude of the loss suggests a more fundamental steric displacement, due to the thiocarbonyl increased bond length and larger van der Waals radii of sulfur, is responsible. In addition to the sharp contrast this provides to the corresponding residue-4 amidine ([Ψ[C(=NH)]Tpg$^4$]-vancomycin aglycone), illustrating the near perfect isosteric amidine replacement for an amide, the inactivity of the residue 4 thioamide defines a key intermediate to be targeted with producing non-pathogenic micoorganisms that avoids the otherwise suicidal production of the amidine itself. Thus, the properties of the residue-4 thioamides, which might appear disappointing on the surface, represent an important key observation made in our efforts that will serve to advance the field.

Accordingly, the invention provides a vancomycin [Ψ[C(=)NH]Tpg$^4$]-thioamide analog of formula (IIIA)
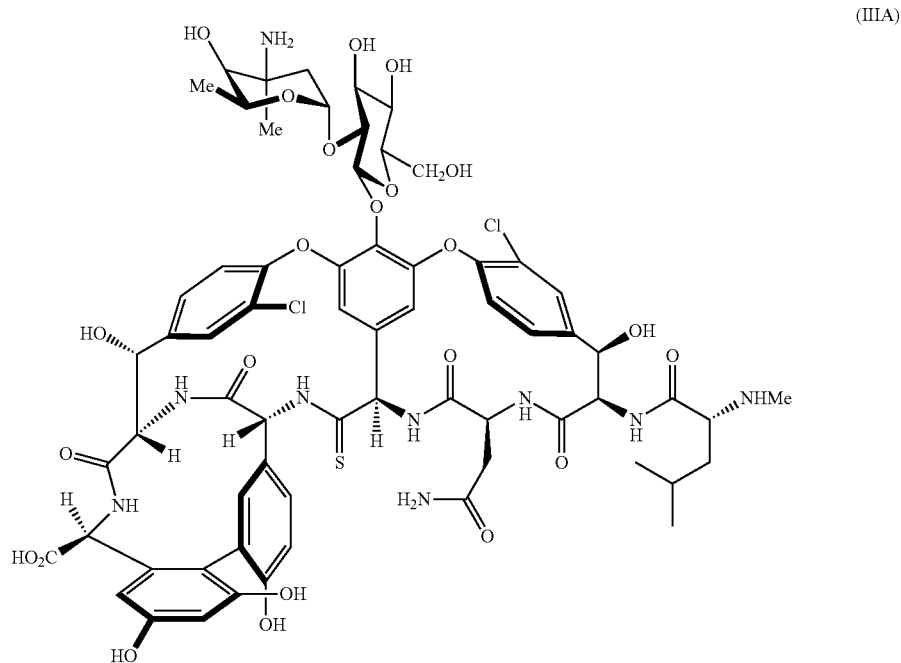
(IIIB)
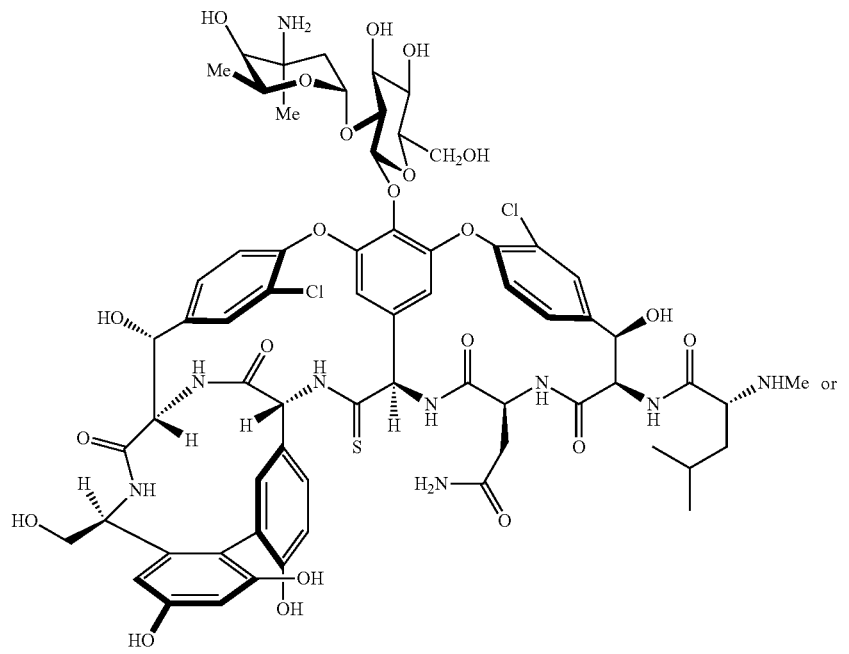
or

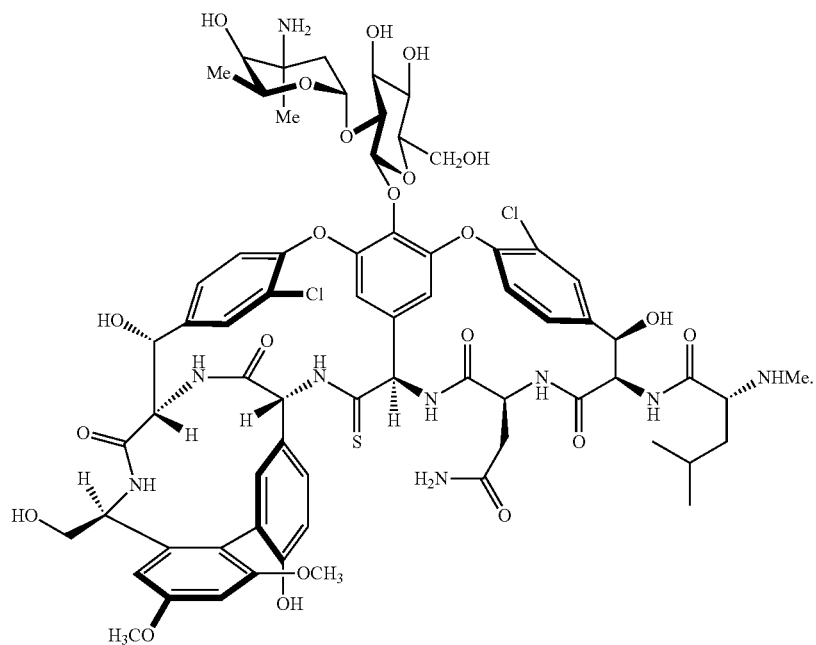
(IIIC)
Also, the invention provides a vancomycin aglycone [Ψ[C(=S)NH]Tpg⁴]-thioamide analog of formula
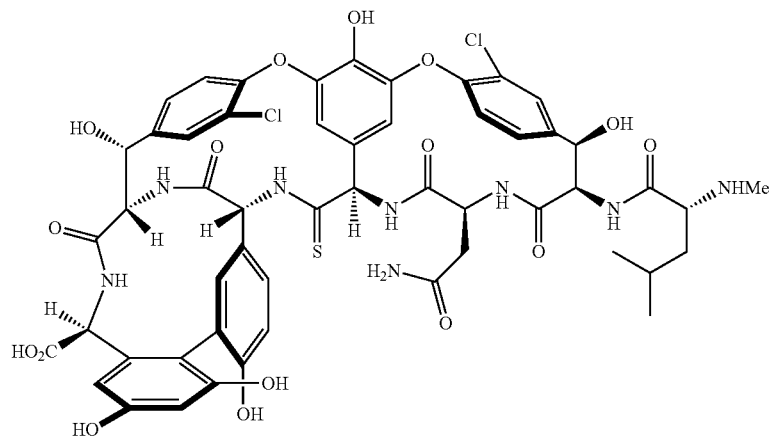
(IVA)
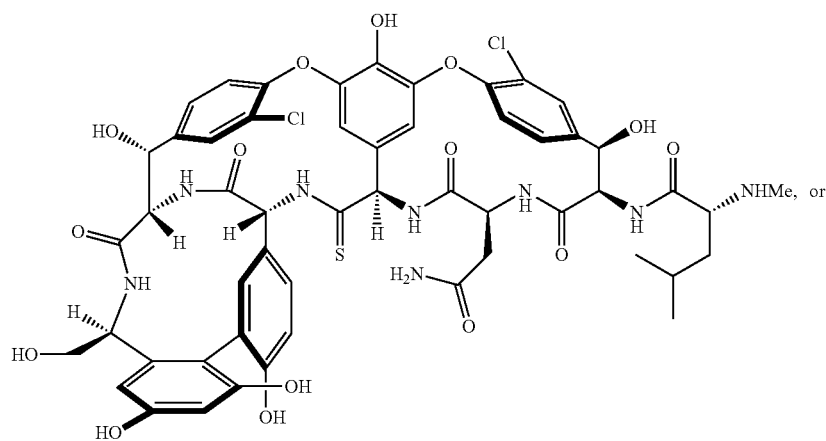
(IVB)

(IVC)

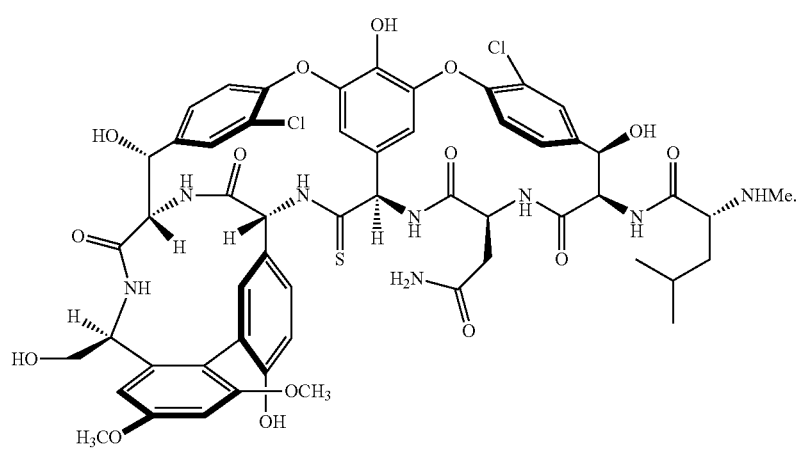

It is within ordinary skill, using the disclosure herein, and in conjunction with the disclosures of documents cited and incorporated by reference herein for the preparation of other members of the glycopeptide antibiotic class including teicoplanin and the other listed above, to prepare synthetically a corresponding thioamide analog wherein the thioamide group selectively substitutes for the carboxamide peptide bond of the D ring-bearing aminoacid residue of other glycopeptide antibiotics. See, for example, the following publications, which in conjunction with the synthetic work by the present inventor listed in the Documents Cited section, and with ordinary knowledge and skill, are sufficient to guide the preparation of thioamides of glycopeptide antibiotics in general without undue experimentation:

Kahne, D., Leimkuhler, C., Lu, W., and Walsh, C. T. (2005) Glycopeptide and lipoglycopeptide antibiotics. *Chem. Rev.* 105, 425-448.

*Glycopeptide Antibiotics*; Nagarajan, R., Ed.; Marcel Dekker: New York, 1994.

Malabarba, A.; Nicas, T. I.; Thompson, R. C. *Med. Res. Rev.* 1997, 17, 69.

Malabarba, A.; Ciabatti, R. *Curr. Med. Chem.* 2001, 8, 1759.

Van Bambeke, F. V.; Laethem, Y. V.; Courvalin, P.; Tulkens, P. M. *Drugs* 2004, 64, 913.

With the availability of [ΨΨ-[C(=S)NH]Tpg4]vancomycin aglycon, the stage was set to develop the site-specific single-step introduction of key modifications at a site critical to the interaction between vancomycin and the peptidoglycan terminus. Although the methylene derivative (i.e., [Ψ-[CH$_2$NH]Tpg4]vancomycin aglycon) exhibited the desired dual binding properties, we sought to design and explore analogues that could further enhance D-Ala-D-Lac binding while simultaneously maintaining binding for D-Ala-D-Ala. We turned our focus to [Ψ[C(=NH)NH]Tpg4]vancomycin aglycon, wherein the residue-4 amide of vancomycin is replaced with an amidine. The residue-4 thioamide was selectively converted to the corresponding amidine in a single step using a unique, previously unexplored AgOAc-promoted reaction that could be conducted on a fully deprotected and fully elaborated vancomycin aglycon,[25] Scheme 3.

Scheme 3: Conversion of Thioamide (IVA) to Amidine (IIA)

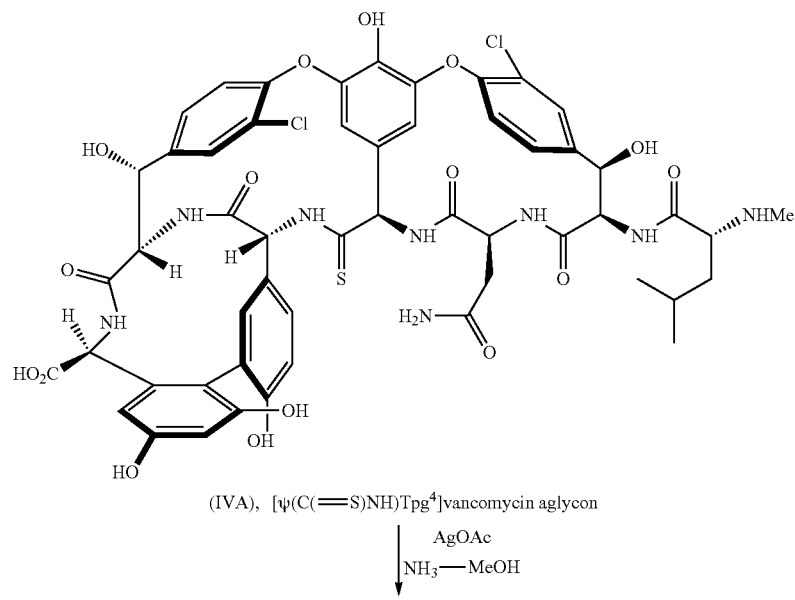

(IVA), [ψ(C(=S)NH)Tpg$^4$]vancomycin aglycon

AgOAc

NH$_3$—MeOH

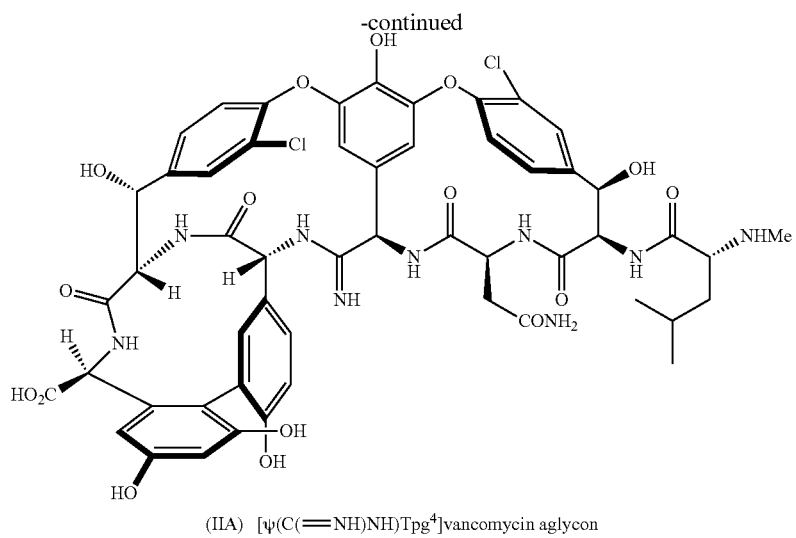

(IIA) [ψ(C(=NH)NH)Tpg⁴]vancomycin aglycon

Treatment of the fully deprotected vancomycin aglycon thioamide (IVA), prepared by a total synthesis modeled on our preceding work,[16-19] with silver acetate (AgOAc, 10 equiv) in methanol saturated with ammonia (NH$_3$-MeOH) at 25.degree. C. (12 h) directly provided the amidine (IIA) cleanly as a colorless solid that is stable to extensive handling. It is readily soluble in water (H$_2$O) or H$_2$O-MeOH, but insoluble in acetonitrile (MeCN), and it required addition of trifluoroacetic acid (TFA) to the sample before reverse-phase high-performance liquid chromatography (HPLC) purification.

It was then undertaken to explore the use of the residue-4 thioamide as a precursor for other glycopeptide pseudopeptide analogs that could potentially overcome bacterial resistance. In addition to the NH amidine, the preparation of the N-methyl amidine, the N-hydroxyamidine (amidoxime), the N-aminoamidine (amidrazone) and the N-cyanoamidine.

Because of the magnitude of the effort involved, the survey herein was conducted on the advanced synthetic intermediate (IVB) bearing the residue-4 thioamide, but a C-terminus hydroxymethyl group in place of the carboxylic acid. This intermediate is available in 22 versus 26 steps and its derivatives, including the amidine (IIB), exhibit binding and in vitro antimicrobial properties indistinguishable from the corresponding vancomycin aglycon derivatives.[25b]

The first of the substituted amidines that we were especially interested in targeting was the N-methylamidine 11. Unexpectedly, efforts to convert thioamide 9 (i.e., (IVB)) to 11 using AgOAc and MeNH$_2$-MeOH under the reaction conditions used to prepare 4 and 10 were not successful. As a result, the various parameters of this reaction were examined first using a model series starting with the simpler thioamide substrate 15 (Table 1).[32,33]

Like the reaction with 9, attempts to convert 15 to 17 using MeNH$_2$ (2 M in MeOH) and AgOAc (2-10 equiv) in MeOH were not especially successful. More surprisingly, we also found that AgOAc (3 equiv) in NH$_3$-MeOH was not as effective in converting 15 to the parent amidine 16 although 15 is rapidly consumed. In MeOH and in the absence of a reacting amine, treatment of 15 with AgOAc (3 equiv) rapidly provides the corresponding O-methylimidate (>90%). However, subsequent treatment of the in situ generated O-methylimidate with NH$_3$ (7 M in MeOH) fails to provide 16, indicating that it is not an intermediate enroute to the amidine.

Figure 4:
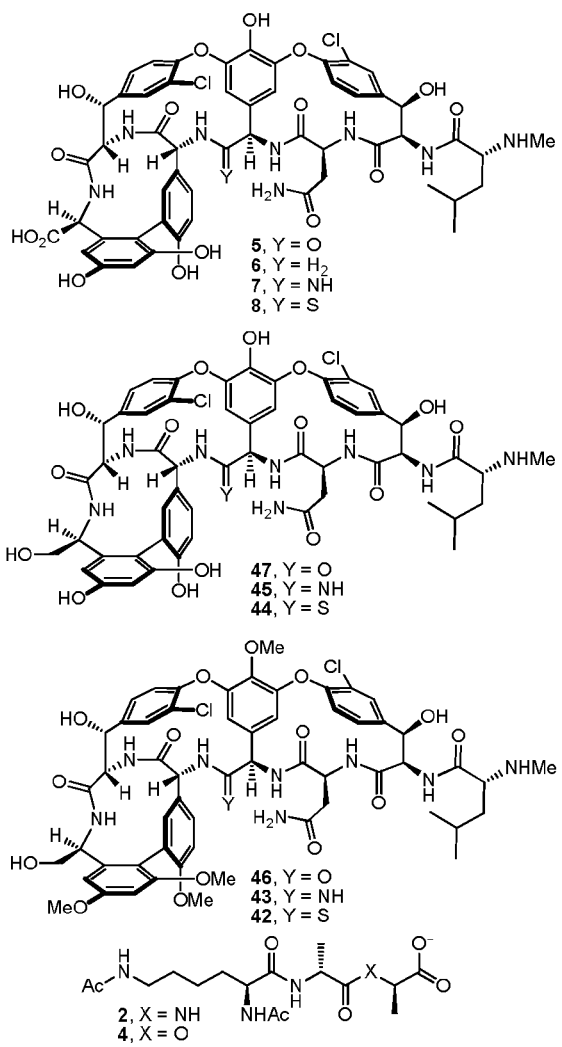
FIG. 4 shows additional structures and biodata for compounds and methods of the invention.

A series of alternative Ag(I) salts were examined. These studies revealed that the more reactive Ag(I) salts including AgBF$_4$ and AgOCOCF$_3$ were effective at promoting the conversion of 15 to the parent amidine 16 (83%), the N-methylamidine 17 (93%, 1:1 E:Z), or the N,N-dimethylamidine 18 (82%) in good yields in MeOH at room temperature (FIG. 4). Moreover, these conditions were successful in converting the residue 4 thioamide in 9 to the N-methylamidine 11 as an inseparable or equilibrating 1:1 mixture of E:Z isomers (5 equiv AgBF$_4$, 2 M MeNH$_2$ in MeOH, 25° C., 30 min), Table 1.

TABLE 1

Conversion of Model Thioamide to Amidines with Silver Ion Catalysis

| Ag salt | time | % yield |
|---|---|---|
| AgOAc | 1-24 h | 30-32% |
| AgNO$_3$ | 10 min | 0% |
| AgBr | 2 h | 0% |
| Ag$_2$CO$_3$ | 10 min | 0% |
| AgO | 2 h | 0% |
| AgOTf | 3 h | 49% |
| AgSbF$_6$ | 5 min | 65% |
| AgOCOCF$_3$ | 10 min | 70% |
| AgBF$_4$ | 2 h | 83% |

TABLE 1-continued

Conversion of Model Thioamide to Amidines with Silver Ion Catalysis

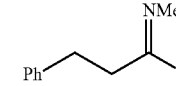

| Ag salt | time | % yield |
|---|---|---|
| AgOAc (5 equiv) | 24 h | <35% (1:1) |
| AgBF$_4$ (3 equiv) | 3 h | 93% (1:1) |
| HgCl$_2$ | 12 h (THF) | 79% (1:1) |
| AgOAc (5 equiv) | 24 h | 16% |
| AgBF$_4$ (5 equiv) | 3 h | 44-57% |
| AgBF$_4$ (5 equiv)$^a$ | 3 h | 82% |

$^a$With Et$_3$N (10 equiv)

Extension of the methodology to the preparation of the N-hydroxyamidine (amidoxime) 19 upon reaction of 15 with hydroxylamine is summarized in Table 2. AgOAc proved modestly effective at promoting formation of 19 in MeOH, whereas the more reactive Ag(I) salts resulted in further reaction of the product amidoxime 19, leading to liberation of the N-hydroxyamidoxime and thioamide cleavage. This cleavage reaction of thioamide 15 was suppressed by running the reaction in less polar and aprotic solvents where 19 was isolated in excellent yields. Generation of 12, requiring the use of a protic solvent (MeOH), provided the easily handled residue 4 amidoxime as a single E-isomer.

Similar observations were made in the preparation of the Boc protected N-aminoamidine (amidrazone) 20 upon reaction of 15 with BocNHNH$_2$ (Table 2). Due to the high nucleophilicity of BocNHNH$_2$, most Ag(I)-promoted reactions led to double addition and cleavage of the thioamide. Short reaction times (5 min) with AgBF$_4$ (5 equiv) and limiting the amount of BocNHNH$_2$ (2 equiv, MeOH, 73%) or the use of aprotic, nonpolar solvents suppressed the overreaction and provided 20 in good yields. Such problems were less significant with 9, where the residue 4 thioamide is sterically hindered. The well behaved Boc protected precursor to the amidrazone 13 was isolated in good yield as a single isomer.

TABLE 2

Conversion of Model Thioamide to Amidoxime and Amidrazone

| Ag salt (equiv) | $^a$HONH$_2$ (equiv) | time | solvent | % yield |
|---|---|---|---|---|
| AgOAc (3) | 10 | 12 h | MeOH | 36% (61:1) |
| AgBF$_4$ (3) | 10 | 2 h | MeOH | 0% |
| AgBF$_4$ (5) | 100 | 3 h | THF | 78% (−) |
| AgBF$_4$ (3) | 10 | 2 h | CH$_3$CN | 87% (18:1) |

$^a$NH$_2$OH (aq. 50% w/w)

| Ag salt | BocNHNH$_2$ (equiv) | time | solvent | % yield |
|---|---|---|---|---|
| AgBF$_4$ | 30 | 5 min | MeOH | <30% |
| AgBF$_4$ | 30$^a$ | 5 min | THF | <20% |
| AgBF$_4$ | 30$^b$ | 5 min | THF | 51% (ca. 1:1) |
| AgBF$_4$ | 2$^b$ | 5 min | THF | 55% (ca. 1:1) |
| AgBF$_4$ | 2$^b$ | 5 min | MeOH | 73% (ca. 1:1) |

$^a$With Et$_3$N (10 equiv).
$^b$With NaHCO$_3$ (10 equiv).

The amine anticipated to be most challenging was cyanamide, due to its lower nucleophilicity (Table 3). Remarkably, use of AgOAc (5 equiv) in MeOH led to rapid conversion of 15 to N-cyanoamidine 21 (30 equiv H$_2$NCN, 10 min; 85%). Extending this reaction to the preparation of the vancomycin aglycon N-cyanoamidine using AgOAc (5 equiv) provided 14 as a single isomer whose properties were consistent with the Z-configuration or equilibration to (Z)-14 under the assay conditions. The conversion of the thioamide 15 to the N-cyanoamidine 21 could also be conducted in aprotic solvents (THF>CH$_3$CN>DMF). The further inclusion of Et$_3$N (10 equiv) gave rise to a reaction that was complete in minutes and provided superb yields of 21 (91-94%).

Figure 3:
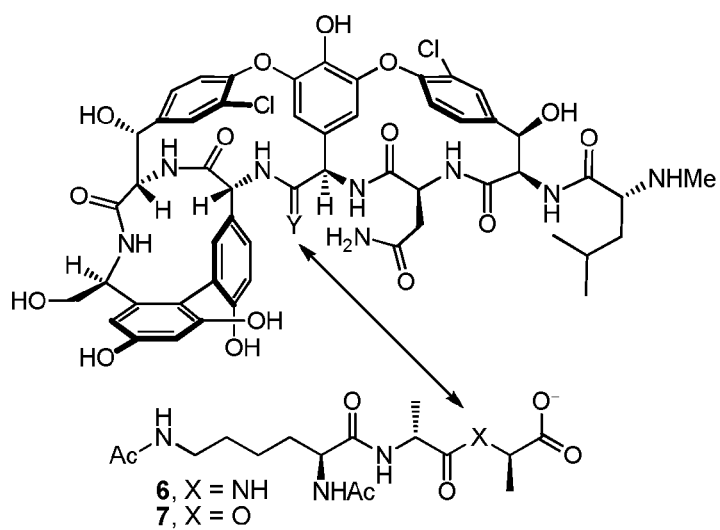
FIG. 3 shows a schematic and a bioactivity table of various vancomycin aglycone analogs.

The results of the examination of the amidines 11-14 are summarized in FIG. 3. N-Methylamidine 11 proved to be 30 to 50 times less effective than the parent amidine 10 at binding[23] the model D-Ala-D-Ala and D-Ala-D-Lac ligands 6 and 7, respectively, but 11 bound both with near equal affinities. Accordingly, it was found to be active against VanA VRE (MIC=20 μg/mL), albeit being 60-fold less potent than 10 precisely in line with its relative binding characteristics.

TABLE 3

Conversion of Model Thioamide to N-Cyanoamidine

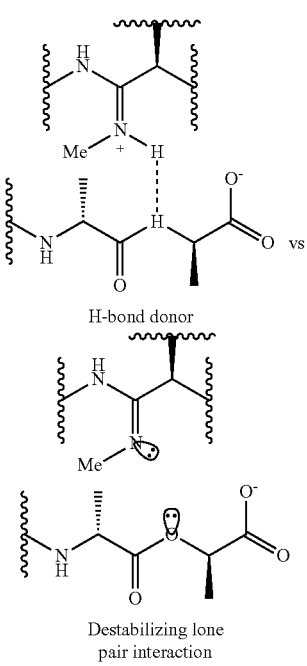

| Ag salt (equiv) | NH$_2$CN (equiv) | time | solvent | % yield |
|---|---|---|---|---|
| AgOAc (5) | 30 | 10 min | MeOH | 85% (3:1) |
| AgOAc (5) | 30 | 10 min | MeOH | 93%[a] (1:110) |
| AgOAc (5) | 30 | 10 min | DMF | 71%[a] (1:6) |
| AgBF$_4$ (5) | 30 | 30 min | CH$_3$CN | 91%[b] (1:40) |
| AgBF$_4$ (5) | 30 | 10 min | THF | 94%[b] (1:30) |

[a] With NaHCO$_3$ (10 equiv).
[b] With Et$_3$N (10 equiv).

Although the assessment was conducted with a sample composed of either an inseparable or equilibrating 1:1 mixture of E:Z isomers, the results still indicate that the substitution of the amidine with a small methyl group is sufficient to significantly diminish its binding and antimicrobial properties. Whereas it is difficult to infer details about the protonation state of an amidine when binding D-Ala-D-Ala, the comparison of 11 with 10 support expectations that it must be the protonated amidine that binds D-Ala-D-Lac. Unlike 10, the unprotonated state of 11 would be incapable of H-bonding to the ligand and suffers a further destabilizing lone pair/lone pair interaction, as shown below.

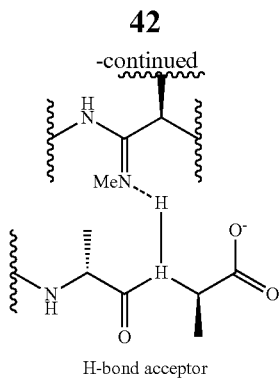

H-bond acceptor

The behavior of N-cyanoamidine 14, which cannot be protonated (pK$_a$=1), proved even more interesting. Although its affinities and activity were reduced relative to the amide 8, the relative behavior of 8 and 14 was identical and distinct from those of the amidines 10 and 11 (FIG. 3). Like the amide 8, N-cyanoamidine 14 bound D-Ala-D-Ala much more effectively than D-Ala-D-Lac, which it failed to bind (≥120-fold). Accordingly, 14 lacked antimicrobial activity against VanA VRE (MIC>40 µg/mL), but remained active against vancomycin-sensitive *S. aureus* (MIC=10 µg/mL) at a level consistent with its affinity for D-Ala-D-Ala. Moreover, this affinity for D-Ala-D-Ala was found to be roughly equivalent to that of N-methylamidine 11, albeit 20-fold less than the parent amide 8 or amidine 10. The inability of the unprotonated amidine 14 to bind D-Ala-D-Lac confirms that the effective D-Ala-D-Lac binding of the parent amidine 10 and N-methylamidine 11 must entail binding of the protonated amidines, replacing the destabilizing lone pair repulsion with a stabilizing electrostatic interaction and weak reverse H-bond. Similarly, the comparable binding affinities of the unprotonated cyanoamidine 14 and the N-methylamidine 11 with D-Ala-D-Ala indicate both bind in their unprotonated state, accepting a H-bond from the linking amide in the bound ligand, as shown below.

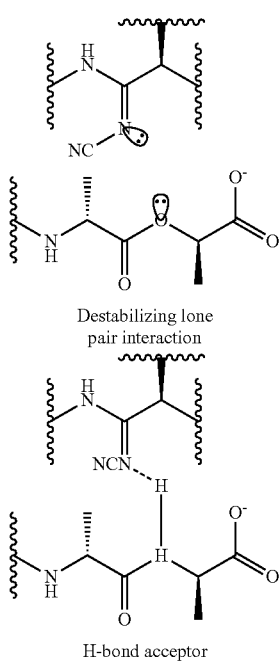

Destabilizing lone pair interaction

H-bond acceptor

Biological Evaluation

The results of the examination of 6 are summarized in FIG. 3 alongside those of vancomycin aglycon (5) and the synthetic methylene derivative 7,[24] lacking the amide carbonyl. Both the C=N bond length of an amidine (1.30 vs 1.23 Å) and the van der Waals radii of nitrogen (1.55 vs 1.52 Å) closely approximate those of an amide carbonyl and oxygen atom, suggesting that an amidine may serve geometrically and sterically as an effective amide isostere. The binding affinity[30] of 6 with the model D-Ala-D-Ala ligand 2 was found to be only approximately 2-fold less than the vancomycin aglycon itself and 15-fold greater than the methylene derivative 7, suggesting that the amidine functions well as a H-bond acceptor for the amide NH in the model ligand. Moreover, this binding affinity of 6 was maintained with the model D-Ala-D-Lac ligand 4, representing a nearly 600-fold increase in affinity relative to the vancomycin aglycon (5) and a more than 10-fold increase relative to the methylene derivative 7. Importantly, 6 displays effective, balanced binding affinity for both model ligands ($K_a$ 2/4=1.05) at a level that is within 2-3 fold that exhibited by vancomycin aglycon (5) for D-Ala-D-Ala. Accurately reflecting these binding properties, 6 exhibited potent antimicrobial activity (MIC=0.31 µg/mL) against VanA resistant *E. faecalis* (VanA VRE, BM4166), the most stringent of vancomycin-resistant bacteria, being equipotent to the activity that vancomycin (1) and vancomycin aglycon (5) display against sensitive bacterial strains (MIC=0.3-2 µg/mL).

*E. faecalis* (BM4166) was propagated and MIC's were determined in duplicate by the broth microdilution method according to standard microbiological practice. See: Clinical and Laboratory Standards Institute. *Methods for Dilution Antimicrobial Susceptibility Tests for Bacteria That Grow Aerobically*; Approved Standard, 7th ed.; CLSI document M07-A8; Clinical and Laboratory Standards Institute: Wayne, Pa., 2009. Cudic, M.; Condie, B. A.; Weiner, D. J.; Lysenko, E. S.; Xiang, Z. Q.; Insug, O.; Bulet, P.; Otvos, L., Jr.; *Peptides* 2002, 23, 271.

[Ψ[C(=S)NH]Tpg⁴]Vancomycin Aglycon (8).

White film; $^1$H NMR (CD$_3$OD, 600 MHz) δ 7.65 (br s, 3H), 7.59 (d, J=12 Hz, 1H), 7.37 (br s, 1H), 7.28 (d, J=6.0 Hz, 1H), 7.21 (br s, 1H), 6.75 (d, J=6 Hz, 1H), 6.44 (s, 1H), 6.39 (s, 1H), 6.12 (br s, 1H), 5.82 (br s, 1H), 5.41-5.24 (m, 4H), 4.85-4.70 (m, 3H, obscured by D$_2$O), 4.42 (d, J=12 Hz, 1H), 4.27 (s, 1H), 4.05-3.97 (m, 1H), 3.03 (d, J=6 Hz, 1H), 2.77 (s, 3H), 2.22-2.17 (m, 1H), 1.91-1.93 (m, 1H), 1.74-1.64 (m, 1H), 1.64-1.56 (m, 1H), 0.99-0.89 (m, 6H); ESI-TOF HRMS m/z 1159.2710 (M$^+$+H, C$_{53}$H$_{53}$Cl$_2$N$_8$O$_{16}$S requires 1159.2672).

[Ψ[C(=NH)NH]Tpg⁴]Vancomycin Aglycon (6).

A solution of 8 (0.46 mg, 0.40 µmol) in anhydrous methanol saturated with ammonia (0.5 mL) was treated with silver acetate (AgOAc, 0.70 mg, 4.2 µmol, 10 equiv). The reaction mixture was stirred at room temperature for 12 h before the solvent was removed under a stream of N$_3$. The residue was dissolved in 30% CH$_3$OH in water (0.4 mL+10 µL TFA) and purified by semi-preparative reverse-phase HPLC (CH$_3$OH/H$_2$O-0.07% TFA 30:70, 3 mL/min, R$_t$=17.9 min) to afford 6 as a white film: $^1$H NMR (CD$_3$OD, 600 MHz) δ 7.73-7.64 (m, 2H), 7.61-7.52 (br m, 1H), 7.41 (br s, 1H), 7.12 (d, J=6 Hz, 1H), 7.08-7.02 (m, 2H), 6.87 (d, J=12 Hz, 1H), 6.49-6.42 (m, 2H), 6.16-6.04 (br m, 1H), 5.53 (br s, 1H), 5.47-5.29 (m, 4H), 4.75-4.50 (m, 3H, obscured by D$_2$O), 4.31-4.24 (m, 1H), 4.22-4.12 (m, 1H), 4.11-4.05 (m, 1H), 2.85 (s, 3H), 2.85-2.81 (m, 1H), 2.45-2.37 (m, 1H), 1.85-1.75 (m, 1H), 1.64-1.54 (m, 2H), 0.94-0.79 (m, 6H); MALDI-TOF m/z 1142.3 (M$^+$+H, C$_{53}$H$_{54}$Cl$_2$N$_9$O$_{16}$ requires 1142.3); ESI-TOF HRMS m/z 1142.3077 (M$^+$+H, C$_{53}$H$_{54}$Cl$_2$N$_9$O$_{16}$ requires 1142.3066).

Titration Binding Assays with Model D-Ala-D-Ala and D-Ala-D-Lac Ligands 2 and 4.

The binding constants for compounds 6 and 8 for association with the model ligands N,N'-Ac$_2$-Lys-D-Ala-D-Ala (2) and N,N'-Ac$_2$-Lys-D-Ala-D-Lac (4) were determined according to literature protocol.[30] UV difference measurements were carried out on a CARY 3E UV-Vis spectrometer. UV scans were run with a baseline correction that consisted of 0.02 M sodium citrate buffer (pH=5.1) and covered the range from 200 to 345 nm. A solution of 6 or 8 (7.7×10$^{-5}$ M in 0.02 M sodium citrate buffer) was placed into a quartz UV cuvette (0.1 cm path length) and the UV spectrum recorded versus a reference cell containing 0.02 M sodium citrate buffer. UV spectra were recorded after each addition of a solution of N,N'-Ac$_2$-Lys-D-Ala-D-Ala (2) or N,N'-Ac$_2$-Lys-D-Ala-D-Lac (4) in 0.02 M sodium citrate buffer to each cell from 0.1 to 60.0 equivalents. The absorbance value at the λ$_{max}$ was recorded and the running change in absorbance, ΔA$_{x\ equiv}$ (A$_{initial}$-A$_{x\ equiv}$), measured. The number of ligand equivalents was plotted versus ΔA to afford the ligand binding titration curve. The break point of this curve is the saturation point of the system and its xy coordinates were determined by establishing the intersection of the linear fits of the pre- and post-saturation curves. ΔA$_{saturation}$ was calculated and employed to determine the concentration of free ligand in solution at each titration point. ΔA was plotted versus ΔA/free ligand concentration to give a Scatchard plot from which the binding constants were determined.

TABLE 4

Binding Constants and MIC Values for Glycopeptide Analogs

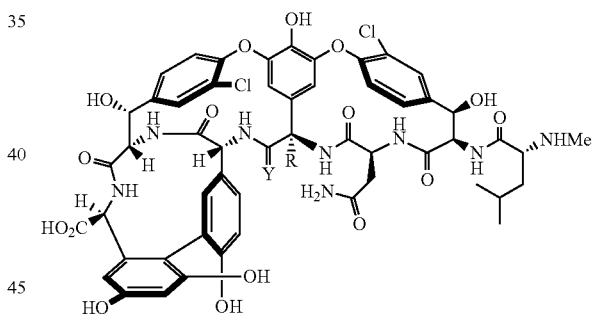

2, Y = O
3, Y = H$_2$
4, Y = NH
5, Y = S

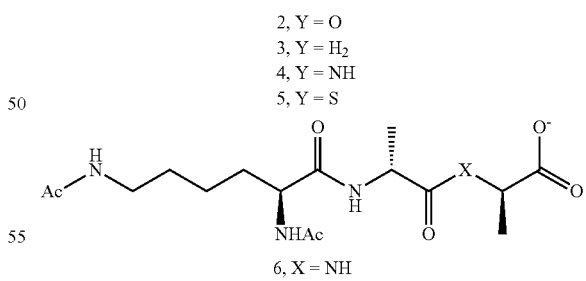

6, X = NH
7, X = O

| compound | ligand, $K_a$ (M$^{-1}$) | | | VanA[a] |
| --- | --- | --- | --- | --- |
|  | 6, X = NH | 7, X = O | $K_a$(6/7) | MIC, µg/mL |
| 2, Y = O | 1.7 × 10$^5$ | 1.2 × 10$^2$ | 1400 | 640 |
| 3, Y = H$_2$ | 4.8 × 10$^3$ | 5.2 × 10$^3$ | 0.9 | 31 |
| 4, Y = NH | 7.3 × 10$^4$ | 6.9 × 10$^4$ | 1.05 | 0.31 |
| 5, Y = S | 1.7 × 10$^2$ | 1.1 × 10$^1$ | — | >640 |

[a]Minimum inhibitory conc., *E. faecalis* (BM4166, VanA VRE).

Dosage Forms and Administration

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

EXAMPLES

Synthetic Procedures

[Ψ[C(=S)NH]Tpg$^4$]Vancomycin Aglycon (IVA).

Prepared by total synthesis in work whose full details will be disclosed elsewhere.[25] White film; $^1$H NMR (CD$_3$OD, 600 MHz) δ 7.65 (br s, 3H), 7.59 (d, J=12 Hz, 1H), 7.37 (br s, 1H), 7.28 (d, J=6.0 Hz, 1H), 7.21 (br s, 1H), 6.75 (d, J=6 Hz, 1H), 6.44 (s, 1H), 6.39 (s, 1H), 6.12 (br s, 1H), 5.82 (br s, 1H), 5.41-5.24 (m, 4H), 4.85-4.70 (m, 3H, obscured by D$_2$O), 4.42 (d, J=12 Hz, 1H), 4.27 (s, 1H), 4.05-3.97 (m, 1H), 3.03 (d, J=6 Hz, 1H), 2.77 (s, 3H), 2.22-2.17 (m, 1H), 1.91-1.93 (m, 1H), 1.74-1.64 (m, 1H), 1.64-1.56 (m, 1H), 0.99-0.89 (m, 6H); ESI-TOF HRMS m/z 1159.2710 (M$^+$+H, C$_{53}$H$_{53}$Cl$_2$N$_8$O$_{16}$S requires 1159.2672).

[Ψ[C(=NH)NH]T$_{pg}^4$]Vancomycin Aglycon (IIA).

A solution of (IVA) (0.46 mg, 0.40 µmol) in anhydrous methanol saturated with ammonia (0:5 mL) was treated with silver acetate (AgOAc, 0.70 mg, 4.2 µmol, 10 equiv). The reaction mixture was stirred at room temperature for 12 h before the solvent was removed under a stream of N$_2$. The residue was dissolved in 30% CH$_3$OH in water (0.4 mL+10 µL TFA) and purified by semi-preparative reverse-phase HPLC (CH$_3$OH/H$_2$O-0.07% TFA 30:70, 3 mL/min, R$_t$=17.9 min) to afford 6 as a white film: $^1$H NMR (CD$_3$OD, 600 MHz) δ 7.73-7.64 (m, 2H), 7.61-7.52 (br m, 1H), 7.41 (br s, 1H), 7.12 (d, J=6 Hz, 1H), 7.08-7.02 (m, 2H), 6.87 (d, J=12 Hz, 1H), 6.49-6.42 (m, 2H), 6.16-6.04 (br m, 1H), 5.53 (br s, 1H), 5.47-5.29 (m, 4H), 4.75-4.50 (m, 3H, obscured by D$_2$O), 4.31-4.24 (m, 1H), 4.22-4.12 (m, 1H), 4.11-4.05 (m, 1H), 2.85 (s, 3H), 2.85-2.81 (m, 1H), 2.45-2.37 (m, 1H), 1.85-1.75 (m, 1H), 1.64-1.54 (m, 2H), 0.94-0.79 (m, 6H); MALDI-TOF m/z 1142.3 (M$^+$+H, C$_{53}$H$_{54}$Cl$_2$N$_9$O$_{16}$ requires 1142.3); ESI-TOF FIRMS m/z 1142.3077 (M$^+$+H, C$_{53}$H$_{54}$O$_2$N$_9$O$_{16}$ requires 1142.3066).

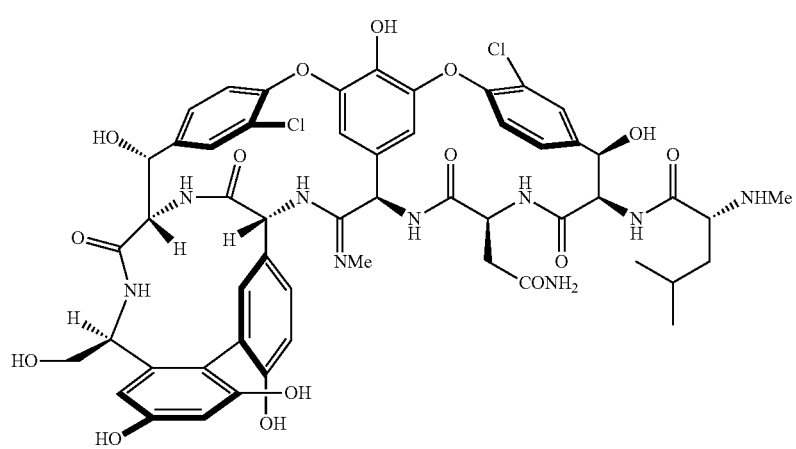

(11)

Compound 11:

white film; $^1$H NMR (DMSO-d$_6$, 600 MHz) inseparable geometrical isomers (ca A:B=1:1) δ 10.1-10.0 (br m, 1H), 9.26-9.22 (m, 1H), 9.19-9.16 (br m, 1H), 8.82-8.81 (m, 1H), 8.25-8.17 (m, 3H), 8.15-8.12 (m, 2H), 7.56-7.45 (m, 5H), 7.37-7.35 (br m, 1H), 7.28-7.23 (m, 3H), 7.18-7.15 (m, 1H), 7.12-7.06 (m, 3H), 7.01-6.97 (m, 1H), 6.81-6.80 (br m, 1H), 6.77 (d, 1H, J=4.2 Hz), 6.66-6.63 (br m, 1H), 6.29 (d, 1H, J=1.8 Hz), 6.09-6.04 (br m, 1H), 6.03-6.01 (m, 1H), 5.93 (d, 1H, J=7.2 Hz), 5.84-5.82 (m, 1H), 5.76 (d, 1H, J=3.0 Hz), 5.65 (d, 1H, J=7.2 Hz), 5.61-5.57 (m, 1H), 5.44 (d, 1H, J=6.0 Hz), 5.21-5.17 (m, 2H), 4.95-4.93 (br m, 1H), 4.50-4.45 (m, 1H), 4.17-4.16 (m, 2H), 3.66-3.55 (m, 8H), 2.75 (d, 2H, J=11.6 Hz), 2.69-2.66 (m, 3H), 2.09-2.06 (br m, 1H), 2.00-1.96 (m, 6H), 1.77-1.73 (m, 2H), 0.94-0.91 (m, 6H), 0.90-0.84 (m, 6H); ESI-TOF HRMS m/z 1142.3417 (M+H$^+$, C$_{54}$H$_{58}$Cl$_2$N$_9$O$_{15}$ requires 1142.3424).

(12)

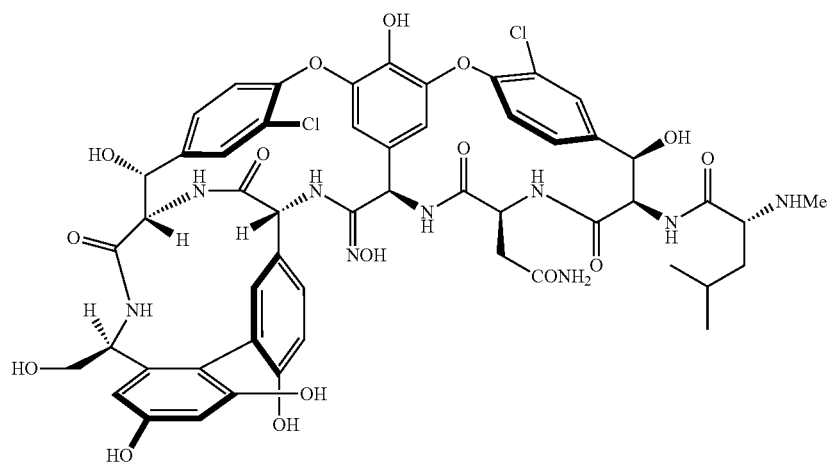

Compound 12:

white film; $^1$H NMR (CD$_3$OD, 600 MHz) δ 8.19-8.13 (m, 1H), 7.73-7.68 (m, 1H), 7.65-7.57 (m, 1H), 7.42-7.26 (m, 2H), 7.08 (d, 1H, J=8.4 Hz), 7.01 (d, 1H, J=3.6 Hz), 6.98-6.95 (br m, 1H), 6.82 (d, 1H, J=8.4 Hz), 6.66-6.61 (m, 1H), 6.42-6.38 (m, 1H), 5.60-5.47 (m, 3H), 5.44-5.39 (m, 1H), 5.36-5.32 (m, 1H), 5.27-5.22 (m, 1H), 5.01-4.96 (m, 1H), 4.38-4.20 (m, 3H), 4.05-3.99 (m, 1H), 3.98-3.91 (m, 1H), 3.88-3.85 (m, 1H), 3.46-3.40 (m, 1H), 2.84 (s, 3H), 2.43 (br d, 1H, J=18.4 Hz), 2.22-2.16 (m, 1H), 2.06-1.99 (m, 1H), 1.81-1.74 (m, 1H), 1.63-1.50 (m, 4H), 0.88-0.81 (m, 6H); ESI-TOF HRMS m/z 1144.3213 (M+H$^+$, C$_{53}$H$_{56}$Cl$_2$N$_9$O$_{16}$ requires 1144.3217).

Compound 13:

white film; $^1$H NMR (DMSO-d$_6$, 600 MHz) δ 9.24 (br s, 1H) 8.54-8.12 (On, 1H), 7.64-7.61 (m, 2H), 7.22-7.17 (m, 4H), 7.11-7.07 (m, 2H), 7.02-6.99 (br m, 1H), 6.68-6.63 (m, 2H), 6.54-6.52 (m, 2H), 6.35-6.32 (n, 1H), 5.85-5.82 (m, 1H), 5.77-5.74 (br m, 2H), 5.16-5.13 (m, 2H), 5.07-5.03 (m, 4H), 4.87 (d, 1H, J=5.4 Hz), 4.72-4.69 (m, 1H), 4.64-4.62 (m, 1H), 3.58-3.55 (m, 2H), 3.49-3.47 (m, 4H), 2.85 (d, 1H, J=12.0 Hz), 2.27-2.22 (n, 4H), 2.18-2.14 (m, 3H), 2.07-2.05 (m, 2H), 1.72 (br s, 1H), 1.54-1.51 (m, 1H), 0.89-0.79 (m, 6H); LCMS m/z 1257.3 (M+H$^+$, C$_{55}$H$_{58}$Cl$_2$F$_3$N$_{10}$O$_{17}$ requires 1257.1 for TFA salt); ESI-TOF HRMS m/z 1371.3159 (M C$_{57}$H$_{59}$Cl$_2$F$_6$N$_{10}$O$_{19}$ requires 1371.3239 for bis TFA salt).

(13)

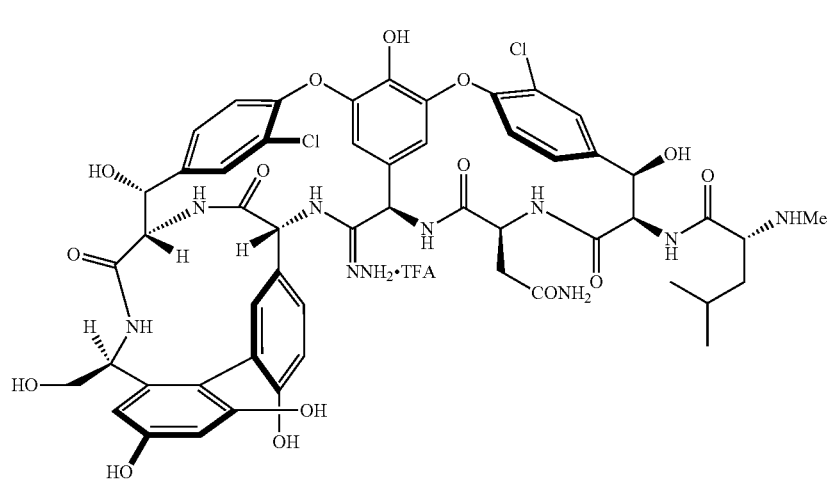

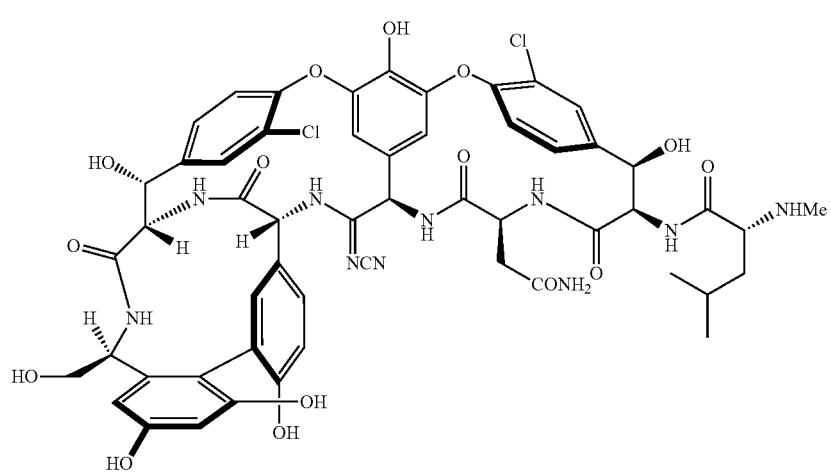

(14)

Compound 14:

white film; $^1$H NMR (CD$_3$OD, 600 MHz) δ 8.85 (d, 1H, J=6.0 Hz), 8.20-8.18 (m, 1H), 7.89-7.86 (m, 1H), 7.63-7.62 (m, 1H), 7.57-7.49 (m, 6H), 7.18 (d, 1H, J=8.4 Hz), 6.94-6.91 (br m, 1H), 6.66 (d, 1H, J=6.6 Hz), 6.56 (d, 1H, J=1.8 Hz), 6.53-6.52 (m, 1H), 6.30 (d, 1H, J=2.4 Hz), 5.72-5.62 (m, 2H), 5.15-5.11 (m, 1H), 4.54 (br s, 1H), 4.28-4.21 (m, 1H), 4.18-4.17 (m, 1H), 4.13-4.11 (m, 1H), 4.00-3.94 (m, 1H), 3.91-3.88 (m, 3H), 3.87-3.84 (m, 1H), 2.88 (s, 3H), 2.81-2.79 (m, 3H), 1.78-1.74 (m, 1H), 1.60-1.54 (m, 2H), 0.82-0.79 (m, 6H); ESI-TOF HRMS m/z 1153.3220 (M+H$^+$, C$_{54}$H$_{55}$Cl$_2$N$_{10}$O$_{15}$ requires 1153.3225).

General Procedure for Amidine Formation: (16)

A mixture of 15 (10.0 mg, 37.2 μmol) and silver tetrafluoroborate (21.7 mg, 0.112 mmol, 3.0 equiv) was treated with saturated NH$_3$/CH$_3$OH (0.37 mL) at 25° C. The reaction mixture was stirred at 25° C. for 2 h and concentrated under N$_2$ stream. The residue was purified by PTLC (SiO$_2$, 10% CH$_3$OH CH$_2$Cl$_2$) to afford 16 (7.5 mg, 83%).

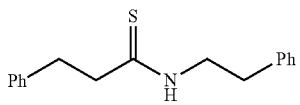 [SMILES: S=C(CCc1ccccc1)NCCc1ccccc1]

(15)

Compound 15:

white solid; m.p. 68-69° C.; $^1$H NMR (CD$_3$OD, 500 MHz) δ 7.31-7.18 (m, 10H), 3.78 (t, 2H, J=7.5 Hz), 3.05 (t, 2H, J=7.5 Hz), 2.88-2.85 (m, 4H), 2.17 (br s, 1H); $^{13}$C NMR (CD$_3$OD, 125 MHz) δ 205.3, 141.9, 140.2, 129.7, 129.6, 129.5, 129.4, 127.4, 127.2, 48.1, 36.8, 34.5, 30.7; IR (film) ν$_{max}$ 1647, 1199, 1121 cm$^{-1}$; ESI-TOP HRMS m/z 270.1306 (M+H$^+$, C$_{17}$H$_{20}$NS requires 270.1311).

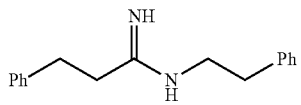

(16)

Compound 16:

light pink film; $^1$H NMR (CD$_3$OD, 500 MHz) δ 7.36-7.32 (m, 4H), 7.28-7.20 (m, 6H), 3.50 (t, 2H, J=7.0 Hz), 2.95 (t, 2H, J=7.5 Hz), 2.88 (t, 2H, J=7.0 Hz), 2.73 (t, 2H, J=7.5 Hz); $^{13}$C NMR (CD$_3$OD, 150 MHz) δ 168.5, 140.0, 139.0, 129.81, 129.79, 129.76, 129.4, 127.9, 44.6, 36.0, 34.6, 34.2; IR (film) ν$_{max}$ 1743, 1121, 1117 cm$^{-1}$; ESI-TOF HRMS m/z 253.1700 (M+H$^+$, C$_{17}$H$_{20}$N$_2$ requires 253.1699).

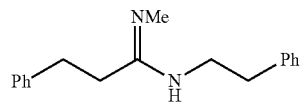

(17)

Compound 17:

white film; $^1$H NMR (CD$_3$OD, 400 MHz) inseparable geometrical isomers (isomer A:B=1.1:1) 87.38-7.15 (m, 2H), 3.59 (t, 2H, J=6.8 Hz), 3.47 (t, 2H, J=7.2 Hz), 2.93 (t, 2H, J=7.6 Hz), 2.96-2.80 (m, 8H), 2.93 (s, 3H), 2.88 (s, 3H), 2.79 (t, 2H, J=7.6 Hz), 2.56 (t, 2H, J=7.2 Hz); $^{13}$C NMR (CD$_3$OD, 150 MHz) inseparable geometrical isomers (isomer A:B=1.1:1) 8167.4, 167.3, 139.3, 139.2, 138.49, 138.48, 129.6, 129.34, 129.30, 129.29, 129.24, 129.23, 129.0, 128.9, 127.53, 127.50, 127.4, 46.1, 43.7, 36.3, 34.0, 32.74, 32, 72, 32.3, 32.1, 30.1, 29.9, 28.3; IR (film) ν$_{max}$ 1647, 1116, 1021 cm$^{-1}$; ESI-TOF HRMS m/z 267.1858 (M+H$^+$, C$_{18}$H$_{23}$N$_2$ requires 267.1856).

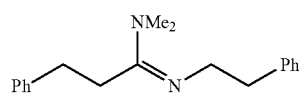

(18)

Compound 18:

light pink solid; m.p. 146-148° C.; $^1$H NMR (CD$_3$OD, 400 MHz) δ 7.37-7.20 (m, 10H), 3.53 (t, 2H, J=7.2 Hz), 3.35-3.33 (m, 2H), 3.15 (s, 314), 3.13 (s, 3H), 2.90 (t, 2H, J=7.2 Hz), 2.83-2.81 (m, 2H); $^{13}$C NMR (CD$_3$OD, 150 MHz) δ 175.5, 147.7, 147.0, 138.0, 137.9, 137.8, 137.5, 136.2, 136.0, 55.3, 49.3, 47.5, 44.9, 40.2, 37.7; IR (film) ν$_{max}$ 1627, 1121, 1093 cm$^{-1}$; ESI-TOF HRMS m/z 281.2013 (M+H$^+$, C$_{19}$H$_{25}$N$_2$ requires 281.2012).

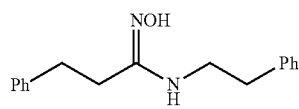

(19)

Compound 19:

white film; ¹H NMR (CD₃OD, 500 MHz) inseparable geometrical isomers (isomer A:B=18:1) δ (for isomer A) 7.32-7.17 (m, 10H), 3.40 (t, 2H, J=7.0 Hz), 2.81 (t, 2H, J=7.0 Hz), 2.77-2.73 (m, 2H), 2.34-2.31 (m, 2H); ¹³C NMR (CD₃OD, 150 MHz) inseparable geometrical isomers δ (for isomer A) 156.2, 141.2, 139.4, 129.0, 128.6, 128.5, 128.4, 126.5, 126.2, 43.9, 37.7, 33.6, 30.4; IR (film) $v_{max}$ 3317, 1623, 1121, 1092 cm⁻¹; ESI-TOF FIRMS m/z 269.1650 (M+H⁺, $C_{17}H_{21}N_2O$ requires 269.1648).

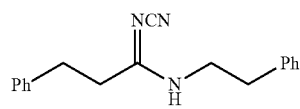

(21)

Compound 21:

white solid; m.p. 131-132° C.; ¹H NMR (CD₃OD, 500 MHz) inseparable geometrical isomers (isomer A:B=26:1) δ (for isomer A) 7.33-7.18 (m, 10H), 3.47 (t, 2H, J=7.0 Hz), 3.00-2.96 (m, 2H), 2.81-2.77 (m, 4H); ¹³C NMR (CD₃OD, 150 MHz) inseparable geometrical isomers (isomer A:B=26:1) (for isomer A) 205.2, 142.0, 140.2, 129.7, 129.6, 129.57, 129.52, 129.4, 127.4, 127.2, 48.1, 36.8, 34.5; IR (film) $v_{max}$ 2215, 1623, 1121 cm⁻¹; ESI-TOF HRMS m/z 278.1653 (M+H⁺, $C_{18}H_{20}N_3$ requires 278.1652).

Compound (42)

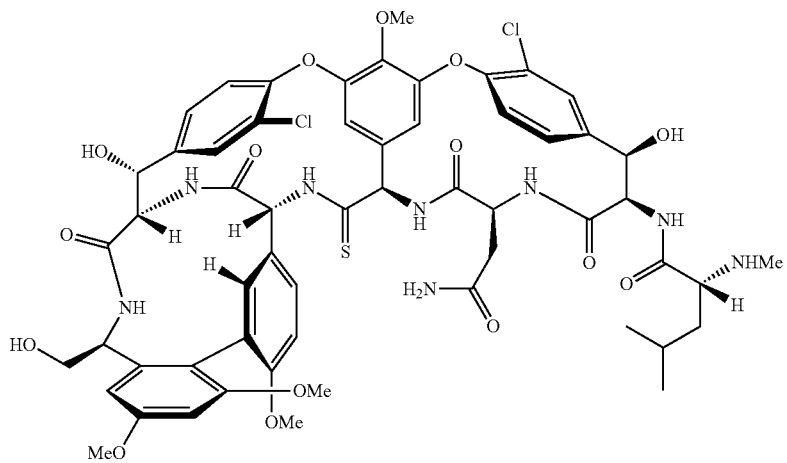

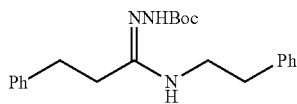

(20)

Compound 20:

white film; ¹H NMR (CD₃OD, 500 MHz) inseparable geometrical isomers (isomer A:B=ca 1:1) δ 7.30-7.21 (m, 20H), 3.45-3.42 (m, 4H), 3.40-3.38 (br m, 2H), 2.86-2.78 (m, 8H), 2.56-2.52 (m, 2H), 2.47-2.43 (m, 2H), 1.51 (s, 18H); ¹³C NMR (CD₃OD, 150 MHz) inseparable geometrical isomers (isomer A:B=ca 1:1) δ 168.8, 163.4, 157.1, 156.5, 141.5, 141.0, 140.3, 139.2, 129.5, 129.3, 129.2, 129.03, 128.96, 128.9, 128.84, 128.80, 127.1, 126.9, 126.8, 126.7, 80.9, 80.1, 45.2, 43.4, 37.3, 35.0, 33.8, 33.5, 32.8, 32.2, 30.2, 28.3, 28.1; IR (film) $v_{max}$ 1828, 1697, 1121, 1094 cm⁻¹; ESI-TOF HRMS m/z 368.2331 (M+H⁺, $C_{22}H_{29}N_3O_2$ requires 368.2332).

A solution of 32 (2.05 mg, 1.49 μmol) in neat TFA (0.5 mL) was stirred at 25° C. for 12 h. The solvent was removed under a stream of N₂, the crude residue was dissolved in MeOH and the solution was stirred for 18 h before the solvent was removed under a stream of N₂. The residue was dissolved in 1:1 MeOH:H₂O (0.5 mL) and purified by semi-preparative reverse-phase HPLC (10-50% MeCN/H₂O□0.07% TFA) to afford 42 (1.24 mg, 69%) as a white film: ¹H NMR (CD₃OD, 600 MHz) δ 7.67-7.63 (m, 2H), 7.58 (dd, J=12.2, 2.2 Hz, 1H), 7.51 (br s, 1H), 7.38 (d, J=12.1 Hz, 1H), 7.33 (d, J=12.2 Hz, 1), 7.30 (dd, J=14.5, 4.4 Hz, 1H), 7.03 (d, J=12.2 Hz, 1H), 6.85 (d, J=2.1 Hz, 1H), 6.58 (d, J=2.2 Hz, 1H), 6.53 (d, J=2.3 Hz, 1H), 6.26 (d, J=2.2 Hz, 1H), 6.04 (d, J=2.2 Hz, 1H), 5.49 (d, J=4.6 Hz, 1H), 5.32 (d, J=4.5 Hz, 1H), 5.21 (t, J=4.6 Hz, 1H), 5.16 (s, 1H), 4.22-4.14 (m, 1H), 4.17 (s, 3H), 4.01-3.94 (m, 2H), 3.93-3.87 (m, 1H), 3.86 (s, 3H), 3.75 (s, 1H), 3.74-3.71 (m, 2H), 3.69 (s, 3H), 3.64 (s, 3H), 2.83 (s, 3H), 2.78 (dd, J=12.4, 4.6 Hz, 1H), 2.56 (dd, J=12.1, 4.5 Hz, 1H), 1.90-1.84 (m, 2H), 1.74-1.64 (m, 2H), 0.93 (d, J=6.2 Hz, 3H), 0.90 (d, J=6.2 Hz, 3H); ESI-TOF HRMS m/z 1201.2483 (M⁺+H, $C_{57}H_{62}Cl_2N_8O_{15}S$ requires 1201.3505).

Compound (43)

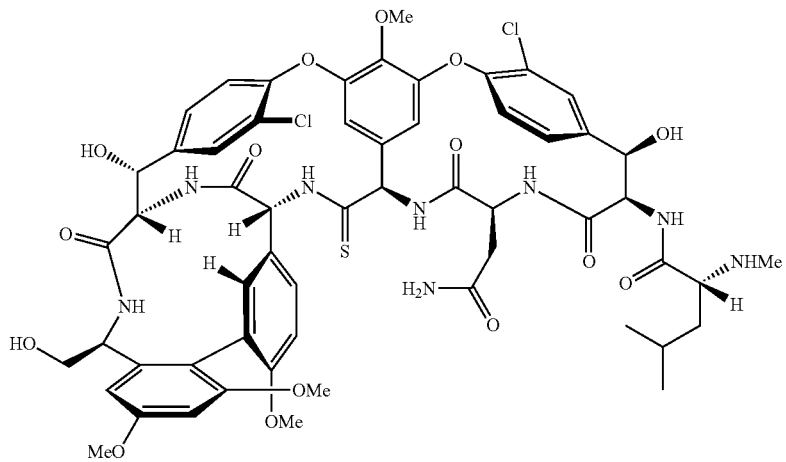

A solution of 42 (1.24 mg, 1.03 μmol) in anhydrous saturated NH₃☐CH₃OH (0.5 mL) was treated with silver acetate (1.72 mg, 10.3 μmol, 10 equiv). The reaction mixture was stirred at room temperature for 24 h before the solvent was removed under a stream of N$_2$. The residue was dissolved in 40% MeOH H$_2$O (0.4 mL+10 μL TFA) and purified by semi-preparative reverse-phase HPLC (10-20% MeCN/H$_2$O-0.07% TFA) to afford 43 (0.77 mg, 63%) as a white film. The sample of 43, even after repeated purification, appears to rapidly equilibrate to three easily separable (HPLC) components (1:1:2) all of which display the same mwt (MS): ESI-TOF HRMS m/z 1184.3874 (M$^+$+H, C$_{57}$H$_{63}$Cl$_2$N$_9$O$_{15}$ requires 1184.3893).

Compound (44)

Compound 44. is identical to compound 9 of FIG. 3. A solution of 32 (2.20 mg, 1.60 mop in neat TFA (0.6 mL) was stirred at 25° C. for 12 h. The solvent was removed under a stream of N$_2$ and the residue of 42 was treated with AlBr$_3$ (107 mg, 400 μmol) and EtSH (100 μL). The resulting mixture was stirred at 25° C. for 60 h before it was diluted with CH$_2$Cl$_2$ (0.5 mL), cooled to 0° C., and quenched by the addition of CH$_3$OH (0.2 mL). The solvent was removed under a stream of N$_2$. The residue was suspended in water (0.5 mL), and purified by short reverse-phase silica gel chromatography (C18-SiO$_2$, 50% CH$_3$CN—H$_2$O) and semi-preparative reverse-phase HPLC (5-20% MeCN/H$_2$O-0.07% TFA gradient over 10 min then 20% MeCN/H$_2$O-0.07% TFA isocratic) to afford 44 (1.12 mg, 61%, 2 steps) as a white film: $^1$H NMR (CD$_3$OD, 600 MHz) δ 8.34 (br d, J=12.2 Hz, 1H), 8.23 (br s, 1H), 7.70-7.57 (m, 4H), 7.37-7.32 (m, 1H), 7.29 (d, J=12.2 Hz, 1H), 7.19 (d, J=2.2 Hz, 1H), 6.65 (d, J=2.1 Hz, 1H), 6.42 (d, J=2.2 Hz, 1H), 6.15 (br d, J=2.2 Hz, 1H), 5.82 (br s, 1H), 5.39-5.24 (m, 4H), 4.28 (d, J=4.6 Hz, 1H), 4.26-4.24 (m, 1H), 4.23 (s, 1H), 4.08-3.96 (m, 3H), 3.02 (br d, J=12.2 Hz, 1H), 2.78 (s, 3H), 2.32-2.22 (m, 1H), 1.92-1.83 (m, 1H), 1.78-1.65 (m, 2H), 1.00 (d, J=6.2 Hz, 3H), 0.98 (d, J=6.2 Hz, 3H); ESI:TOF HRMS m/z 1145.1974 (M$^+$+H, C$_{53}$H$_{55}$Cl$_2$N$_8$O$_{15}$S requires 1145.2806).

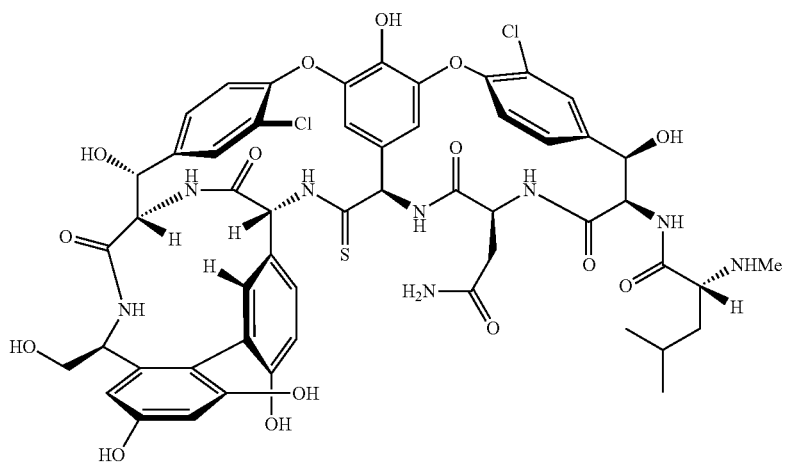

Compound (45)

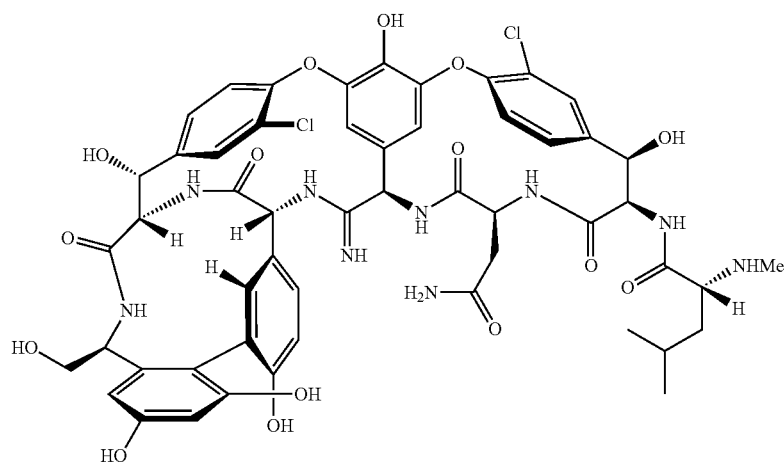

Compound 45 is identical to compound 10 of FIG. 3. A solution of 44 (1.12 mg, 0.977 μmol) in anhydrous saturated NH₃☐CH₃OH (0.3 mL) was treated with silver acetate (1.63 mg, 9.77 μmol). The reaction mixture was stirred at 25° C. for 12 h before the solvent was removed under a stream of N$_2$. The residue was dissolved in 40% MeOH H$_2$O (0.4 mL+10 μL TFA) and purified by short reverse-phase silica gel chromatography (C18-SiO$_2$, 50% CH$_3$CN—H$_2$O) to provide 45 (0.94 mg, 85%) as an off-white solid that was further purified by semi-preparative reverse-phase HPLC (5-20% MeCN/H$_2$O-0.07% TFA over 10 min then 20% MeCN/H$_2$O-0.07% TFA isocratic) prior to biological testing to afford 45 as a white film: $^1$H NMR (CD$_3$OD, 600 MHz) δ 7.56 (s, 1H), 7.52-7.46 (m, 2H), 7.34 (s, 1H), 7.21 (d, J=12.1 Hz, 1H), 6.96-6.90 (m, 2H), 6.73 (d, J=12.2 Hz, 1H), 6.58 (br s, 1H), 6.31 (s, 1H), 5.68 (s, 1H), 5.34 (d, J=4.4 Hz, 1H), 5.19 (s, 2H), 5.10-4.70 (m, 2H, obstructed by H$_2$O), 4.52 (br s, 1H), 4.26 (br s, 1H), 4.13-4.04 (m, 1H), 4.01-3.87 (m, 3H), 2.75 (d, J=12.2 Hz, 1H), 2.35 (dd, J=16.2, 4.4 Hz, 1H), 2.26 (s, 3H), 1.81-1.71 (m, 1H), 1.60-1.41 (m, 2H), 1.31-1.08 (m, 2H), 0.91-0.80 (m, 6H); ESI-TOF HRMS m/z 1128.2276 (M$^+$+H, C$_{53}$H$_{56}$Cl$_2$N$_9$O$_{15}$ requires 1128.3195).

Titration Binding Assays with Model D-Ala-D-Ala and D-Ala-D-Lac Ligands 6 and 7.

The binding constants for all compounds for association with the model ligands N,N'-Ac$_2$-Lys-D-Ala-D-Ala (6) and N,N'-Ac$_2$-Lys-D-Ala-D-Lac (7) were determined according to literature protocol. UV difference experiments were carried out on a CARY 3E UV-Vis spectrometer. UV scans were run with a baseline correction that consisted of 0.02 M sodium citrate buffer (pH=5.1) and covered a range from 200 to 345 nm. A solution of the vancomycin aglycon derivative (7.7×10$^{-5}$ M in 0.02 M sodium citrate buffer) was placed into a quartz UV cuvette (0.1 cm path length) and the UV spectrum recorded versus a reference cell containing 0.02 M sodium citrate buffer. UV spectra were recorded after each addition of a solution of N,N'-Ac$_2$-Lys-D-Ala-D-Ala (6) or N,N'-Ac$_2$-Lys-D-Ala-D-Lac (7) in 0.02 M sodium citrate buffer to each cell from 0.1 to 60.0 equivalents. The absorbance value at the $\lambda_{max}$ was recorded and the running change in absorbance, $\Delta A_{x\ equiv}$ ($A_{initial} - A_{x\ equiv}$), measured. The number of ligand equivalents was plotted versus $\Delta A$ to afford the ligand binding titration curve. The break point of this curve is the saturation point of the system and its xy coordinates were determined by establishing the intersection of the linear fits of the pre and postsaturation curves. $\Delta A_{saturation}$ was calculated and employed to determine the concentration of free ligand in solution at each titration point. $\Delta A$ was plotted versus $\Delta A$/free ligand concentration to give a Scatchard plot from which the binding constants were determined.

Antimicrobial Assays.

S. Aureus (ATCC 25923) and E. Faecalis (BM4166) were propagated and MICs were determined in duplicate by the broth microdilution method according to standard microbiological practice. (Clinical and Laboratory Standards Institute. Methods for Dilution Antimicrobial Susceptibility Tests for Bacteria That Grow Aerobically; Approved Standard, 7th ed.; CLSI document M07-A8; Clinical and Laboratory Standards Institute: Wayne, Pa., 2009.)

DOCUMENTS CITED (1) Hamad, B. (2010) The antibiotic market. Nat. Rev. Drug Discovery 9, 675-676.
(2) Parker, M. T. and Jevons, M. P. (1964) A survey of methicillin resistance in Staphylococcus aureus. Postgrad Med. J. 40, 170-178.
(3) McCormick, M. H., Stark, W. M., Pittenger, G. E., Pittenger, R. C., and McGuire, J. M. (1955-1956) Vancomycin, a new antibiotic. I. Chemical and biologic properties. Antibiot. Annu., 606-611.
(4) Harris, C. M., Kopecka, H., and Harris, T. M. (1983) Vancomycin: structure and transformation to CDP-1. J. Am. Chem. Soc. 105, 6915-6922.
(5) Nagarajan, R., Ed. (1994) Glycopeptide Antibiotics, Marcel Dekker Inc., New York.
(6) Walsh, C. T. and Fischbach, M. A. (2009) New ways to squash superbugs. Sci. Amer. 301, 44-51.
(7) Cooper, G. L. and Given, D. B. (1986) The development of vancomycin. In Vancomycin, A Comprehensive Review of 30 Years of Clinical Experience, pp 1-5, Park Row Publications, Indianapolis, Ind.
(8) Howden, B. P., Davies, J. K., Johnson, P. D., Stinear, T. P., and Grayson, M. L. (2010) Reduced vancomycin susceptibility in Staphylococcus aureus, including vancomycin-intermediate and heterogeneous vancomycin-intermediate strains: resistance mechanisms, laboratory detection, and clinical implications. Clin. Microbiol. Rev. 23, 99-139.

(9) CDC Reminds clinical laboratories and healthcare infection preventionists of their role in the search and containment of vancomycin-resistant *Staphylococcus aureus* (VRSA), May 2010.

(10) Zhu, W., Murray, P. R., and Huskins, W. C. (2010) Dissemination of an *Enterococcus* Inc18-like VanA plasmid associated with vancomycin-resistant *Staphylococcus aureus*. Antimicrob. Agents Chemother 54, 4214-4320.

(11) Perkins, H. R. (1982) Vancomycin and related antibiotics. Pharmacol. Ther. 16, 181-197.

(12) Bugg, T. D. H., Wright, G. D., Dutka-Malen, S., Arthur, M., Courvalin, P., and Walsh, C. T. (1991) Molecular basis of vancomycin resistance in *Enterococcus faecium* BM4147: biosynthesis of a depsipeptide peptidoglycan precursor by vancomycin resistance proteins VanH and VanA. Biochemistry 30, 10408-10415.

(13) McComas, C. C.; Crowley, B. M.; Boger, D. L. *J. Am. Chem. Soc.* 2003, 125, 9314.

(14) (a) Evans, D. A.; DeVries, K. M. *Drugs Pharm. Sci.* 1994, 63, 63. (b) Nicolaou, K. C.; Boddy, C. N. C.; Brase, S.; Winssinger, N. *Angew. Chem., Int. Ed.* 1999, 38, 2096.

(15) Boger, D. L. *Med. Res. Rev.* 2001, 21, 356.

(16) (a) Boger, D. L.; Miyazaki, S.; Kim, S. H.; Wu, J. H.; Castle, S. L.; Loiseleur, O.; Jin, Q. *J. Am. Chem. Soc.* 1999, 121, 10004. (b) Boger, D. L.; Miyazaki, S.; Kim, S. H.; Wu, J. H.; Loiseleur, O.; Castle, S. L. *J. Am. Chem. Soc.* 1999, 121, 3226.

(17) (a) Boger, D. L.; Kim, S. H.; Mori, Y.; Weng, J. H.; Rogel, O.; Castle, S. L.; McAtee, J. J. Am. Chem. Soc. 2001, 123, 1862. (b) Boger, D. L.; Kim, S. H.; Miyazaki, S.; Strittmatter, H.; Weng, J. H.; Mori, Y.; Rogel, O.; Castle, S. L.; McAtee, J. J. *J. Am. Chem. Soc.* 2000, 122, 7416.

(18) Crowley, B. M.; Mori, Y.; McComas, C. C.; Tang, D.; Boger, D. L. *J. Am. Chem. Soc.* 2004, 126, 4310.

(19) (a) Shimamura, H.; Breazzano, S. P.; Garfunkle, J.; Kimball, F. S.; Trzupek, J. D.; Boger, D. L. J. Am. Chem. Soc. 2010, 132, 7776. (b) Garfunkle, J.; Kimball, F. S.; Trzupek, J. D.; Takazawa, S.; Shimamura, H.; Tomishima, M.; Boger, D. L. *J. Am. Chem. Soc.* 2009, 131, 16036.

(20) (a) Crane, C. M.; Pierce, J. G.; Leung, S. S. F.; Tirado-Rives, J.; Jorgensen, W. L.; Boger, D. L. *J Med. Chem.* 2010, 53, 7229. (b) Crane, C. M.; Boger, D. L. *J. Med. Chem.* 2009, 52, 1471.

(21) Moser, H.; Fliri, A.; Steiger, A.; Costello, G.; Schreiber, J.; Eschenmoser, A. *Helv. Chim. Acta* 1986, 69, 1224.

(22) Jones, R. C. F.; Ward, G. *J. Tetrahedron Lett.* 1988, 29, 3853.

(23) Inokuchi, E.; Oishi, S.; Kubo, T.; Ohno, H.; Shimura, K.; Matsuoka, M.; Fujii, N. *ACS Med. Chem. Lett.* 2011, 2, 477.

(24) Crowley, B. M.; Boger, D. L. *J. Am. Chem. Soc.* 2006, 128, 2885.

(25) (a) Xie, J.; Pierce, J. G.; James, R. C.; Okano, A.; Boger, D. L. *J. Am. Chem. Soc.* 2011, 133, 13946. (b) Xie, J., Okano, A., Pierce, J. G., James, R. C., Stamm, S., Crane, C. M.; Boger, D. L. *J. Am. Chem. Soc.* 2012, 134, 1284.

(26) Boger, D. L., Kim, S. H., Miyazaki, S., Strittmatter, H., Weng, J.-H., Mori, Y., Rogel, O., Castle, S. L., and McAtee, J. J. (2000) Total synthesis of the teicoplanin aglycon. *J. Am. Chem. Soc.* 122, 7416-7417.

(27) Boger, D. L., Kim, S. H., Mori, Y., Weng, Rogel, O., Castle, S. L., and McAtee, J. J. (2001) First and second generation total synthesis of the teicoplanin aglycon. *J. Am. Chem. Soc.* 123, 1862-1871.

(28) Crowley, B. M., Mori, Y., McComas, C. C., Tang, D., and Boger, D. L. (2004) Total synthesis of the ristocetin aglycon. *J. Am. Chem. Soc.* 126, 4310-4317.

(29) Garfunkle, J., Kimball, F. S., Trzupek, J. D., Takazawa, S., Shimamura, H., Tomishima, M., and Boger, D. L. (2009) Total synthesis of chloropeptin II (complestatin) and chloropeptin I. *J. Am. Chem. Soc.* 131, 16036-16038.

(30) Shimamura, H., Breazzano, S. P., Garfunkle, J., Kimball, F. S., Trzupek, J. D., and Boger, D. L. (2010) Total synthesis of complestatin: development of a Pd(0)-mediated indole annulation for macrocyclization. *J. Am. Chem. Soc.* 132, 7776-7783.

(31) Breazzano, S. P. and Boger, D. L. (2011) Synthesis and stereochemical determination of complestatin A and B (neuroprotectin A and B). *J. Am. Chem. Soc.* 133, 18495-18502.

(32) (a) Shibuya, I.; Taguchi, Y.; Tsuchiya, T.; Oishi, A.; Katoh, E. *Bull. Chem. Soc. Jpn.* 1994, 67, 3048. (b) Avalos, M.; Babiano, R.; Duran, C. J.; Jimenez, J. L.; Palacious, J. C. *Tetrahedron Lett.* 1994, 35, 477. (c) Cacchi, S.; La Torre, F.; Misiti, D. *Chem. Ind.* 1978, 669. (d) Corey, E. J.; Boger, D. L. *Tetrahedron Lett.* 1978, 5.

(33) (a) Marchand-Brynaert, J.; Moya-Portuguez, M.; Huber, I.; Ghosez, L. *J. Chem. Soc., Chem. Commun.* 1983, 818. (b) Sauve, G.; Rao, V. S.; Lajoie, G.; Belleau, B. *Can. J. Chem.* 1985, 63, 3089.

(34) Klevens, R. M.; Morrison, M. A.; Nadle, J.; Petit, S.; Gershman, K.; Ray, S.; Harrison, L. H.; Lynfield, R.; Dumyati, G.; Townes, J. M.; Craig, A. S.; Zell, E. R.; Fosheim, G. E.; McDougal, L. K.; Carey, R. B.; Fridkin, S. K. *JAMA* 2007, 298, 1763.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An antibiotic glycopeptide-analogous compound for treatment of glycopeptide-resistant bacterial infections, comprising a pseudopeptide analog of a glycopeptide antibiotic or aglycone thereof, wherein the compound comprises a core pseudopeptide sequence having an amidine group that replaces a carboxamide linking group of a core peptide of the glycopeptide antibiotic or aglycone thereof, wherein a carboxamide O atom of a D ring-bearing amino acid residue of the peptide core of the glycopeptide or aglycone has been replaced by an NH group, to provide a respective Ψ-amidine pseudopeptide analog of the glycopeptide antibiotic or aglycone.

2. The compound of claim 1, wherein the core peptide sequence of the glycopeptide or aglycone thereof is recited N-terminal to C-terminal aa-Phe'-aa-Phgly'-Phgly'-Phe'-Phgly', wherein aa signifies an amino acid residue, and Phe' and Phgly' signify modified phenylalanine and modified phenylglycine amino acid residues respectively; wherein the carboxamide group that is replaced by the amidine group is disposed at the fourth peptide bond from the N-terminal aa group.

3. The compound of claim 2, wherein the core peptide sequence is recited N-terminal to C-terminal aa-Phe'-Phgly'-Phgly'-Phgly'-Phe'-Phgly', wherein aa signifies an amino acid residue, and Phe' and Phgly' respectively signify modified phenylalanine and modified phenylglycine amino acid residues respectively; wherein the carboxamide group that is replaced by the amidine group is disposed at the fourth peptide bond from the N-terminal aa group.

4. The compound of claim 1, wherein the amino acid residue bearing the D ring is a Phgly' amino acid residue additionally coupled via aryl ether bonds to a C-ring of a Phe' amino acid residue and to an E-ring of a Phe' amino acid residue, wherein Phe' and Phgly' respectively signify modified phenylalanine and modified phenylglycine amino acid residues, respectively.

5. The compound of claim 1, wherein the D ring amino acid residue pseudopeptide amidine bond NH group, when complexed with a peptidoglycan bacterial cell wall precursor or model thereof comprising a D-Ala-D-Ala C-terminal dipeptide domain is hydrogen bonded in the complex to a peptide nitrogen atom of the D-Ala-D-Ala peptide bond.

6. The compound of claim 1, wherein the antibiotic glycopeptide-analogous compound is vancomycin, teicoplanin, balhimycin, actinoidin, or ristomycin.

7. The compound of claim 1 for treatment of infections caused by vancomycin-resistant bacteria, wherein the compound is any one of the following vancomycin-analogous [Ψ[C(=NH)NH]Tpg$^4$]-amidine analogs:

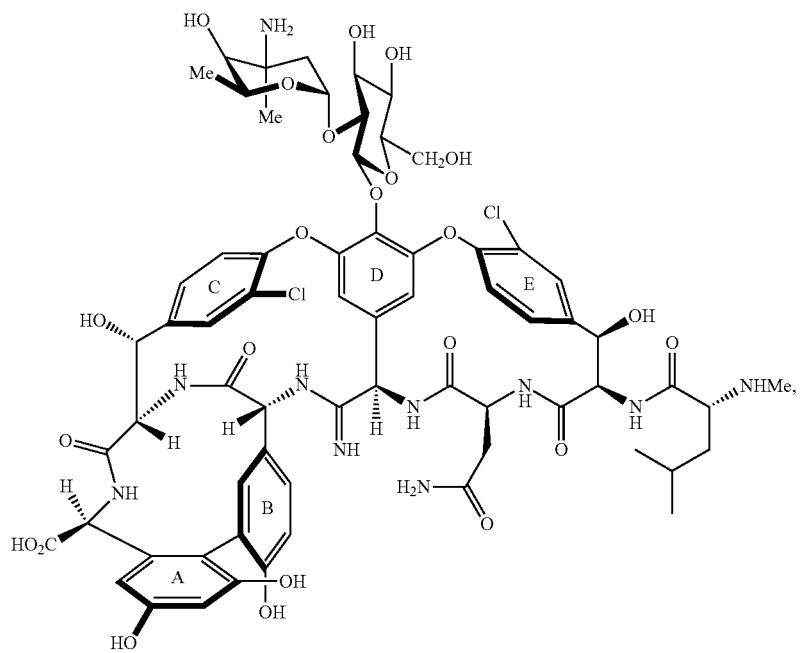

(IA)

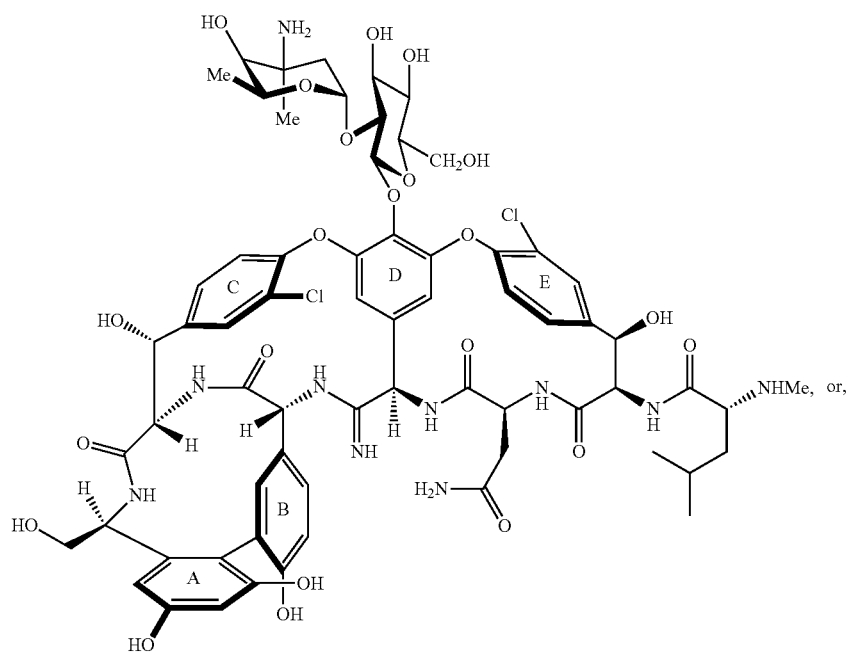
(IB)
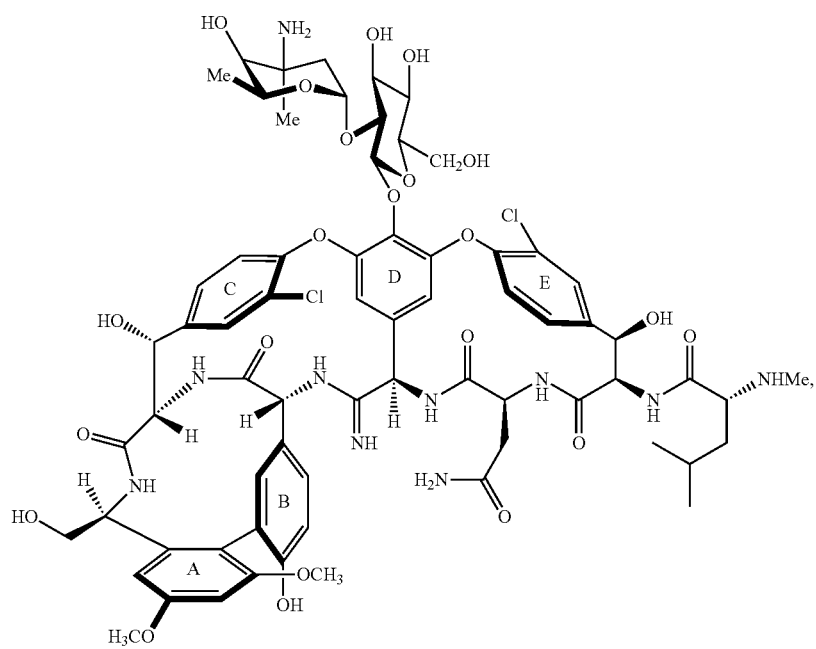
(IC)

or wherein the compound is any one of the following vancomycin aglycone [Ψ[C(=NH)NH]Tpg⁴]-amidine analogs:

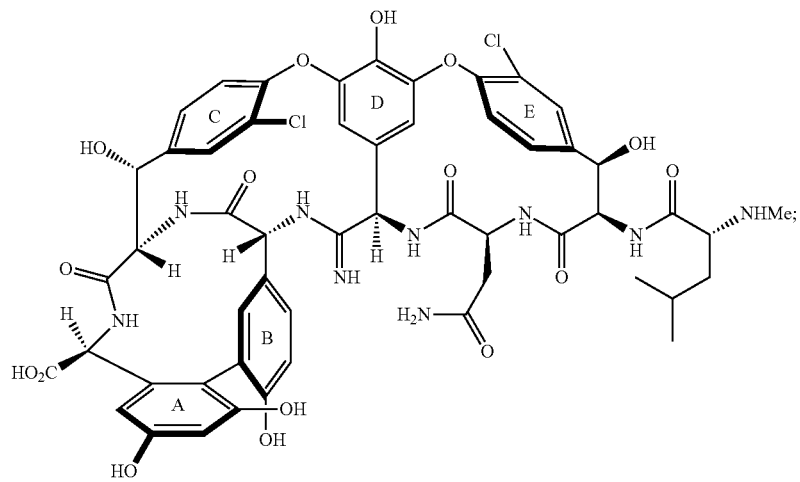

(IIA)

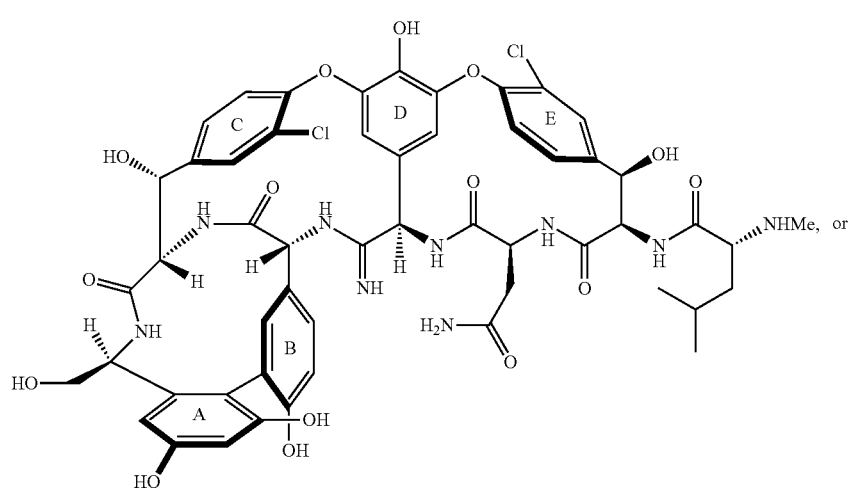

(IIB)

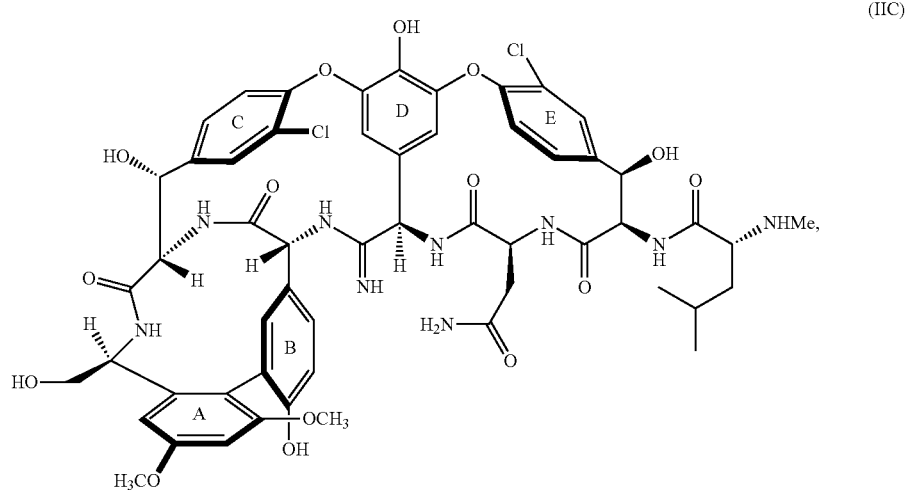

(IIC)

or any pharmaceutically acceptable salt thereof; or any combination thereof.

8. A glycopeptide-analogous compound for use as a precursor in preparation of an antibiotic of claim 1 for treatment of glycopeptide-resistant bacterial infections, comprising a pseudopeptide analog of a glycopeptide antibiotic or aglycone thereof, wherein the compound comprises a core pseudopeptide sequence having an thioamide group that replaces a carboxamide linking group of a core peptide of the glycopeptide antibiotic or aglycone thereof, wherein a carboxamide 0 atom of a D ring-bearing aminoacid residue of the peptide core of the glycopeptide or aglycone is replaced by an S atom, to provide a respective Ψ-thioamide pseudopeptide analog of the glycopeptide antibiotic or aglycone.

9. The compound of claim 8, wherein the core peptide sequence of the glycopeptide or aglycone thereof is recited N-terminal to C-terminal aa-Phe'-aa-Phgly'-Phgly'-Phe'-Phgly', wherein aa signifies an amino acid residue, and Phe' and Phgly' signify modified phenylalanine and modified phenylglycine amino acid residues respectively; wherein the carboxamide group that is replaced by the thioamide group is disposed at the fourth peptide bond from the N-terminal aa group.

10. The compound of claim 9, wherein the core peptide sequence is recited N-terminal to C-terminal aa-Phe'-Phgly'-Phgly'-Phgly'-Phe'-Phgly', wherein aa signifies an amino acid residue, and Phe' and Phgly' respectively signify modified phenylalanine and modified phenylglycine amino acid residues respectively; wherein the carboxamide group that is replaced by the thioamide group is disposed at the fourth peptide bond from the N-terminal aa group.

11. The compound of claim 8, wherein the compound is a vancomycin [Ψ[C(=S)NH]Tpg⁴]-thioamide analog of formula

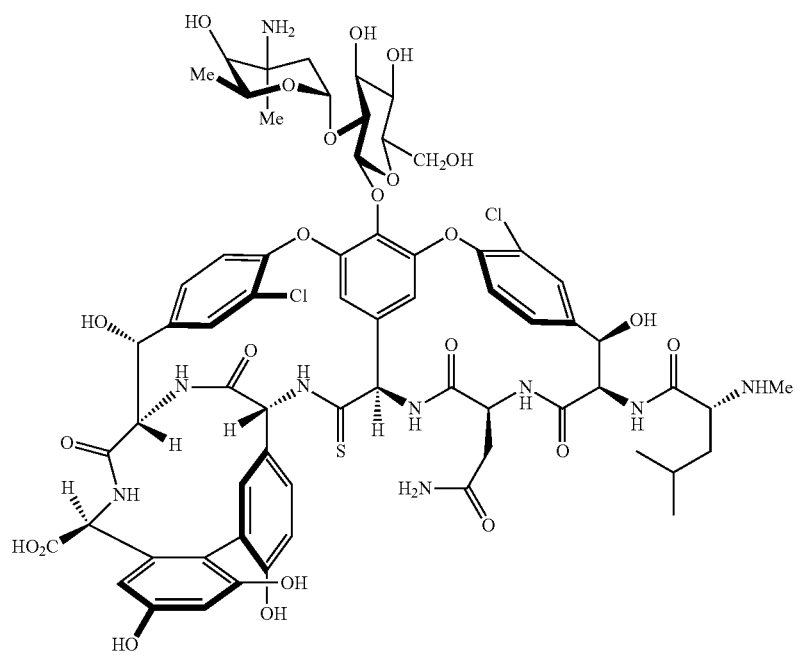

(IIIA)

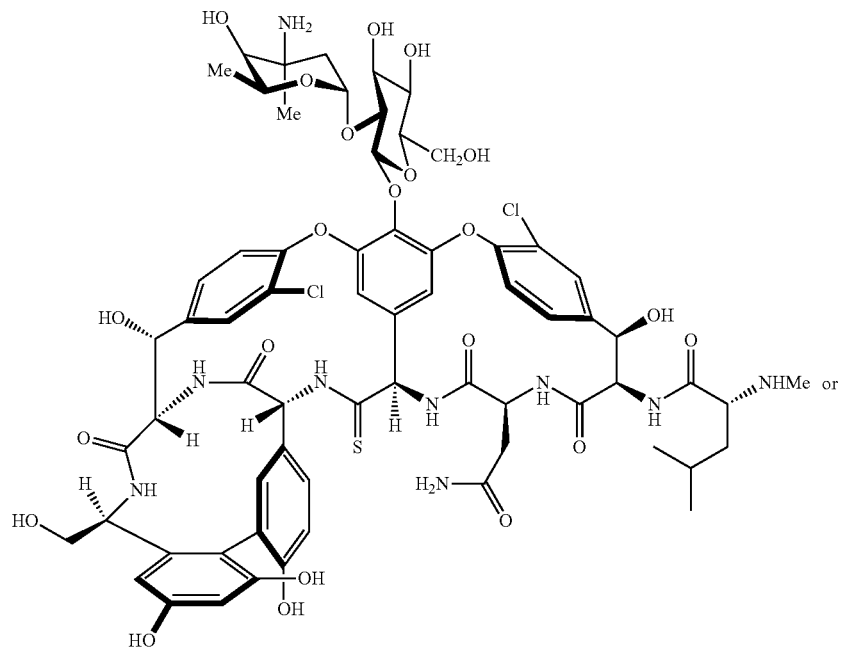

(IIIB)

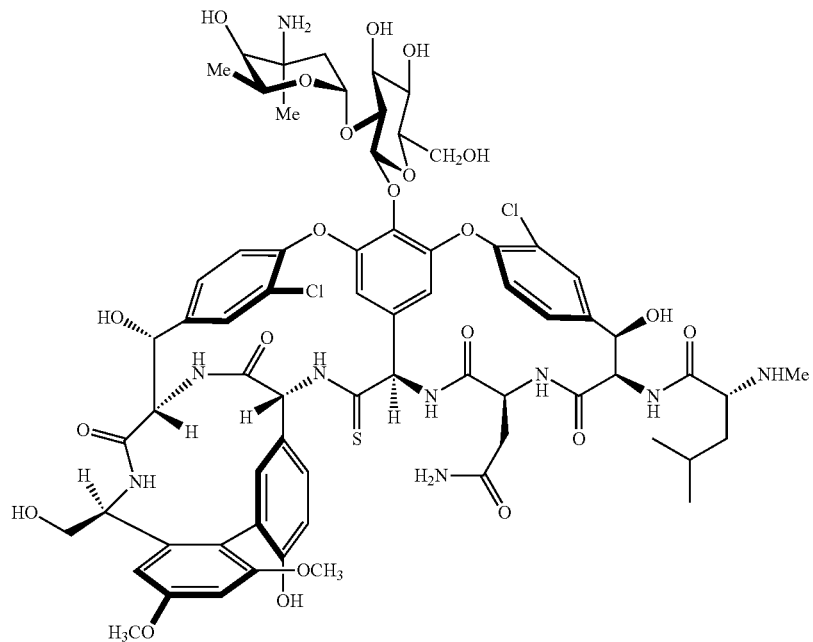
(IIIC)
or wherein the compound is a vancomycin aglycone [Ψ[C(=S)NH]Tpg⁴]-thioamide analog of formula
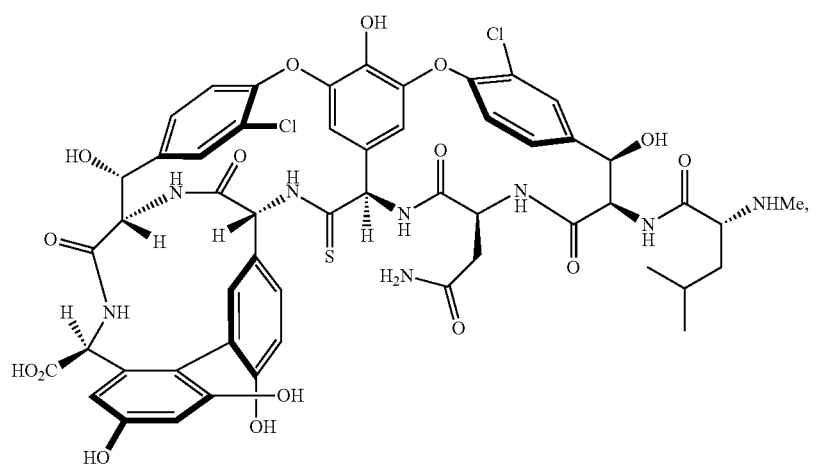
(IVA)

(IVB)

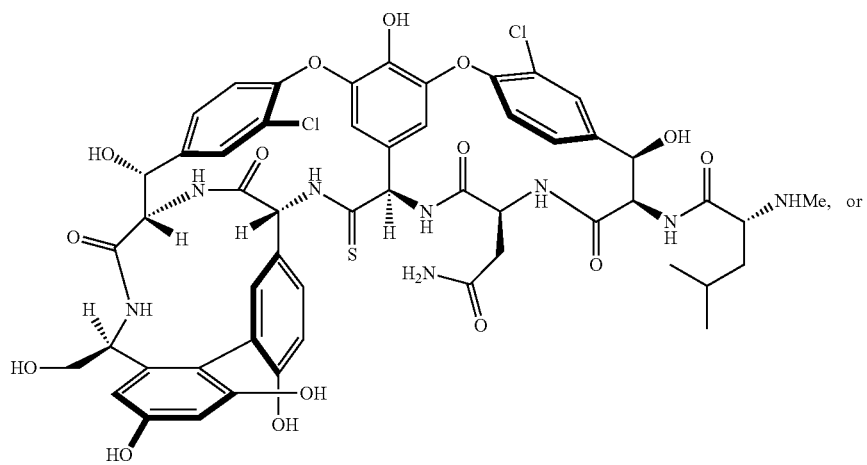

(IVC)

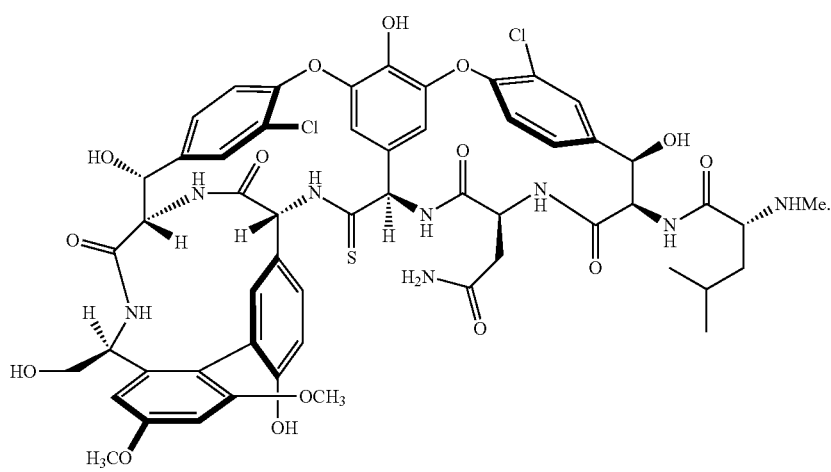

12. The compound of claim 1, comprising a [Ψ[C(=NH)NH]Tpg⁴]-analog of vancomycin or an aglycone thereof of formula (V)

(V)

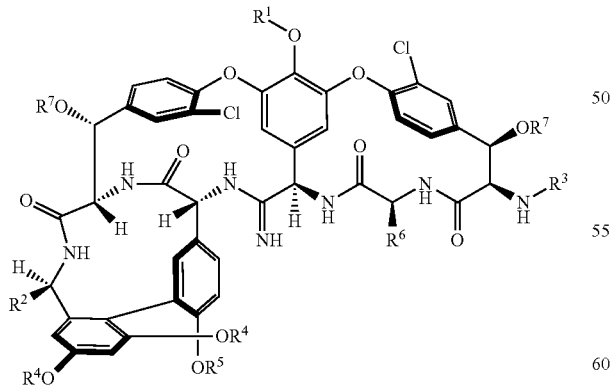

wherein
$R^1$ is H, or a glycosyl moiety;
$R^2$ is $CO_2R$, $CH_2OR$, or $CONR_2$, wherein R is H or $(C_1$-$C_6)$alkyl;
$R^3$ is an aminoacyl group, optionally N-alkylated;
$R^4$ at each occurrence is independently H, $(C_1$-$C_6)$alkyl, $(C_1$-$C_6)$alkanoyl, a glycosyl moiety;
$R^5$ is H, $(C_1$-$C_6)$alkyl, or $(C_1$-$C_6)$alkanoyl;
$R^6$ is group of formula, $(CR_2)$—$R^{6A}$ wherein $R^{6A}$ is aryl, $CO_2R$, $CONR_2$, $(C_1$-$C_6)$alkoxy, or $(C_1$-$C_6)$alkanoyl;
$R^7$ at each occurrence is independently H, or a glycosyl moiety;
or a pharmaceutically acceptable salt thereof;
or a mixture thereof.

13. The compound of claim 12 wherein the glycosyl moiety of $R^1$ is of formula

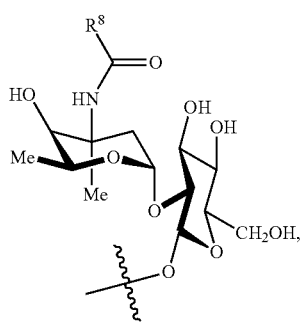

wherein R[8] is alkyl, aryl, heterocyclyl, heteroaryl; a wavy line indicates a point of bonding;

or an epimer thereof or deoxy analog thereof.

14. A method of preparing the antibiotic glycopeptide-analogous amidine compound of claim 1, comprising contacting the glycopeptide-analogous thioamide compound and ammonia, in the presence of a silver ion, optionally in a solvent.

15. The method of claim 14 wherein, the silver ion is provided by any one of silver acetate, silver triflate, silver tetrafluoborate, silver trifluoroacetate, or silver antimonyhexafluoride, or any combination thereof; or wherein the contacting is in a solvent comprising water or alcohol, or both; or wherein the contacting is at about 25° C.; or any combination thereof.

16. The method of claim 14, wherein the thioamide compound is derived from a fermentation process.

17. The method of claim 14 comprising preparing a vancomycin [Ψ[C(=NH)NH]Tpg[4]]-amidine analog of formula (IA)

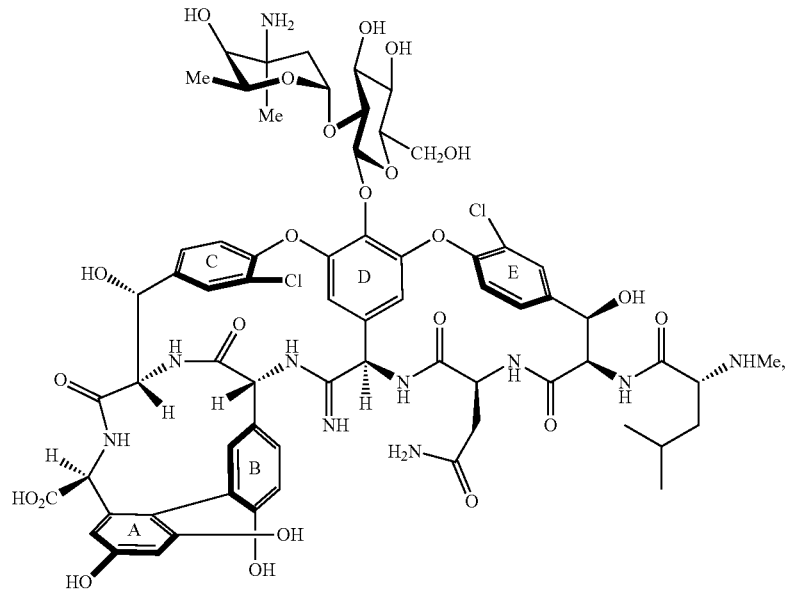

or of formula (IB)

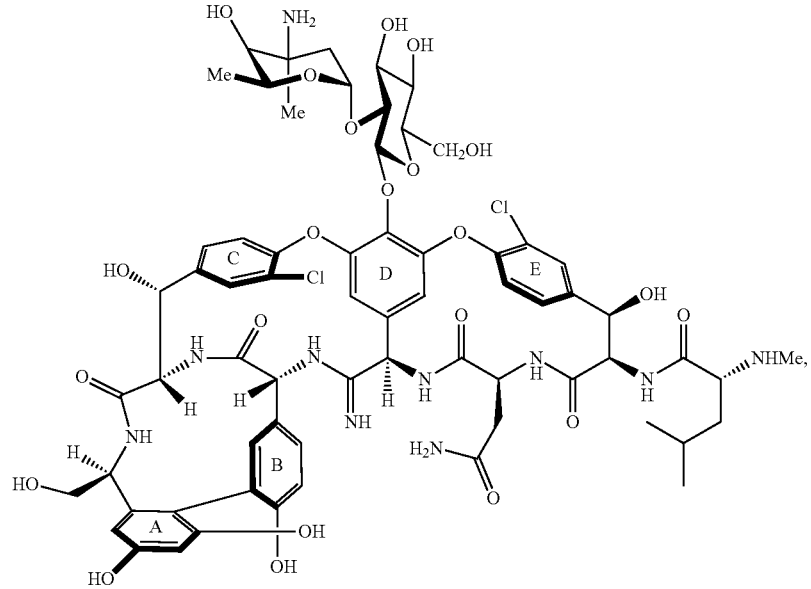

or of formula (IC)
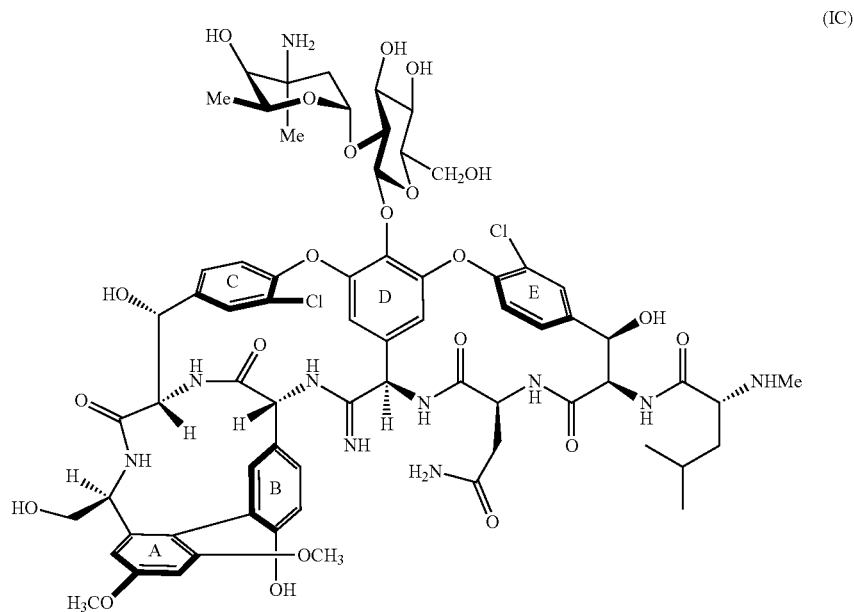
by contacting a vancomycin [Ψ[C(=S)NH]Tpg$^4$]-thioamide analog of formula (IIIA)
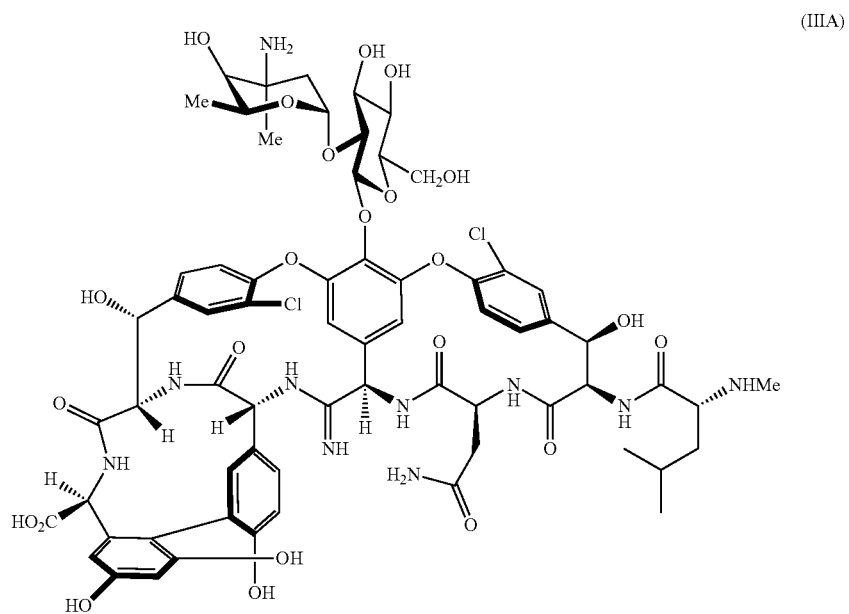

or of formula (IIIB)
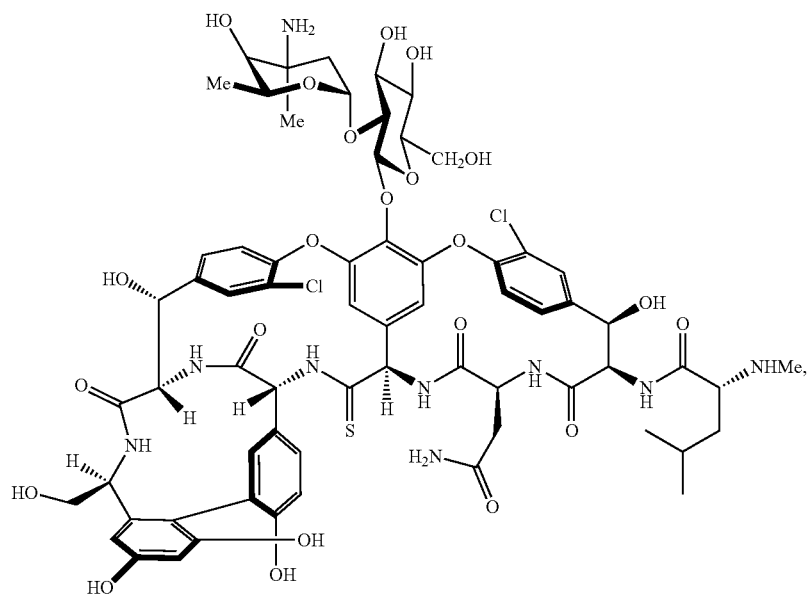
or of formula (IIIC)
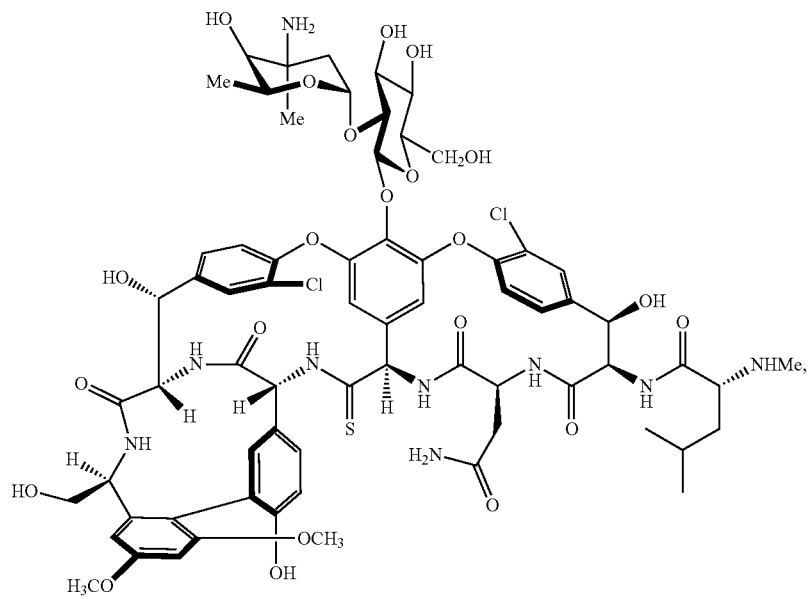

respectively,
or comprising preparing a vancomycin aglycone [Ψ[C(=NH)NH]Tpg$^4$]-amidine analog of formula (IIA)
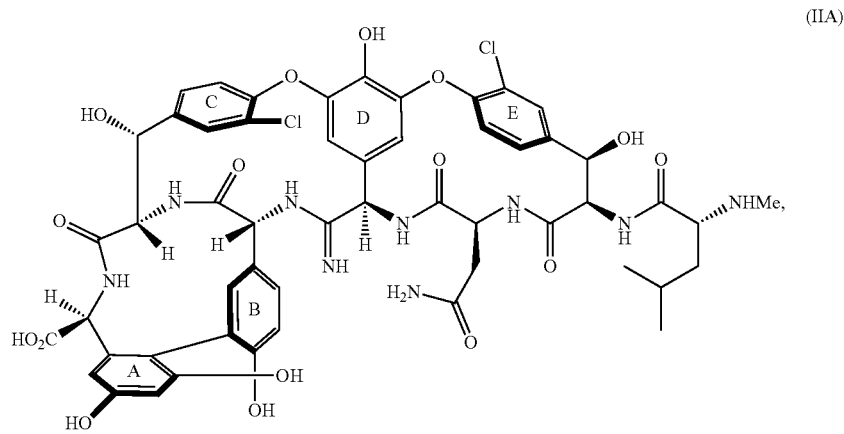
(IIA)
or of formula (IIB)
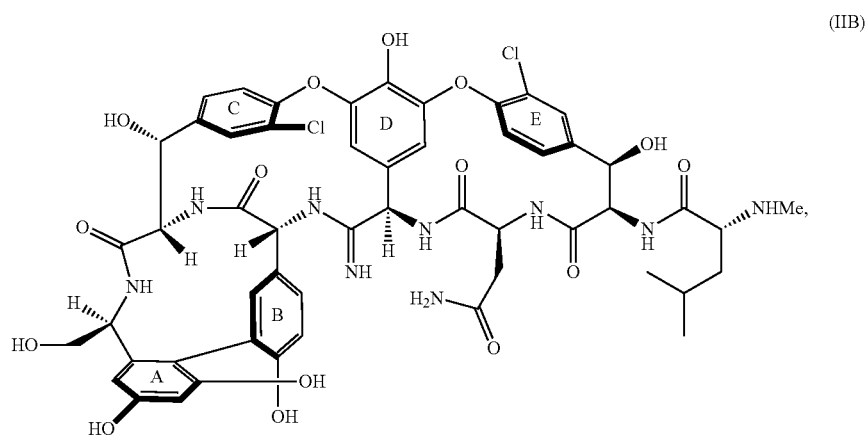
(IIB)
or of formula (IIC)
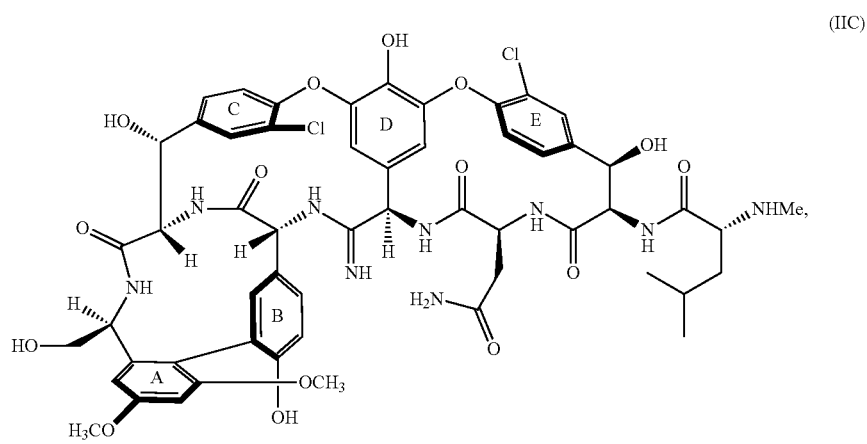
(IIC)

by contacting a vancomycin [Ψ[C(=S)NH]Tpg⁴]-thioamide analog of formula (IVA)
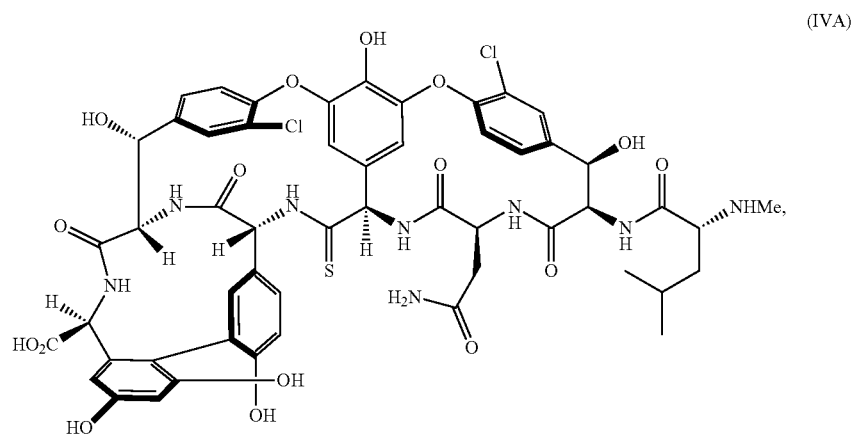
(IVA)
or of formula (IVB)
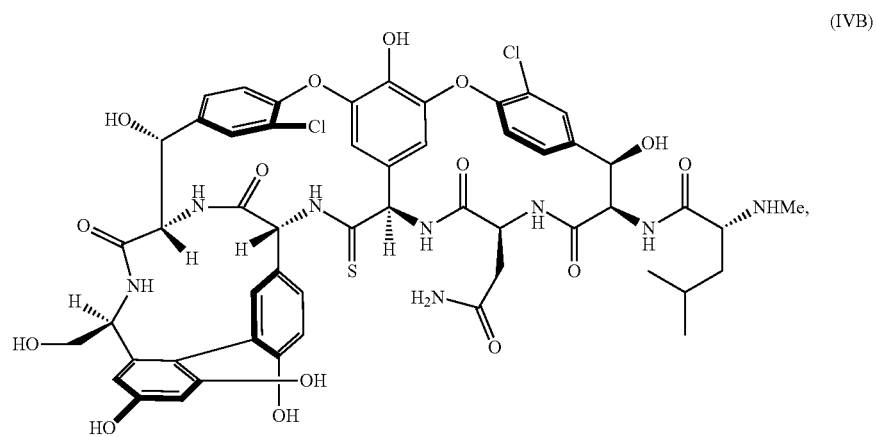
(IVB)

or of formula (IVC)

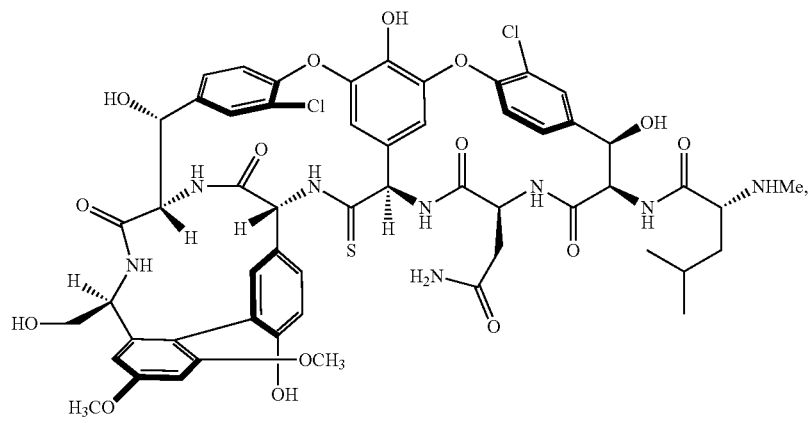

respectively,
and a solution of a silver salt and ammonia in an alcoholic solvent, to provide the respective vancomycin amidine analog or vancomycin amidine aglycone analog, respectively.

18. A method of killing a vancomycin-resistant bacterial strain, comprising contacting the bacteria with an effective amount or concentration of an antibiotic compound of claim 1.

19. A method of treating an infection in a patient caused by a bacterial population comprising a vancomycin-resistant bacterial strain, comprising administering to the patient an effective amount of an antibiotic compound of claim 1.

20. A compound of formula

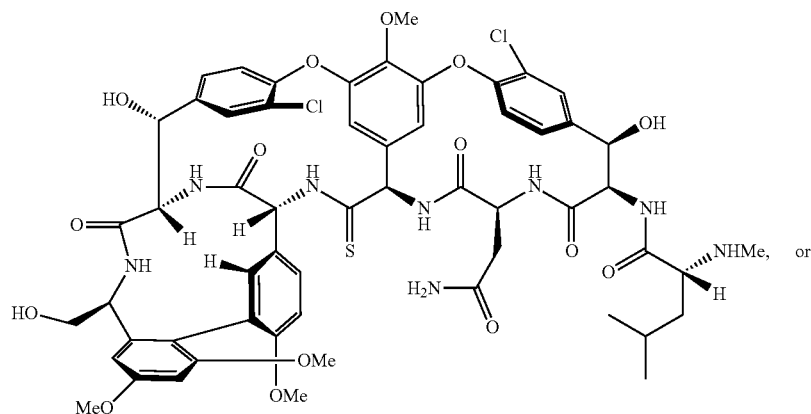

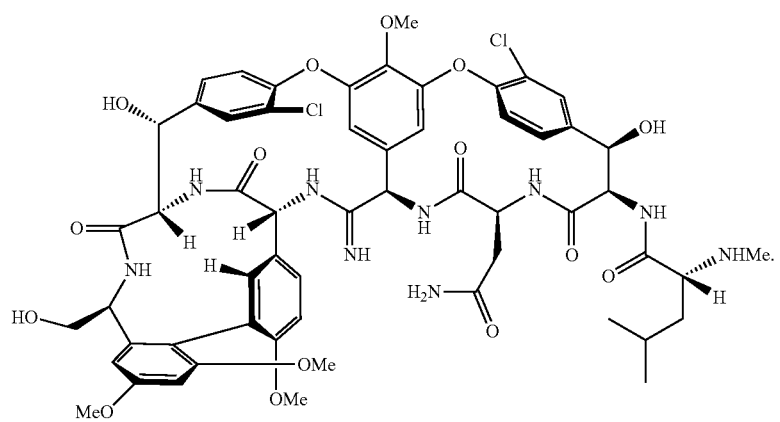
* * * * *

UNITED STATES PATENT AND TRADEMARK OFFICE
CERTIFICATE OF CORRECTION

Page 1 of 1

PATENT NO. : 9,879,049 B2
APPLICATION NO. : 14/236876
DATED : January 30, 2018
INVENTOR(S) : Dale L. Boger It is certified that error appears in the above-identified patent and that said Letters Patent is hereby corrected as shown below:

In the Specification

Column 1, Lines 19-24, the paragraph STATEMENT OF GOVERNMENT SUPPORT should be changed to:
-- STATEMENT OF GOVERNMENT LICENSE RIGHTS
This invention was made with government support under grant numbers CA041101 and CA144333 awarded by the National Institutes of Health. The government has certain rights in the invention. --

Signed and Sealed this
Seventh Day of April, 2020

Andrei Iancu
*Director of the United States Patent and Trademark Office*